United States Patent
Bousamra et al.

(10) Patent No.: US 9,117,015 B2
(45) Date of Patent: Aug. 25, 2015

(54) MANAGEMENT METHOD AND SYSTEM FOR IMPLEMENTATION, EXECUTION, DATA COLLECTION, AND DATA ANALYSIS OF A STRUCTURED COLLECTION PROCEDURE WHICH RUNS ON A COLLECTION DEVICE

(75) Inventors: Steven A. Bousamra, Carmel, IN (US); Abhishek S. Soni, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 937 days.

(21) Appl. No.: 13/165,220

(22) Filed: Jun. 21, 2011

(65) Prior Publication Data

US 2012/0089893 A1    Apr. 12, 2012

Related U.S. Application Data

(63) Continuation-in-part of application No. 12/974,859, filed on Dec. 21, 2010, and a continuation-in-part of application No. 12/643,415, filed on Dec. 21, 2009, and a continuation-in-part of application No.

(Continued)

(51) Int. Cl.
  *G06F 13/00* (2006.01)
  *G06F 19/00* (2011.01)
  (Continued)

(52) U.S. Cl.
  CPC .......... *G06F 19/3456* (2013.01); *A61B 5/0022* (2013.01); *A61B 5/14532* (2013.01);
  (Continued)

(58) Field of Classification Search
  CPC .. G06F 19/325; G06F 19/345; G06F 19/3418

USPC .......................................... 711/154; 714/807
  See application file for complete search history.

(56) References Cited

U.S. PATENT DOCUMENTS

| 4,151,845 A | 5/1979 | Clemens |
| 4,731,726 A | 3/1988 | Allen, III |

(Continued)

FOREIGN PATENT DOCUMENTS

| CN | 101325906 A | 12/2008 |
| DE | 102005041627 A1 | 3/2007 |

(Continued)

OTHER PUBLICATIONS

Non-Final Office Action pertaining to U.S. Appl. No. 12/818,875, dated Apr. 2, 2012.

(Continued)

*Primary Examiner* — William Bashore
*Assistant Examiner* — Gregory A Distefano
(74) *Attorney, Agent, or Firm* — Dinsmore & Shohl LLP

(57) ABSTRACT

A collection device for performing a structured collection procedure may include a processor that executes program instructions communicably coupled to at least one memory. The processor can initiate a schedule of events of the structured collection procedure upon one or more entry criterions being met and segregate the at least one memory into a primary data store and a secondary data store. The processor can write structured patient data collected in accordance to the schedule of events to the secondary data store. The processor can transform a relevant portion of the structured patient data into an evaluated data object. The processor can generate a data abstraction based in part upon the evaluated data object. The processor can link the primary data store and the secondary data store with the data abstraction.

27 Claims, 36 Drawing Sheets

Related U.S. Application Data

12/818,310, filed on Jun. 18, 2010, which is a continuation-in-part of application No. 12/643,338, filed on Dec. 21, 2009.

(60) Provisional application No. 61/140,270, filed on Dec. 23, 2008.

(51) Int. Cl.
    *A61B 5/00*            (2006.01)
    *A61B 5/145*          (2006.01)

(52) U.S. Cl.
    CPC ............. *A61B5/4833* (2013.01); *A61B 5/4839* (2013.01); *G06F 19/325* (2013.01); *A61B 5/7275* (2013.01); *G06F 19/345* (2013.01); *G06F 19/3418* (2013.01)

(56) References Cited

U.S. PATENT DOCUMENTS

| | | | |
|---|---|---|---|
| 4,803,625 A | 2/1989 | Fu et al. | |
| 5,364,346 A | 11/1994 | Schrezenmeir | |
| 5,377,258 A | 12/1994 | Bro | |
| 5,549,117 A * | 8/1996 | Tacklind et al. | 600/529 |
| 5,572,421 A | 11/1996 | Altman et al. | |
| 5,576,952 A | 11/1996 | Stutman et al. | |
| 5,594,903 A * | 1/1997 | Bunnell et al. | 717/162 |
| 5,665,065 A | 9/1997 | Colman et al. | |
| 5,722,418 A | 3/1998 | Bro | |
| 5,822,715 A | 10/1998 | Worthington et al. | |
| 5,840,020 A | 11/1998 | Heinonen et al. | |
| 5,868,669 A | 2/1999 | Iliff | |
| 5,879,163 A | 3/1999 | Brown et al. | |
| 5,897,493 A | 4/1999 | Brown | |
| 5,971,922 A | 10/1999 | Arita et al. | |
| 6,018,713 A | 1/2000 | Coli et al. | |
| 6,039,688 A | 3/2000 | Douglas et al. | |
| 6,108,665 A | 8/2000 | Bair et al. | |
| 6,234,964 B1 | 5/2001 | Iliff | |
| 6,241,633 B1 | 6/2001 | Conroy | |
| 6,269,314 B1 | 7/2001 | Itawaki et al. | |
| 6,326,160 B1 | 12/2001 | Dunn et al. | |
| 6,338,039 B1 | 1/2002 | Lonski et al. | |
| 6,352,505 B1 | 3/2002 | Bortz | |
| 6,379,301 B1 | 4/2002 | Worthington et al. | |
| 6,424,847 B1 | 7/2002 | Mastrototaro et al. | |
| 6,425,863 B1 | 7/2002 | Werner et al. | |
| 6,544,212 B2 | 4/2003 | Galley et al. | |
| 6,567,785 B2 | 5/2003 | Clendenon | |
| 6,575,900 B1 | 6/2003 | Zweig et al. | |
| 6,645,368 B1 | 11/2003 | Beaty et al. | |
| 6,656,114 B1 | 12/2003 | Poulsen et al. | |
| 6,691,043 B2 | 2/2004 | Ribeiro, Jr. | |
| 6,770,029 B2 | 8/2004 | Iliff | |
| 6,835,175 B1 | 12/2004 | Porumbescu | |
| 6,879,970 B2 | 4/2005 | Shiffman et al. | |
| 6,923,763 B1 | 8/2005 | Kovatchev et al. | |
| 6,954,662 B2 | 10/2005 | Freger et al. | |
| 7,179,226 B2 | 2/2007 | Crothall et al. | |
| 7,229,430 B2 | 6/2007 | Hickle et al. | |
| 7,241,265 B2 | 7/2007 | Cummings et al. | |
| 7,266,400 B2 | 9/2007 | Fine et al. | |
| 7,278,983 B2 | 10/2007 | Ireland et al. | |
| 7,381,523 B2 | 6/2008 | Efendic | |
| 7,389,133 B1 | 6/2008 | Kotulla et al. | |
| 7,404,796 B2 | 7/2008 | Ginsberg | |
| 7,405,196 B2 | 7/2008 | Rosskamp et al. | |
| 7,413,749 B2 | 8/2008 | Wright et al. | |
| 7,415,447 B2 | 8/2008 | Shiffman et al. | |
| 7,429,938 B1 * | 9/2008 | Corndorf | 341/67 |
| 7,509,156 B2 | 3/2009 | Flanders | |
| 7,523,040 B2 | 4/2009 | Kirchhoff et al. | |
| 7,553,281 B2 | 6/2009 | Hellwig et al. | |
| 7,676,329 B2 | 3/2010 | Garczarek et al. | |
| 7,685,000 B1 | 3/2010 | Petit et al. | |
| 7,734,323 B2 | 6/2010 | Blomquist et al. | |
| 7,761,310 B2 | 7/2010 | Rodgers | |
| 7,766,830 B2 | 8/2010 | Fox et al. | |
| 8,078,592 B2 | 12/2011 | Gejdos et al. | |
| 8,117,020 B2 | 2/2012 | Abensour et al. | |
| 2002/0059030 A1 | 5/2002 | Otworth et al. | |
| 2002/0107476 A1 | 8/2002 | Mann et al. | |
| 2002/0143563 A1 | 10/2002 | Hufford et al. | |
| 2002/0161288 A1 | 10/2002 | Shin et al. | |
| 2003/0028399 A1 | 2/2003 | Davis et al. | |
| 2003/0031094 A1 * | 2/2003 | Banno et al. | 368/88 |
| 2003/0104982 A1 | 6/2003 | Wittmann et al. | |
| 2003/0130616 A1 | 7/2003 | Steil et al. | |
| 2003/0208113 A1 | 11/2003 | Mault et al. | |
| 2003/0211617 A1 | 11/2003 | Jones | |
| 2004/0122701 A1 | 6/2004 | Dahlin et al. | |
| 2004/0122709 A1 | 6/2004 | Avinash et al. | |
| 2004/0130616 A1 * | 7/2004 | Tseng | 348/61 |
| 2004/0162678 A1 * | 8/2004 | Hetzel et al. | 702/19 |
| 2004/0243443 A1 | 12/2004 | Asano et al. | |
| 2004/0247748 A1 | 12/2004 | Bronkema | |
| 2005/0016844 A1 | 1/2005 | Burke et al. | |
| 2005/0020903 A1 | 1/2005 | Krishnan et al. | |
| 2005/0021372 A1 | 1/2005 | Mikkelsen et al. | |
| 2005/0049179 A1 | 3/2005 | Davidson et al. | |
| 2005/0119540 A1 | 6/2005 | Potts et al. | |
| 2005/0119788 A1 | 6/2005 | Engleson et al. | |
| 2006/0010098 A1 | 1/2006 | Goodnow et al. | |
| 2006/0025931 A1 | 2/2006 | Rosen et al. | |
| 2006/0030890 A1 | 2/2006 | Cosentino et al. | |
| 2006/0031094 A1 | 2/2006 | Cohen et al. | |
| 2006/0171503 A1 | 8/2006 | O'Hara et al. | |
| 2006/0173406 A1 | 8/2006 | Hayes et al. | |
| 2006/0195022 A1 | 8/2006 | Trepagnier et al. | |
| 2006/0195029 A1 | 8/2006 | Shults et al. | |
| 2006/0195342 A1 | 8/2006 | Khan et al. | |
| 2006/0253296 A1 | 11/2006 | Liisberg et al. | |
| 2006/0271404 A1 | 11/2006 | Brown | |
| 2006/0287883 A1 | 12/2006 | Turgiss et al. | |
| 2007/0048691 A1 | 3/2007 | Brown | |
| 2007/0055483 A1 | 3/2007 | Lee et al. | |
| 2007/0100659 A1 | 5/2007 | Preiss | |
| 2007/0106135 A1 | 5/2007 | Sloan et al. | |
| 2007/0129610 A1 | 6/2007 | Squilla | |
| 2007/0162304 A1 | 7/2007 | Rodgers | |
| 2007/0198296 A1 | 8/2007 | Pellinat et al. | |
| 2007/0213604 A1 | 9/2007 | Brown | |
| 2007/0253904 A1 | 11/2007 | Gunton et al. | |
| 2007/0282636 A1 | 12/2007 | Sauk et al. | |
| 2008/0025591 A1 | 1/2008 | Bhanot et al. | |
| 2008/0109043 A1 | 5/2008 | Salo et al. | |
| 2008/0125636 A1 | 5/2008 | Ward et al. | |
| 2008/0146895 A1 | 6/2008 | Olson et al. | |
| 2008/0154513 A1 | 6/2008 | Kovatchev et al. | |
| 2008/0172027 A1 | 7/2008 | Blomquist | |
| 2008/0177119 A1 | 7/2008 | Juttu et al. | |
| 2008/0177149 A1 | 7/2008 | Weinert et al. | |
| 2008/0177165 A1 | 7/2008 | Blomquist et al. | |
| 2008/0183494 A1 | 7/2008 | Cuddihy et al. | |
| 2008/0201325 A1 | 8/2008 | Doniger et al. | |
| 2008/0206799 A1 | 8/2008 | Blomquist | |
| 2008/0214919 A1 | 9/2008 | Harmon et al. | |
| 2008/0228056 A1 | 9/2008 | Blomquist et al. | |
| 2008/0234943 A1 | 9/2008 | Ray et al. | |
| 2008/0234992 A1 | 9/2008 | Ray et al. | |
| 2008/0243902 A1 | 10/2008 | Rong et al. | |
| 2008/0255438 A1 | 10/2008 | Saidara et al. | |
| 2008/0262745 A1 | 10/2008 | Polidori | |
| 2008/0269585 A1 | 10/2008 | Ginsberg | |
| 2008/0306353 A1 | 12/2008 | Douglas et al. | |
| 2008/0319384 A1 | 12/2008 | Yodfat et al. | |
| 2009/0006061 A1 | 1/2009 | Thukral et al. | |
| 2009/0018406 A1 | 1/2009 | Yodfat et al. | |
| 2009/0150177 A1 | 6/2009 | Buck et al. | |
| 2009/0150186 A1 | 6/2009 | Cohen et al. | |
| 2009/0164239 A1 | 6/2009 | Hayter et al. | |
| 2009/0176692 A1 | 7/2009 | Habermann et al. | |
| 2009/0177147 A1 | 7/2009 | Blomquist et al. | |

(56) References Cited

U.S. PATENT DOCUMENTS

| | | |
|---|---|---|
| 2009/0234262 A1 | 9/2009 | Reid et al. |
| 2009/0246289 A1* | 10/2009 | Superko et al. ............... 424/523 |
| 2009/0247836 A1 | 10/2009 | Cole et al. |
| 2009/0253970 A1 | 10/2009 | Bashan et al. |
| 2009/0253973 A1 | 10/2009 | Bashan et al. |
| 2009/0281393 A1 | 11/2009 | Smith |
| 2010/0016700 A1 | 1/2010 | Sieh et al. |
| 2010/0138197 A1 | 6/2010 | Sher |
| 2010/0141656 A1 | 6/2010 | Krieftewirth |
| 2010/0160757 A1 | 6/2010 | Weinert et al. |
| 2010/0174553 A1 | 7/2010 | Kaufman et al. |
| 2010/0198142 A1 | 8/2010 | Sloan et al. |
| 2010/0198520 A1 | 8/2010 | Breton et al. |
| 2010/0218132 A1 | 8/2010 | Soni et al. |
| 2010/0222765 A1 | 9/2010 | Blomquist et al. |
| 2010/0262434 A1 | 10/2010 | Shaya |
| 2010/0265073 A1 | 10/2010 | Harper |
| 2010/0274497 A1 | 10/2010 | Rush |
| 2010/0330598 A1 | 12/2010 | Thukral et al. |
| 2010/0331650 A1 | 12/2010 | Batman et al. |
| 2010/0331651 A1 | 12/2010 | Groll |
| 2011/0015511 A1 | 1/2011 | Bousamra et al. |
| 2011/0071365 A1 | 3/2011 | Lee et al. |
| 2011/0212090 A1* | 9/2011 | Pedersen et al. ............ 424/133.1 |
| 2012/0088989 A1 | 4/2012 | Bousamra et al. |
| 2012/0226117 A1 | 9/2012 | Lamego et al. |

FOREIGN PATENT DOCUMENTS

| | | |
|---|---|---|
| EP | 1702559 A2 | 9/2006 |
| EP | 1728469 A2 | 12/2006 |
| EP | 1956508 A2 | 8/2008 |
| EP | 2006786 A1 | 12/2008 |
| FR | 2760962 A1 | 3/1997 |
| JP | 2001000397 A | 1/2001 |
| JP | 2003204941 A | 7/2003 |
| JP | 2003521972 A | 7/2003 |
| JP | 2005011329 A | 1/2005 |
| JP | 2008506468 A | 3/2008 |
| WO | 94/20916 A1 | 9/1994 |
| WO | 9901836 | 1/1999 |
| WO | 0009007 | 2/2000 |
| WO | 0042907 A1 | 7/2000 |
| WO | 0122343 A2 | 3/2001 |
| WO | 0128416 A1 | 4/2001 |
| WO | 0133314 A2 | 5/2001 |
| WO | 01/52727 A1 | 7/2001 |
| WO | 03/002258 A1 | 1/2003 |
| WO | 03/046695 A2 | 6/2003 |
| WO | 03/082096 A1 | 10/2003 |
| WO | 2004/015539 A2 | 2/2004 |
| WO | 2004/084820 A2 | 10/2004 |
| WO | 2006017358 A1 | 2/2006 |
| WO | 2007/081853 A2 | 7/2007 |
| WO | 2007117719 A2 | 10/2007 |
| WO | 2007/149319 A2 | 12/2007 |
| WO | 2007144419 A2 | 12/2007 |
| WO | 2008/091320 A2 | 7/2008 |
| WO | 2008/105859 A1 | 9/2008 |
| WO | 2008/131324 A1 | 10/2008 |
| WO | 2009/009528 A2 | 1/2009 |
| WO | 2009/013637 A2 | 1/2009 |
| WO | 2009/075925 A1 | 6/2009 |
| WO | 2009/146119 A2 | 12/2009 |
| WO | 2010/000266 A1 | 1/2010 |
| WO | 2010/039743 A1 | 4/2010 |
| WO | 2010063758 A1 | 6/2010 |
| WO | 2010/072386 A2 | 7/2010 |
| WO | 2010/075350 A1 | 7/2010 |
| WO | 2010072387 A2 | 7/2010 |
| WO | 2010/089304 A1 | 8/2010 |
| WO | 2010/089305 A1 | 8/2010 |
| WO | 2010/089306 A1 | 8/2010 |
| WO | 2010/089307 A1 | 8/2010 |
| WO | 2010/097796 A1 | 9/2010 |
| WO | 2010063758 A4 | 9/2010 |

OTHER PUBLICATIONS

Non-final Office Action pertaining to U.S. Appl. No. 12/818,310, dated Sep. 26, 2012.
Final Office Action pertaining to U.S. Appl. No. 12/818,875 dated Sep. 28, 2012.
Non-final Office Action pertaining to U.S. Appl. No. 12/643,415 dated Sep. 13, 2012.
Non-final Office Action pertaining to U.S. Appl. No. 12/818,795 dated Sep. 6, 2012.
Breton, M. et al.; Analysis, Modeling, and Simulation of the Accuracy of Continuous Glucose Sensors; Journal of Diabetes Science and Technology; Sep. 2008; pp. 853-862; vol. 2, Issue 5; Diabetes Technology Society.
Final Office Action regarding U.S. Appl. No. 12/818,930 mailed Mar. 15, 2013.
Accu-Chek Spirit Pump User Guide, Sep. 2008, pp. 1-201.
Accu-Chek Pocket Compass Software with Bolus Calculator User Guide, Oct. 2005, pp. 1-174.
Accu-Chek Aviva Blood Glucose Meter Owner's Booklet, Sep. 2008, pp. 1-92.
Accu-Chek 360 Diabetes Management System, Aug. 24, 2010, pp. 1-2.
Accu-Chek Smart Pix Device Reader User's Manual, Sep. 2008, pp. 1-92.
De Groen, et al., "Applying World Wide Web Technology to the Study of Patients with Rare Diseases, Annals of Internal Medicine", vol. 129, No. 2, Jul. 15, 1998, pp. 107-113, XP002587966, 1998.
Dassau, et al., "Detection of a Meal Using Continuous Glucose Monitoring", Diabetes Care, vol. 31, No. 2, Feb. 2008, pp. 295-300.
Gerstein et al., "A randomized trial of adding insulin glargine vs. avoidance of insulin in people with Type 2 diabetes on either no oral glucose-lowering agents or submaximal doses of metformin and/or sulphonylureas. The Canadian INSIGHT (Implementing New Strategies with Insulin Glargine for Hyperclycaemia Treatment) Study", Diabetic Medicine, vol. 23, pp. 736-742, 2006.
Hirsch et al., "A Real-World Approach to Insulin Therapy in Primary Care Practice", Practical Pointers, Clinical Diabetes, vol. 23, Nov. 2, 2005.
Nathan, et al., "Medical Management of Hyperglycemia in Type 2 Diabetes: A Consensus Algorithm for the Initiation and Adjustment of Therapy", Diabetes Care, vol. 31, No. 12: pp. 1-11, Dec. 2008.
Riddle, et al., "The Treat-to-Target Trial, Randomized addition of glargine or human NPH insulin to oral therapy of type 2 diabetic patients", Diabetes Care, vol. 26, No. 11: pp. 2080-3086, Nov. 2003.
Crowe, et al., "Time Synching or Time Sinking?", Diabetes Technology & Therapeutics, vol. 7, No. 5, 2005.
Munro, et al., "Association Between Medication Regimen Complexity and Achievement of Therapeutic Goals in Patients with Type 2 Diabetes", School of Pharmacy, The Robert Gordon University, Aberdeen, AB10 1 FR (k.munroe@rgu.ac.uk), pp. 1, 2.
Ingersoll, et al., "The Impact of Medication Regimen Factors on Adherence to Chronic Treatment: a Review of Literature", NIH Public Access, Author Manuscript, J Behav Med. Jun. 2008; 31(3): 213-224. doi:10.1007/ s10865-007-9147-y; pp. 1-16.
Pollack, et al., "Impact of treatment Complexity on Adherence and Glycemic Control: An Analysis of Oral Antidiabetic Agents", www.jcomjournal.com, vol. 17, No. 6, Jun. 2010, pp. 257-265.
Joslin Diabetes Center & Joslin Clinic, "Clinical Guideline for Pharmacological Management of Type 2 Diabetes", Jan. 12, 2007, pp. 1-9.
Joslin Diabetes Center & Joslin Clinic, "Clinical Guideline for Adults with Diabetes", May 21, 2010, pp. 1-13.
International Search Report, Application No. PCT/EP2009/009170 filed Dec. 21, 2009, completion of ISR is Sep. 24, 2010, pp. 1-24.
International Search Report, Application No. PCT/EP2009/009171 filed Dec. 21, 2009, completion of ISR is Jun. 21, 2010, pp. 1-14.

(56) References Cited

OTHER PUBLICATIONS

Lustria, et al., "Computer-Tailored Health Interventions Delivered Over the Web: Review and Analysis of Key Components", U.S. National Library of Medicine, National Institute of Health, 2009, p. 1.

Montani et al., "Integrating Case Based and Rule Based Reasoning in a Decision Support System: Evalation with Simulated Patients", AMIA, Inc., pp. 887-891, 1999.

Montani et al., "Managing diabetic patients through a Multi Modal Reasoning methodology", International Journal of Medical Informatics, vol. 58, Complete, pp. 243-256, Sep. 1, 2000.

Schmidt et al., "Case-based Reasoning for Medical Knowledge-based Systems", Institute for Medical Informatics and Biometry, University of Rostock Rembrandtstr. 16/17, D-18055 Rostock, Germany, 2000.

Denis Raccah, "Insulin therapy in patients with type 2 diabetes mellitus: Treatment to target fasting and postprandial blood glucose levels", Insulin 1:158-165, 2006.

Morgan et al., "Uncertainty a Guide to Dealing with Uncertainty in Quantitative Risk and Poly Analysis", Cambridge University Press, pp. 307-310, 1990.

Brand et al., "Updating uncertainty in an integrated risk assessment: Conceptual framework and methods", Risk Analysis 1995 US, vol. 15, No. 6, pp. 719-731, 1995.

Huang Elbert S., "The key to preventing burnout: understanding the burden of diabetes treatment", DiabetesVoice, vol. 53, Issue 3, pp. 33-35, Dec. 2008.

Larimer, et al., "Relapse Prevention, an Overview of Marlatt's Cognitive-Behavioral Model", Alcohol Research & Health, vol. 23, No. 2, pp. 151-160, 1999.

Marlatt, et al., "Clinical Guidelines for Implementing Relapse Prevention Therapy", Addictive Behaviors Research Center/University of Washington, pp. 1-49, Dec. 2002.

Non-Final Office Action pertaining to U.S. Appl. No. 12/643,338 dated Apr. 26, 2012.

Final Office Action pertaining to U.S. Appl. No. 12/818,894 dated Nov. 21, 2012.

Final Office Action pertaining to U.S. Appl. No. 12/643,338 dated Dec. 3, 2012.

International Preliminary Report on Patentability completed Nov. 13, 2012 pertaining to International Application No. PCT/EP2011/002925.

Non-final Office Action pertaining to U.S. Appl. No. 13/107,436, dated May 31, 2013.

Final Office Action pertaining to U.S. Appl. No. 12/643,415, dated May 17, 2013.

USPTO Non Final Rejection mailed Dec. 18, 2013 in reference to co-pending U.S. Appl. No. 12/818,310, filed Jun. 18, 2010.

USPTO Final Rejection mailed Feb. 21, 2014 in reference to co-pending U.S. Appl. No. 12/808,894, filed Jun. 18, 2010.

Non-Final Office Action pertaining to U.S. Appl. No. 12/818,930, dated Aug. 27, 2012.

Final Office Action pertaining to U.S. Appl. No. 13/165,220 dated Feb. 12, 2015.

\* cited by examiner

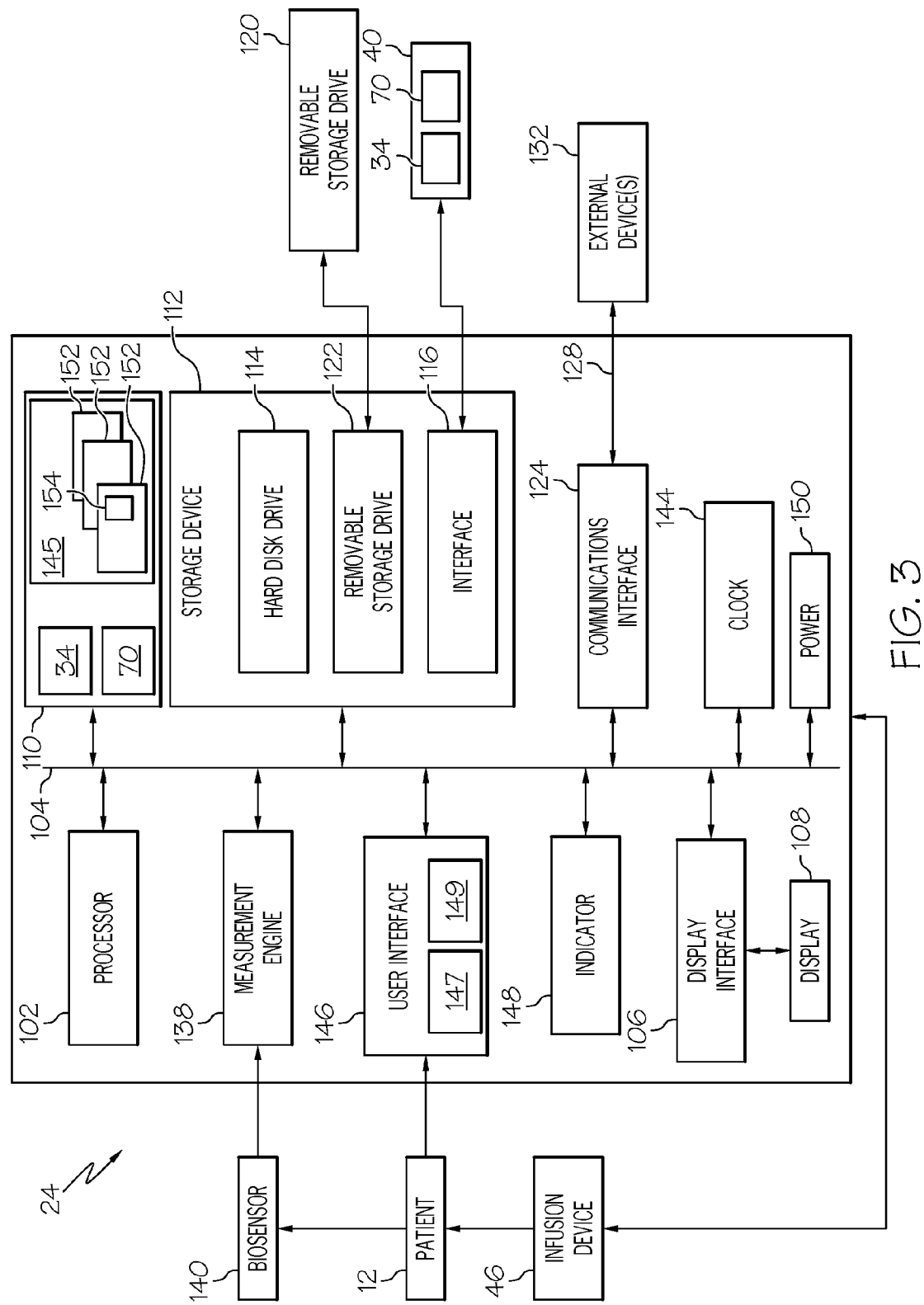

| 145 | | | | | |
|---|---|---|---|---|---|
| 237a | 240a | 256a | 163 | 257 | |
| 237b | 240b | 256b | 12/23/2009 8:00 | 1 | |
| 237c | 240c | 256c | 12/23/2009 9:00 | 2 | 5, 1 |
| 237d | 240d | 256d | 12/23/2009 9:30 | 3 | 5, 1 |
| ... | ... | ... | 12/23/2009 10:00 | <null> | |
| 237n | 240n | 256n | mm/dd/yyyy hh:mm | n | |

152 { 237a–237n }
169 { date column }
170 mm/dd/yyyy hh:mm
167 { 257 column }
156 { right brace }

FIG. 4

| PARAMETERS | bG (BIOSENSOR) MEASUREMENT | MEAL SIZE (S, M, OR L) | ENERGY LEVEL (1-5) | TIMING | ACCEPTANCE CRITERIA | GUIDANCE | OPTIONS |
|---|---|---|---|---|---|---|---|
| bG LEVEL TRENDING | | | | | | | |
| ENTRY CRITERIA | | | | MM-DD-YYYY | AFFIRMS GUIDANCE, IF NOT ADD 1 DAY TO TIMING | ARE YOU WILLING TO CONDUCT A TEST OVER 3 CONSECUTIVE DAYS? | |
| EXIT CRITERIA | | | | MM-DD-YYYY | ENTRY TIMING + 3 DAYS | | |
| BEFORE BREAKFAST | Y | | Y | HHMM | | PLEASE INDICATE ENERGY LEVEL | 1 |
| $n_1$ HOURS AFTER BREAKFAST | Y | Y | Y | $n_1$ | ± 30 MINUTES OF $n_1$ | PLEASE INDICATE MEAL SIZE & ENERGY LEVEL | |
| BEFORE LUNCH | Y | | Y | | | PLEASE INDICATE ENERGY LEVEL | |
| $n_2$ HOURS AFTER LUNCH | Y | Y | Y | $n_2$ | ± 30 MINUTES OF $n_1$ | PLEASE INDICATE MEAL SIZE & ENERGY LEVEL | |
| BEFORE DINNER | Y | | Y | | | PLEASE INDICATE ENERGY LEVEL | |
| $n_3$ HOURS AFTER DINNER | Y | Y | Y | $n_3$ | ± 30 MINUTES OF $n_1$ | PLEASE INDICATE MEAL SIZE & ENERGY LEVEL | |
| BEFORE BED | Y | | Y | | | PLEASE INDICATE ENERGY LEVEL | |

FIG. 7B

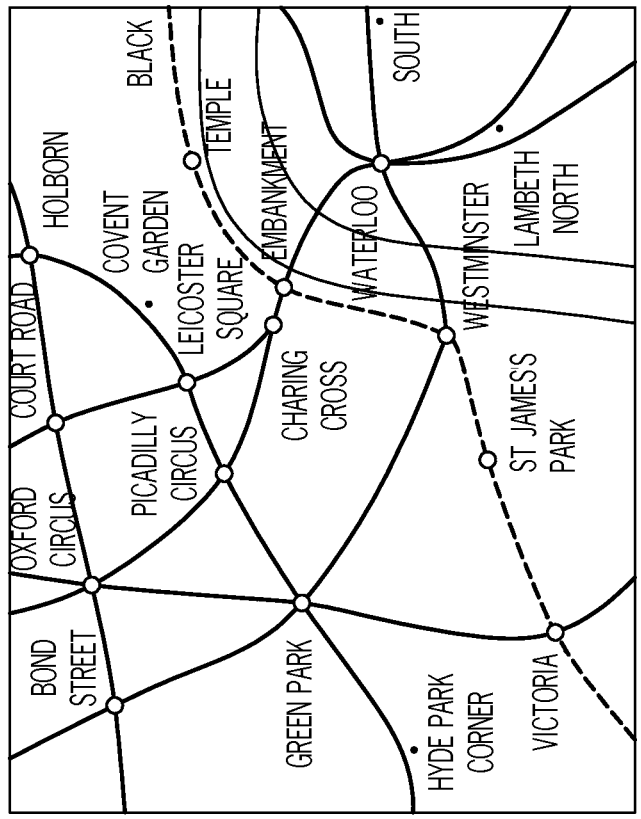
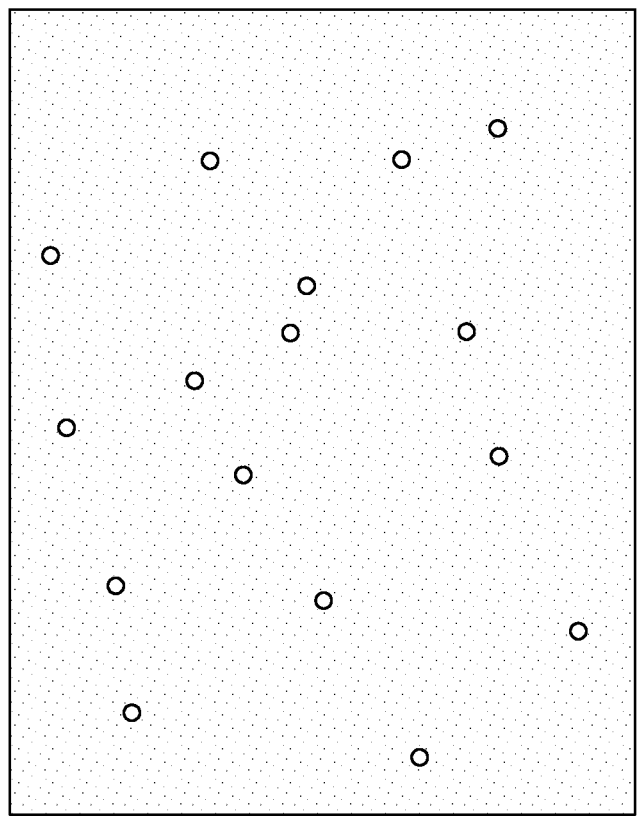
FIG. 10A

MANAGEMENT METHOD AND SYSTEM FOR IMPLEMENTATION, EXECUTION, DATA COLLECTION, AND DATA ANALYSIS OF A STRUCTURED COLLECTION PROCEDURE WHICH RUNS ON A COLLECTION DEVICE

CROSS-REFERENCE TO RELATED APPLICATIONS

The present application is a continuation-in-part of U.S. patent application Ser. No. 12/974,859 filed Dec. 21, 2010, which itself was a continuation in part of U.S. patent application Ser. No. 12/643,415 filed Dec. 21, 2009 (WP 26405), which claims priority to U.S. Provisional Application Ser. No. 61/140,270 filed Dec. 23, 2008. The present application is also a continuation-in-part of U.S. patent application Ser. No. 12/818,310 filed Jun. 18, 2010 (WP 26287), which is a continuation-in-part of U.S. patent application Ser. No. 12/643,338 filed Dec. 21, 2009 (WP 25378), which also claims priority to U.S. Provisional Application Ser. No. 61/140,270 filed Dec. 23, 2008. All of the above applications are incorporated by reference herein in their entirety.

TECHNICAL FIELD

Embodiments of the present invention relate generally to devices collecting physiological information, and particularly to a system and method managing the implementation, execution, data collection, and data analysis of a structured collection procedure or protocol running on a portable, hand-held collection device.

BACKGROUND

A disease which is long lasting or which reoccurs often is defined typically as a chronic disease. Known chronic diseases include, among others, depression, compulsive obsession disorder, alcoholism, asthma, autoimmune diseases (e.g. ulcerative colitis, lupus erythematosus), osteoporosis, cancer, and diabetes mellitus. Such chronic diseases require chronic care management for effective long-term treatment. After an initial diagnosis, one of the functions of chronic care management is then to optimize a patient's therapy of the chronic disease.

In the example of diabetes mellitus, which is characterized by hyperglycemia resulting from inadequate insulin secretion, insulin action, or both, it is known that diabetes manifests itself differently in each person because of each person's unique physiology that interacts with variable health and lifestyle factors such as diet, weight, stress, illness, sleep, exercise, and medication intake. Biomarkers are patient biologically derived indicators of biological or pathogenic processes, pharmacologic responses, events or conditions (e.g., aging, disease or illness risk, presence or progression, etc.). For example, a biomarker can be an objective measurement of a variable related to a disease, which may serve as an indicator or predictor of that disease. In the case of diabetes mellitus, such biomarkers include measured values for glucose, lipids, triglycerides, and the like. A biomarker can also be a set of parameters from which to infer the presence or risk of a disease, rather than a measured value of the disease itself. When properly collected and evaluated, biomarkers can provide useful information related to a medical question about the patient, as well as be used as part of a medical assessment, as a medical control, and/or for medical optimization.

For diabetes, clinicians generally treat diabetic patients according to published therapeutic guidelines such as, for example, Joslin Diabetes Center & Joslin Clinic, *Clinical Guideline for Pharmacological Management of Type 2 Diabetes* (2007) and Joslin Diabetes Center & Joslin Clinic, *Clinical Guideline for Adults with Diabetes* (2008). The guidelines may specify a desired biomarker value, e.g., a fasting blood glucose value of less than 100 mg/dl, or the clinician can specify a desired biomarker value based on the clinician's training and experience in treating patients with diabetes. However, such guidelines do not specify biomarker collection procedures for parameter adjustments to support specific therapies used in optimizing a diabetic patient's therapy. Subsequently, diabetic patients often must measure their glucose levels with little structure for collection and with little regard to lifestyle factors. Such unstructured collections of glucose levels can result in some biomarker measurements lacking interpretative context, thereby reducing the value of such measurements to clinicians and other such health care providers helping patients manage their disease.

A patient with a chronic disease may be asked by different clinicians at various times to perform a number of collections in an effort to diagnose a chronic disease or to optimize therapy. However, these requests to perform such collections according to a schedule may overlap, be repeats, run counter to each other and/or provide a burden on the patient such that the patient may avoid any further attempts to diagnose their chronic disease or to optimize therapy.

In addition, if a requesting clinician does not evaluate the patient properly to see if the schedule of requested collections is possible and/or whether parameters for the collections are suitable and/or acceptable for the patient, having useful results from such collections may be unlikely. Still further, if there has not been enough suitable data collected to complete the requested collections, such that the data collected is helpful towards addressing the medical question and/or the interests of the clinician, such a request may waste the time and effort of the clinician and the patient as well as the consumables used to perform the collections. Again, such failure may discourage the patient from seeking further therapy advice.

Moreover, prior art collection devices used in facilitating a schedule of collections provide limited guidance, if any at all, and simple reminders of a collection event. Such prior art devices typically need to be programmed manually by the either clinician or the patient, in which to govern the collection schedule. Such limited guidance and functionality provided by prior art collection devices can also further discourage the patient from seeking any future optimization of their therapy as performing another collection procedure in this manner may be viewed as being laborious by the patient, thereby leaving such optimization to simply guessing.

SUMMARY

It is against the above background that embodiments of the present invention present a system and method managing the implementation, execution, data collection, and data analysis of a prospective structured collection procedure running on a portable, hand-held collection device. Embodiments of the present invention can be implemented on various collection devices, such as a blood glucose measuring device (meter) that has the capability to accept and run thereon one or more collection procedures and associated meter-executable scripts according to the present invention. These collection procedures in one embodiment can be generated on a computer or any device capable of generating a collection procedure.

In one embodiment, a collection device for performing a structured collection procedure may include a processor communicably coupled to at least one memory. Program instructions may cause the processor to perform functions when executed by the processor. The processor can initiate a schedule of events of the structured collection procedure upon one or more entry criterions being met. The processor can segregate the at least one memory into a primary data store and a secondary data store. The processor can write structured patient data collected in accordance to the schedule of events to the secondary data store of the at least one memory. The processor can transform a relevant portion of the structured patient data into an evaluated data object. The processor can generate a data abstraction based at least in part upon the evaluated data object. The processor can link the primary data store and the secondary data store with the data abstraction.

In another embodiment, a collection device for performing a structured collection procedure may include a processor communicably coupled to at least one memory. Program instructions may cause the processor to perform functions when executed by the processor. The processor can initiate a schedule of events of the structured collection procedure upon one or more entry criterions being met. The processor can segregate the at least one memory into a primary data store and a secondary data store. The processor can write casual patient data collected by the collection device to the primary data store of the at least one memory. The processor can write structured patient data collected in accordance to the schedule of events to the secondary data store of the at least one memory. The processor can transform a relevant portion of the structured patient data into an evaluated data object. The evaluated data object can be a therapy result, a disease assessment, a therapy assessment, a therapy optimization and/or an adverse event. The processor can write automatically the evaluated data object to the secondary data store. The processor can apply an error checking algorithm to the primary data store after writing to the primary data store. The processor can apply a different error checking algorithm to the secondary data store after writing to the secondary data store. The processor can link the primary data store and the secondary data store with the evaluated data object.

In yet another embodiment, a method for managing data collected from a structured collection may include initiating a schedule of events of the structured collection procedure upon one or more entry criterions being met. At least one memory can be segregated into a primary data store and a secondary data store. Casual patient data collected by a collection device can be written to the primary data store of the at least one memory. Structured patient data collected in accordance to the schedule of events can be written to the secondary data store of the at least one memory. A relevant portion of the structured patient data may be transformed into an evaluated data object. A data abstraction based at least in part upon the evaluated data object may be generated. The primary data store and the secondary data store may be linked with the data abstraction.

These and other advantages and features of the invention disclosed herein, will be made more apparent from the description, drawings and claims that follow.

BRIEF DESCRIPTION OF THE DRAWINGS

The following detailed description of the embodiments of the present invention can be best understood when read in conjunction with the following drawings, where like structure is indicated with like reference numerals.

FIG. 3 shows a block diagram of a collection device embodiment according to the present invention.

FIG. 4 shows a depiction in tabular format of a data record embodiment created from using a structured collection on the collection device of FIG. 3 according to the present invention.

FIG. 7B conceptually illustrates one example of a predefined structured collection procedure, and a method for customizing the pre-defined structured collection procedure according to an embodiment of the present invention.

FIG. 10A depicts non-contextualized and contextualized data.

DETAILED DESCRIPTION

Figure 1:
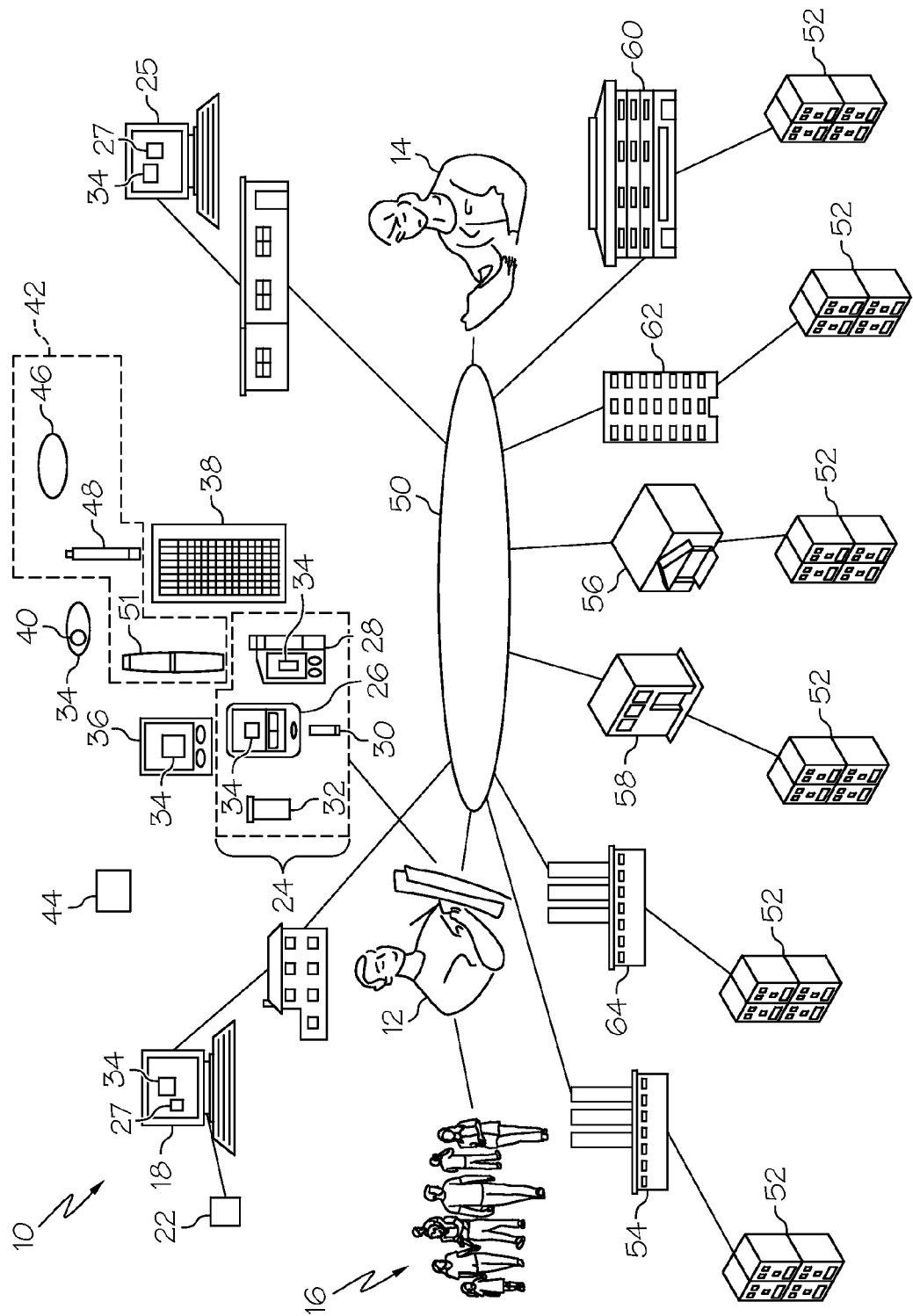
FIG. 1 is a diagram showing a chronic care management system for a diabetes patient and a clinician along with others having an interest in the chronic care management of the patient according to an embodiment of the present invention.

The present invention will be described below relative to various illustrative embodiments. Those skilled in the art will appreciate that the present invention may be implemented in a number of different applications and embodiments and is not specifically limited in its application to the particular embodiments depicted herein. In particular, the present invention will be discussed below in connection with diabetes management via sampling blood, although those of ordinary skill will recognize that the present invention could be modified to be used with other types of fluids or analytes besides glucose, and/or useful in managing other chronic diseases besides diabetes.

As used herein with the various illustrated embodiments described below, the follow terms include, but are not limited to, the following meanings.

The term "biomarker" can mean a physiological variable measured to provide data relevant to a patient such as for example, a blood glucose value, an interstitial glucose value, an HbA1c value, a heart rate measurement, a blood pressure measurement, lipids, triglycerides, cholesterol, and the like.

The term "contextualizing" can mean documenting and interrelating conditions that exists or will occur surrounding a collection of a specific biomarker measurement. Preferably, data about documenting and interrelating conditions that exists or will occur surrounding a collection of a specific biomarker are stored together with the collected biomarker data and are linked to it. In particular, a further assessment of the collected biomarker data takes into account the data about documenting and interrelating conditions so that not only the data as such are evaluated but also the link between data to which it is contextualized. The data about documenting and interrelating conditions can include for example information about the time, food and/or exercises which occurs surrounding a collection of a specific biomarker measurement and/or simultaneously thereto. For example, the context of a structured collection procedure according in an embodiment to the present invention can be documented by utilizing entry criterion for verifying a fasting state with the user before accepting a biomarker value during a Basal titration optimization focused testing procedure.

The term "contextualized biomarker data" can mean the information on the interrelated conditions in which a specific biomarker measurement was collected combined with the measured value for the specific biomarker. In particular, the biomarker data are stored together with the information on the interrelated conditions under which a specific biomarker measurement was collected and are linked thereto.

The term "criteria" can mean one or more criterions, and can be at least one or more of a guideline(s), rule(s), characteristic(s), and dimension(s) used to judge whether one or more conditions are satisfied or met to begin, accept, and/or end one or more procedural steps, actions, and/or values.

The term "adherence" can mean that a person following a structured collection procedure performs requested procedural steps appropriately. For example, the biomarker data should be measured under prescribed conditions of the structured collection procedure. If then the prescribed conditions are given for a biomarker measurement, the adherence is defined as appropriate. For examples, the prescribed conditions are time related conditions and/or exemplarily can include eating of meals, taking a fasting sample, eating a type of meal with a requested window of time, taking a fasting sample at a requested time, sleeping a minimum amount of time, and the like. The adherence can be defined as appropriate or not appropriate for a structured collection procedure or a single data point in particular of a contextualized biomarker data. Preferably, the adherence can be defined as appropriate or not appropriate by a range of a prescribed condition(s) or by a selectively determined prescribed condition(s). Moreover the adherence can be calculated as a rate of adherence describing in which extent the adherence is given for a structured collection procedure or a single data point in particular of a contextualized biomarker data.

The term "adherence event" can mean when a person executing a structured collection procedure fails to perform a procedural step. For example, if a person did not collect data when requested by the collection device, the adherence is determined as not appropriate resulting in an adherence event. In another example, adherence criteria could be a first criterion for the patient to fast 6 hours and a second criterion for collecting a fasting bG value at a requested time. In this example, if the patient provides the bG sampling at the requested time but fasted only 3 hours before providing, then although the second adherence criterion is met, the first adherence criterion is not, and hence an adherence event for the first criterion would occur.

The term "violation event" is a form of an adherence event in which the person executing the structured collection (testing) procedure (protocol) does not administer a therapeutic at a recommended time, does administer a recommended amount, or both.

The term "adherence criterion" can include adherence and can also mean a basis for comparison (e.g., assessment) of a measured value, a value related to a measured value and/or a calculated value with a defined value or defined range of the value wherein based on the comparison data are accepted with approval and positive reception. Adherence criterion can take into account time related values and/or adherence in one embodiment, but also can take into account noise in other embodiments, and the like. Furthermore, adherence criterion can be applied to contextualized biomarker data so that a biomarker data is accepted depending on a comparison of the contextualized data about documenting and interrelating conditions that exists or occurs surrounding the collection of the specific biomarker. Adherence criterion can be akin to a sanity check for a given piece of information, or group of information. In one embodiment, the single data point/information or group of data or information is rejected if the accepted criterion is not fulfilled. In particular, such rejected data are then not used for further calculations which are used to provide a therapy recommendation. Mainly the rejected data are only used to assess the adherence and/or to trigger automatically at least one further action. For example, such a triggered action prompts the user then to follow a structured collection procedure or a single requested action so that based on that action the adherence criterion can be fulfilled.

The term "data event request" can mean an inquiry for a collection of data at a single point in space-time defined by a special set of circumstances, for example, defined by time-related or not time-related events.

The term "decentralized disease status assessment" can mean a determination of the degree or extent of progression of a disease performed by using a biomarker measurement of interest to deliver a value without sending a sample to a laboratory for assessment.

The term "medical use case or question" can mean at least one or more of a procedure, situation, condition, and/or question providing an uncertainty about the factuality of existence of some medical facts, combined with a concept that is not yet verified but that if true would explain certain facts or phenomena. Medical use case or question can be already deposited and stored in the system so that the user can select between different medical use cases or questions. Alternatively, the medical use case or question can be defined by the user itself.

The terms "focused", "structured", and "episodic" are used herein interchangeably with the term "testing" and can mean a predefined sequence in which to conduct the testing.

The terms "software" and "program" may be used herein interchangeably.

FIG. 1 shows a chronic care management system 10 for a diabetes patient(s) 12 and a clinician(s) 14 along with others 16 having an interest in the chronic care management of the patient 12. Patient 12, having dysglycemia, may include persons with a metabolic syndrome, pre-diabetes, type 1 diabetes, type 2 diabetes, and gestational diabetes. The others 16 with an interest in the patient's care may include family members, friends, support groups, and religious organizations all of which can influence the patient's conformance with therapy. The patient 12 may have access to a patient computer 18, such as a home computer, which can connect to a public network 50 (wired or wireless), such as the internet, cellular network, etc., and couple to a dongle, docking station, or device reader 22 for communicating with an external portable device, such as a portable collection device 24. An example of a device reader is shown in the manual "Accu-Chek® Smart Pix Device Reader User's Manual" (2008) available from Roche Diagnostics.

The collection device 24 can be essentially any portable electronic device that can function as an acquisition mechanism for determining and storing digitally a biomarker value (s) according to a structured collection procedure, and which can function to run the structured collection procedure and the method of the present invention. Greater details regarding various illustrated embodiments of the structured collection procedure are provided hereafter in later sections. In one embodiment, the collection device 24 can be a self-monitoring blood glucose meter 26 or a continuous glucose monitor 28. An example of a blood glucose meter is the Accu-Chek® Active meter, and the Accu-Chek® Aviva meter described in the booklet "Accu-Chek® Aviva Blood Glucose Meter Owner's Booklet (2007), portions of which are disclosed in U.S. Pat. No. 6,645,368 B1 entitled "Meter and method of using the meter for determining the concentration of a component of a fluid" assigned to Roche Diagnostics Operations, Inc., which is hereby incorporated by reference. An example of a continuous glucose monitor is shown in U.S. Pat. No. 7,389, 133 "Method and device for continuous monitoring of the concentration of an analyte" (Jun. 17, 2008) assigned to Roche Diagnostics Operations, Inc., which is hereby incorporated by reference.

In addition to the collection device 24, the patient 12 can use a variety of products to manage his or her diabetes including: test strips 30 carried in a vial 32 for use in the collection device 24; software 34 which can operate on the patient computer 18, the collection device 24, a handheld computing device 36, such as a laptop computer, a personal digital assistant, and/or a mobile phone; and paper tools 38. Software 34 can be pre-loaded or provided either via a computer readable medium 40 or over the public network 50 and loaded for operation on the patient computer 18, the collection device 24, the clinician computer/office workstation 25, and the handheld computing device 36, if desired. In still other embodiments, the software 34 can also be integrated into the device reader 22 that is coupled to the computer (e.g., computers 18 or 25) for operation thereon, or accessed remotely through the public network 50, such as from a server 52.

The patient 12 can also use, for certain diabetes therapies, additional therapy devices 42 and other devices 44. Additionally, therapy devices 42 can include devices such as an ambulatory infusion pump 46, an insulin pen 48, and a lancing device 51. An example of an ambulatory insulin pump 46 include but not limited thereto the Accu-Chek® Spirit pump described in the manual "Accu-Chek® Spirit Insulin Pump System Pump User Guide" (2007) available from Roche Diabetes Care. The other devices 44 can be medical devices that provide patient data such as blood pressure, fitness devices that provide patient data such as exercise information, and elder care device that provide notification to care givers. The other devices 44 can be configured to communicate with each other according to standards planned by Continua® Health Alliance.

The clinicians 14 for diabetes are diverse and can include e.g., nurses, nurse practitioners, physicians, endocrinologists, and other such health care providers. The clinician 14 typically has access to a clinician computer 25, such as a clinician office computer, which can also be provided with the software 34. A healthcare record system 27, such as Microsoft® HealthVault™ and Google™ Health, may also be used by the patient 12 and the clinician 14 on computers 18, 25 to exchange information via the public network 50 or via other network means (LANs, WANs, VPNs, etc.), and to store information such as collection data from the collection device 24 to an electronic medical record of the patient e.g., EMR 53 (FIG. 2A) which can be provided to and from computer 18, 25 and/or server 52.

Figure 2:
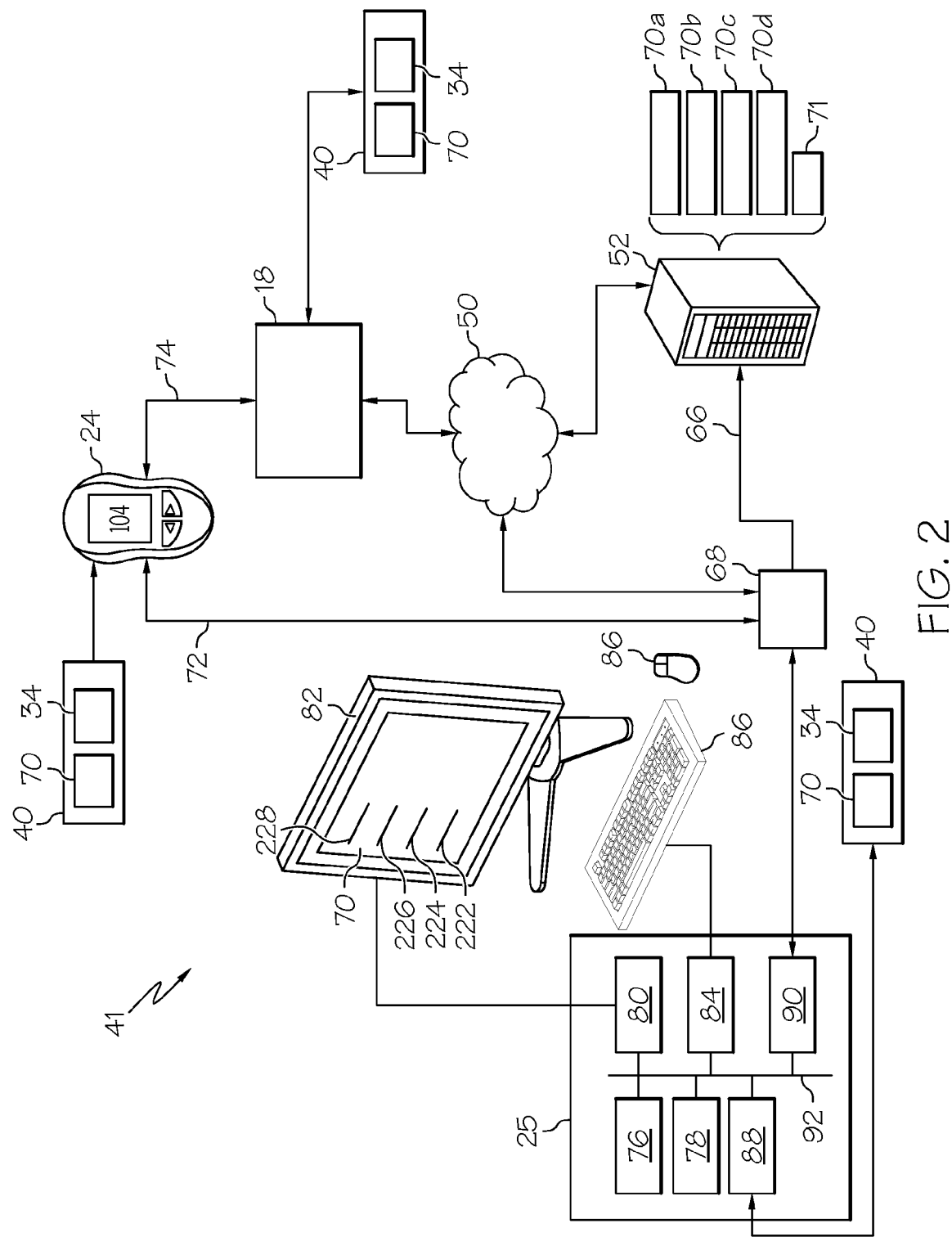
FIGS. 2 and 2A are diagrams showing embodiments of a system suitable for implementing a structured collection according to an embodiment of the present invention.

Most patients 12 and clinicians 14 can interact over the public network 50 with each other and with others having computers/servers 52. Such others can include the patient's employer 54, a third party payer 56, such as an insurance company who pays some or all of the patient's healthcare expenses, a pharmacy 58 that dispenses certain diabetic consumable items, a hospital 60, a government agency 62, which can also be a payer, and companies 64 providing healthcare products and services for detection, prevention, diagnosis and treatment of diseases. The patient 12 can also grant permissions to access the patient's electronic health record to others, such as the employer 54, the payer 56, the pharmacy 58, the hospital 60, and the government agencies 62 via the healthcare record system 27, which can reside on the clinician computer 25 and/or one or more servers 52. Reference hereafter is also made to FIG. 2.

FIG. 2 shows a system embodiment suitable for implementing a structured collection according to an embodiment of the present invention, which in another embodiment can be a part of the chronic care management system 10 and communicate with such components, via conventional wired or wireless communication means. The system 41 can include the clinician computer 25 that is in communication with a server 52 as well as the collection device 24. Communications between the clinician computer 25 and the server 52 can be facilitated via a communication link to the public network 50, to a private network 66, or combinations thereof. The private network 66 can be a local area network or a wide are network (wired or wireless) connecting to the public network 50 via a network device 68 such as a (web) server, router, modem, hub, and the likes.

In one embodiment, the server 52 can be a central repository for a plurality of structured collection procedures (or protocols) 70a, 70b, 70c, 70d, in which the details of a few exemplary structured collection procedures are provided in later sections. The server 52, as well as the network device 68, can function also as a data aggregator for completed ones of the structured collection procedures 70a, 70b, 70c, 70d. Accordingly, in such an embodiment, data of a completed collection procedure(s) from a collection device of the patient 12 can then be provided from the server 52 and/or network device 68 to the clinician computer 25 when requested in response to a retrieval for such patient data.

Figure 2A:
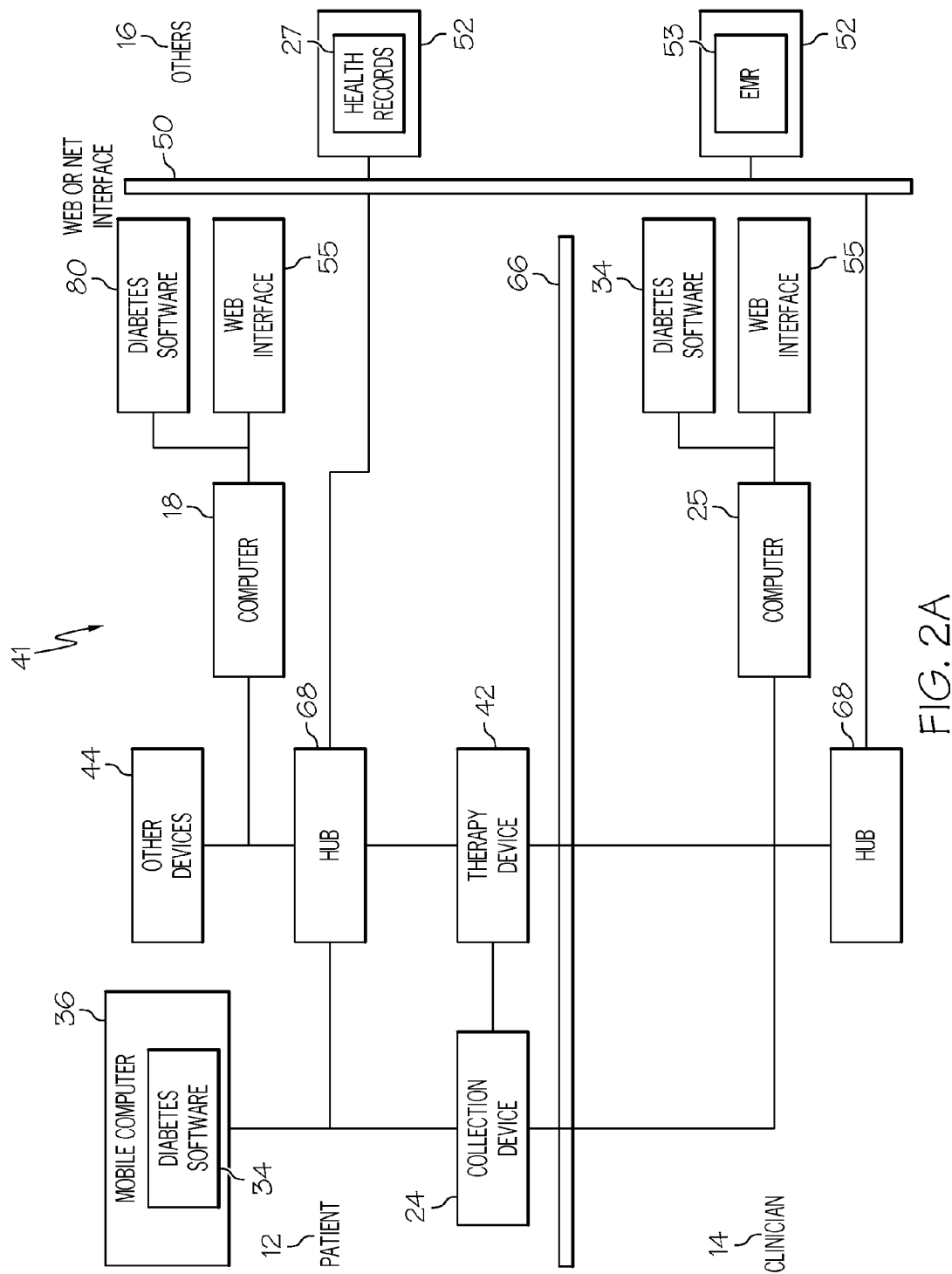

In one embodiment, one or more of the plurality of structured collection procedures 70a, 70b, 70c, 70d on the server 52 can be provided over the public network 50, such as through a secure web interface 55 (FIG. 2A, showing another embodiment of the system 41) implemented on the patient computer 18, the clinician computer 25, and/or the collection device 24. In another embodiment, the clinician computer 25 can serve as the interface (wired or wireless) 72 between the server 52 and the collection device 24. In still another embodiment, the structured collection procedures 70a, 70b, 70c, 70d, as well as software 34, may be provided on a computer readable medium 40 and loaded directed on the patient computer 18, the clinician computer 25, and/or the collection device 24. In still another embodiment, the structured collection procedures 70a, 70b, 70c, 70d may be provided pre-loaded (embedded) in memory of the collection device 24. In still other embodiments, new/updated/modified structured collection procedures 70a, 70b, 70c, 70d may be sent between the patient computer 18, the clinician computer 25, the server 52 and/or the collection device 24 via the public network 50, the private network 66, via a direct device connection (wired or wireless) 74, or combinations thereof. Accordingly, in one embodiment the external devices e.g., computer 18 and 25, can be used to establish a communication link 72, 74 between the collection device 24 and still further electronic devices such as other remote Personal Computer (PC), and/or servers such as through the public network 50, such as the Internet and/or other communication networks (e.g., LANs, WANs, VPNs, etc.), such as private network 66.

The clinician computer 25, as a conventional personal computer/workstation, can include a processor 76 which executes programs, such as software 34, and such as from memory 78 and/or computer readable medium 40. Memory 78 can include system memory (RAM, ROM, EEPROM, etc.), and storage memory, such as hard drives and/or flash memory (internal or external). The clinician computer 25 can also include a display driver 80 to interface a display 82 with the processor 76, input/output connections 84 for connecting user interface devices 86, such as a keyboard and mouse (wired or wireless), and computer readable drives 88 for portable memory and discs, such as computer readable medium 40. The clinician computer 25 can further include communication interfaces 90 for connections to the public network 50 and other devices, such as collection device 24 (wired or wireless), and a bus interface 92 for connecting the above mentioned electronic components to the processor 76. Reference hereafter is now made to FIG. 3.

FIG. 3 is a block diagram conceptually illustrating the portable collection device 24 depicted in FIG. 2. In the illustrated embodiment, the collection device 24 can include one or more microprocessors, such as processor 102, which may be a central processing unit comprising at least one more single or multi-core and cache memory, which can be connected to a bus 104, which may include data, memory, control and/or address buses. The collection device 24 can include the software 34, which provides instruction codes that causes a processor 102 of the device to implement the methods of the present invention that are discussed hereafter in later sections. The collection device 24 may include a display interface 106 for providing graphics, text, and other data from the bus 104 (or from a frame buffer not shown) for display on a display 108. The display interface 106 may be a display driver of an integrated graphics solution that utilizes a portion of main memory 110 of the collection device 24, such as random access memory (RAM) and processing from the processor 102 or may be a dedicated graphic processing unit. In another embodiment, the display interface 106 and display 108 can additionally provide a touch screen interface for providing data to the collection device 24 in a well-known manner.

Main memory 110 in one embodiment can be random access memory (RAM), and in other embodiments may include other memory such as a ROM, PROM, EPROM or EEPROM, and combinations thereof. In one embodiment, the collection device 24 can include secondary memory 112, which may include, for example, a hard disk drive 114 and/or a computer readable medium drive 116 for the computer readable medium 40, representing for example, at least one of a floppy disk drive, a magnetic tape drive, an optical disk drive, a flash memory connector (e.g., USB connector, Firewire connector, PC card slot), etc. The drive 116 reads from and/or writes to the computer readable medium 40 in a well-known manner. Computer readable medium 40, represents a floppy disk, magnetic tape, optical disk (CD or DVD), flash drive, PC card, etc. which is read by and written to by the drive 116. As will be appreciated, the computer readable medium 40 can have stored therein the software 34 and/or structured collection procedures 70a, 70b, 70c, and 70d as well as data resulting from completed collections performed according to one or more of the collection procedures 70a, 70b, 70c, and 70d.

In alternative embodiments, secondary memory 112 may include other means for allowing the software 34, the collection procedures 70a, 70b, 70c, 70d, other computer programs or other instructions to be loaded into the collection device 24. Such means may include, for example, a removable storage unit 120 and an interface connector 122. Examples of such removable storage units/interfaces can include a program cartridge and cartridge interface, a removable memory chip (e.g., ROM, PROM, EPROM, EEPROM, etc.) and associated socket, and other removable storage units 120 (e.g. hard drives) and interface connector 122 which allow software and data to be transferred from the removable storage unit 120 to the collection device 24.

The collection device 24 in one embodiment can include a communication module 124. The communication module 124 allows software (e.g., the software 34, the collection procedures 70a, 70b, 70c, and 70d) and data (e.g., data resulting from completed collections performed according to one or more of the collection procedures 70a, 70b, 70c, and 70d) to be transferred between the collection device 24 and an external device(s) 126. Examples of communication module 124 may include one or more of a modem, a network interface (such as an Ethernet card), a communications port (e.g., USB, Firewire, serial, parallel, etc.), a PC or PCMCIA slot and card, a wireless transceiver, and combinations thereof. The external device(s) 126 can be the patient computer 18, the clinician computer 25, the handheld computing devices 36, such as a laptop computer, a personal digital assistance (PDA), a mobile (cellular) phone, and/or a dongle, a docking station, or device reader 22. In such an embodiment, the external device 126 may provided and/or connect to one or more of a modem, a network interface (such as an Ethernet card), a communications port (e.g., USB, Firewire, serial, parallel, etc.), a PCMCIA slot and card, a wireless transceiver, and combinations thereof for providing communication over the public network 50 or private network 66, such as with the clinician computer 25 or server 52. Software and data transferred via communication module 124 can be in the form of wired or wireless signals 128, which may be electronic, electromagnetic, optical, or other signals capable of being sent and received by communication module 124. For example, as is known, signals 128 may be sent between communication module 124 and the external device(s) 126 using wire or cable, fiber optics, a phone line, a cellular phone link, an RF link, an infrared link, other communications channels, and combinations thereof. Specific techniques for connecting electronic devices through wired and/or wireless connections (e.g. USB and Bluetooth, respectively) are well known in the art.

In another embodiment, the collection device 24 can be used with the external device 132, such as provided as a handheld computer or a mobile phone, to perform actions such as prompt a patient to take an action, acquire a data event, and perform calculations on information. An example of a collection device combined with such an external device 126 provided as a hand held computer is disclosed in U.S. patent application Ser. No. 11/424,757 filed Jun. 16, 2006 entitled "System and method for collecting patient information from which diabetes therapy may be determined," assigned to Roche Diagnostics Operations, Inc., which is hereby incorporated by reference. Another example of a handheld computer is shown in the user guide entitled "Accu-Chek® Pocket Compass Software with Bolus Calculator User Guide" (2007) available from Roche Diagnostics.

In the illustrative embodiment, the collection device 24 can provide a measurement engine 138 for reading a biosensor 140. The biosensor 140, which in one embodiment is the disposable test strip 30 (FIG. 1), is used with the collection device 24 to receive a sample such as for example, of capillary blood, which is exposed to an enzymatic reaction and measured by electrochemistry techniques, optical techniques, or both by the measurement engine 138 to measure and provide a biomarker value, such as for example, a blood glucose level. An example of a disposable test strip and measurement engine is disclosed in U.S. Patent Pub. No. 2005/0016844 A1 "Reagent stripe for test strip" (Jan. 27, 2005), and assigned to Roche Diagnostics Operations, Inc., which is hereby incorporated by reference. In other embodiments, the measurement engine 138 and biosensor 140 can be of a type used to provide a biomarker value for other types of sampled fluids or analytes besides or in addition to glucose, heart rate, blood pressure measurement, and combinations thereof. Such an alternative embodiment is useful in embodiments where values from more then one biomarker type are requested by a structured collection procedure according to the present invention. In still another embodiment, the biosensor 140 may be a sensor with an indwelling catheter(s) or being a subcutaneous tissue fluid sampling device(s), such as when the collection device 24 is implemented as a continuous glucose monitor (CGM) in communication with an infusion device, such as pump 46 (FIG. 1). In still another embodiments, the collection device 24 can be a controller implementing the software 34 and communicating between the infusion device (e.g., ambulatory insulin pump 46 and electronic insulin pen 48) and the biosensor 140.

Data, comprising at least the information collected by the biosensor 140, is provided by the measurement engine 138 to the processor 102 which may execute a computer program stored in memory 110 to perform various calculations and processes using the data. For example, such a computer program is described by U.S. patent application Ser. No. 12/492,667, filed Jun. 26, 2009, titled "Method, System, and Computer Program Product for Providing Both an Estimated True Mean Blood Glucose Value and Estimated Glycated Hemoglobin (HbA1C) Value from Structured Spot Measurements Of Blood Glucose," and assigned to Roche Diagnostics Operations, Inc., which is hereby incorporated by reference. The data from the measurement engine 138 and the results of the calculation and processes by the processor 102 using the data is herein referred to as self-monitored data. The self-monitored data may include, but not limited thereto, the glucose values of a patient 12, the insulin dose values, the insulin types, and the parameter values used by processor 102 to calculate future glucose values, supplemental insulin doses, and carbohydrate supplement amounts as well as such values, doses, and amounts. Such data along with a date-time stamp 169 for each measured glucose value and administered insulin dose value is stored in a data file 145 of memory 110 and/or 112. An internal clock 144 of the collection device 24 can supply the current date and time to processor 102 for such use.

The collection device 24 can further provide a user interface 146, such as buttons, keys, a trackball, touchpad, touch screen, etc. for data entry, program control and navigation of selections, choices and data, making information requests, and the likes. In one embodiment, the user interface 146 can comprises one or more buttons 147, 149 for entry and navigation of the data provided in memory 110 and/or 112. In one embodiment, the user can use one or more of buttons 147, 149 to enter (document) contextualizing information, such as data related to the everyday lifestyle of the patient 12 and to acknowledge that prescribed tasks are completed. Such lifestyle data may relate to food intake, medication use, energy levels, exercise, sleep, general health conditions and overall well-being sense of the patient 12 (e.g., happy, sad, rested, stressed, tired, etc.). Such lifestyle data can be recorded into memory 110 and/or 112 of the collection device 24 as part of the self-monitored data via navigating through a selection menu displayed on display 108 using buttons 147, 149 and/or via a touch screen user interface provided by the display 108. It is to be appreciated that the user interface 146 can also be used to display on the display 108 the self monitored data or portions thereof, such as used by the processor 102 to display measured glucose levels as well as any entered data.

In one embodiment, the collection device 24 can be switched on by pressing any one of the buttons 147, 149 or any combination thereof. In another embodiment, in which the biosensor 140 is a test-strip, the collection device 24 can be automatically switched on when the test-strip is inserted into the collection device 24 for measurement by the measurement engine 138 of a glucose level in a sample of blood placed on the test-strip. In one embodiment, the collection device 24 can be switched off by holding down one of the buttons 147, 149 for a pre-defined period of time, or in another embodiment can be shut down automatically after a pre-defined period of non-use of the user interface 146.

An indicator 148 can also be connected to processor 102, and which can operate under the control of processor 102 to emit audible, tactile (vibrations), and/or visual alerts/reminders to the patient of daily times for bG measurements and events, such as for example, to take a meal, of possible future hypoglycemia, and the likes. A suitable power supply 150 is also provided to power the collection device 24 as is well known to make the device portable.

As mentioned above previously, the collection device 24 may be pre-loaded with the software 34 or by provided therewith via the computer readable medium 40 as well as received via the communication module 124 by signal 128 directly or indirectly though the external device 132 and/or network 50. When provided in the latter matter, the software 34 when received by the processor 102 of the collection device 24 is stored in main memory 110 (as illustrated) and/or secondary memory 112. The software 34 contains instructions, when executed by the processor 102, enables the processor to perform the features/functions of the present invention as discussed herein in later sections. In another embodiment, the software 34 may be stored in the computer readable medium 40 and loaded by the processor 102 into cache memory to cause the processor 102 to perform the features/functions of the invention as described herein. In another embodiment, the software 34 is implemented primarily in hardware logic using, for example, hardware components such as application specific integrated circuits (ASICs). Implementation of the hardware state machine to perform the feature/functions described herein will be apparent to persons skilled in the relevant art(s). In yet another embodiment, the invention is implemented using a combination of both hardware and software.

In an example software embodiment of the invention, the methods described hereafter can be implemented in the C++ programming language, but could be implemented in other programs such as, but not limited to, Visual Basic, C, C#, Java or other programs available to those skilled in the art. In still other embodiment, the program 34 may be implemented using a script language or other proprietary interpretable language used in conjunction with an interpreter. Reference hereafter is also made to FIG. 4.

FIG. 4 depicts in tabular form a data file 145 containing data records 152 of self-monitored data 154 resulting from a structured collection procedure according to an embodiment of the present invention. The data records 152 (e.g., rows) along with the self-monitoring data 154 (e.g., various one of the columns) can also provide associated therewith contextual information 156 (e.g., other various ones of the columns as well as via row and column header information). Such contextual information 156 can be collected either automatically, such as for example via input received automatically from the measurement engine, the biosensor, and/or any one of the other devices, or via input received from the user interface which was manually enter by the patient in response to a collection request (e.g., a question displayed by the processor 102 on the display 108) during the structured collection procedure. Accordingly, as such contextual information 156 can be provided with each data record 152 in one embodiment, such information is readily available to a physician and no further collection of such information is necessarily needed to be provided again by the patient either manually or orally after completing the structured collection procedure. In another embodiment, if such contextual information 156 and/or additional contextual information is collected after completion of a structured collection procedure according to the present invention, such information may be provided in the associated data file 145 and/or record 152 at a later time such as via one of the computers 18, 25. Such information would then be associated with the self-monitored data in the data file 145, and thus would not need to be provided again orally or manually. Such a process in the latter embodiment may be needed in the situation where the structured collection procedure is implemented as or partly as a paper tool 38 which is used with a collection device incapable of running the software 34 implementing such a structured collection procedure.

It is to be appreciated that the date file 145 (or portions thereof, such as only the self-monitored data 154) can be sent/downloaded (wired or wireless) from the collection device 24 via the communication module 124 to another electronic device, such the external device 132 (PC, PDA, or cellular telephone), or via the network 50 to the clinician computer 25. Clinicians can use diabetes software provided on the clinician computer 25 to evaluate the received self-monitored data 154 as well as the contextual information 156 of the patient 12 for therapy results. An example of some of the functions which may be incorporated into the diabetes software and which is configured for a personal computer is the Accu-Chek® 360 Diabetes Management System available from Roche Diagnostics that is disclosed in U.S. patent application Ser. No. 11/999,968 filed Dec. 7, 2007, titled "METHOD AND SYSTEM FOR SETTING TIME BLOCK," and assigned to Roche Diagnostics Operations, Inc., which is hereby incorporated by reference.

In one embodiment, the collection device 24 can be provided as portable blood glucose meter, which is used by the patient 12 for recording self-monitored data comprising insulin dosage readings and spot measured glucose levels. Examples of such bG meters as mentioned above previously include but are not limited to, the Accu-Chek® Active meter and the Accu-Chek® Aviva system both by Roche Diagnostics, Inc. which are compatible with the Accu-Chek® 360° Diabetes management software to download test results to a personal computer or the Accu-Chek® Pocket Compass Software for downloading and communication with a PDA. Accordingly, it is to be appreciated that the collection device 24 can include the software and hardware necessary to process, analyze and interpret the self monitored data in accordance with predefined flow sequences (as described below in detail) and generate an appropriate data interpretation output. In one embodiment, the results of the data analysis and interpretation performed upon the stored patient data by the collection device 24 can be displayed in the form of a report, trend-monitoring graphs, and charts to help patients manage their physiological condition and support patient-doctor communications. In other embodiments, the bG data from the collection device 24 may be used to generated reports (hardcopy or electronic) via the external device 132 and/or the patient computer 18 and/or the clinician computer 25.

The collection device 24 can further provide the user and/or his or her clinician with at least one or more of the possibilities comprising: a) editing data descriptions, e.g. the title and description of a record; b) saving records at a specified location, in particular in user-definable directories as described above; c) recalling records for display; d) searching records according to different criteria (date, time, title, description etc.); e) sorting records according to different criteria (e.g., values of the bG level, date, time, duration, title, description, etc.); f) deleting records; g) exporting records; and/or h) performing data comparisons, modifying records, excluding records as is well known.

As used herein, lifestyle can be described in general as a pattern in an individual's habits such as meals, exercise, and work schedule. The individual additionally may be on medications such as insulin therapy or orals that they are required to take in a periodic fashion. Influence of such action on glucose is implicitly considered by the present invention.

It is to be appreciated that the processor 102 of the collection device 24 can implement one or more structured collection procedures 70 provided in memory 110 and/or 112. Each structured collection procedure 70 in one embodiment can be stand-alone software, thereby providing the necessary program instructions which when executed by the processor 102 causes the processor to perform the structure collection procedure 70 as well as other prescribed functions. In other embodiments, each structured collection procedure 70 can be part of the software 34, and can be then be selectively executed by the processor 102 either via receiving a selection from a menu list provided in the display 108 from the user interface 146 in one embodiment or via activation of a particular user interface, such as a structured collection procedure run mode button (not shown) provided to the collection device 24 in another embodiment. It is to be appreciated that the software 34, likewise, provides the necessary program instructions which when executed by the processor 102 causes the processor to perform the structure collection procedure 70 as well as other prescribed functions of the software 34 discussed herein. One suitable example of having a selectable structured collection procedure provided as a selectable mode of a collection meter is disclosed by in U.S. patent application Ser. No. 12/491,523, filed Jun. 25, 2009, titled "Episodic Blood Glucose Monitoring System With An Interactive Graphical User Interface And Methods Thereof," assigned to Roche Diagnostics Operations, Inc., which is hereby incorporated by reference.

In still another embodiment, a command instruction can be sent from the clinician computer 25 and received by the processor 102 via the communication module 124, which places the collection device 24 in a collection mode which runs automatically the structured collection procedure 70. Such a command instruction may specify which of the one or more structured collection procedures to run and/or provide a structured collection procedure to run. In still another embodiment, a list of defined medical use cases or medical questions can be presented on the display 108 by the processor 102, and a particular structured collection procedure 70 can be automatically chosen by the processor 102 from a plurality of structured collection procedures (e.g., procedures 70a, 70b, 70c, and 70d) depending on the selection of the defined medical use cases or medical questions received by the processor 102 via the user interface 146.

In still another embodiment, after selection, the structured collection procedure(s) 70 can be provided through the computer readable medium e.g., 40 and loaded by the collection device 24, downloaded from computer 18 or 25, the other device(s) 132, or server 52. Server 52, for example, may be a healthcare provider or company providing such pre-defined structured collection procedures 70 for downloading according to a selected defined medical use case or question. It is to be appreciated that the structured collection procedure(s) 70 may be developed by a healthcare company (e.g. company 64) and implemented via the public network 50 through a webpage and/or made available for downloading on server 52, such as illustrated in FIG. 2. In still other embodiments, notices that a new structured collection procedure 70 is available for use on the collection device 24 to help address a particular use case/medical question that a user (e.g., healthcare provider and patient) may have can be provided in any standard fashion, such for via postal letters/cards, email, text messaging, tweets, and the likes.

In some embodiments, as mentioned above previously, a paper tool 38 can perform some of the functions provided by the diabetes software 34. An example of some of the functions which may be incorporated into the diabetes software 34 and which is configured as a paper tool 38 is the Accu-Chek® 360 View Blood Glucose Analysis System paper form available from Roche Diagnostics also disclosed in U.S. patent application Ser. No. 12/040,458 filed Feb. 29, 2007 entitled "Device and method for assessing blood glucose control," assigned to Roche Diagnostic Operations, Inc., which is hereby incorporated by reference.

In still another embodiment, the software 34 can be implemented on the continuous glucose monitor 28 (FIG. 1). In this manner, the continuous glucose monitor 28 can be used to obtain time-resolved data. Such time-resolved data can be useful to identify fluctuations and trends that would otherwise go unnoticed with spot monitoring of blood glucose levels and standard HbA1c tests. Such as, for example, low overnight glucose levels, high blood glucose levels between meals, and early morning spikes in blood glucose levels as well as how diet and physical activity affect blood glucose along with the effect of therapy changes.

In addition to collection device 24 and software 34, clinicians 14 can prescribe other diabetes therapy devices for patients 12 such as an ambulatory insulin pump 46 as well as electronically based insulin pen 48 (FIG. 1). The insulin pump 46 typically includes configuration software such as that disclosed in the manual "Accu-Chek® Insulin Pump Configuration Software" also available from Disetronic Medical Systems AG. The insulin pump 46 can record and provide insulin dosage and other information, as well as the electronically based insulin pen 48, to a computer, and thus can be used as another means for providing biomarker data as requested by the structured collection procedure 70 (FIG. 2) according to the present invention.

It is to be appreciated that, and as mentioned above previously, one or more of the method steps discussed hereafter can be configured as a paper tool 38 (FIG. 1), but preferably all the method steps are facilitated electronically on system 41 (FIG. 2) or on any electronic device/computer, such as collection device 24, having a processor and memory as a program(s) residing in memory. As is known, when a computer executes the program, instructions codes of the program cause the processor of the computer to perform the method steps associated therewith. In still other embodiments, some or all of the method steps discussed hereafter can be configured on computer readable medium 40 storing instruction codes of a program that, when executed by a computer, cause the processor of the computer to perform the method steps associated therewith. These method steps are now discussed in greater detail hereafter with reference made to FIGS. 5A and 5B.

Create a Structured Collection Procedure

Figure 5A:
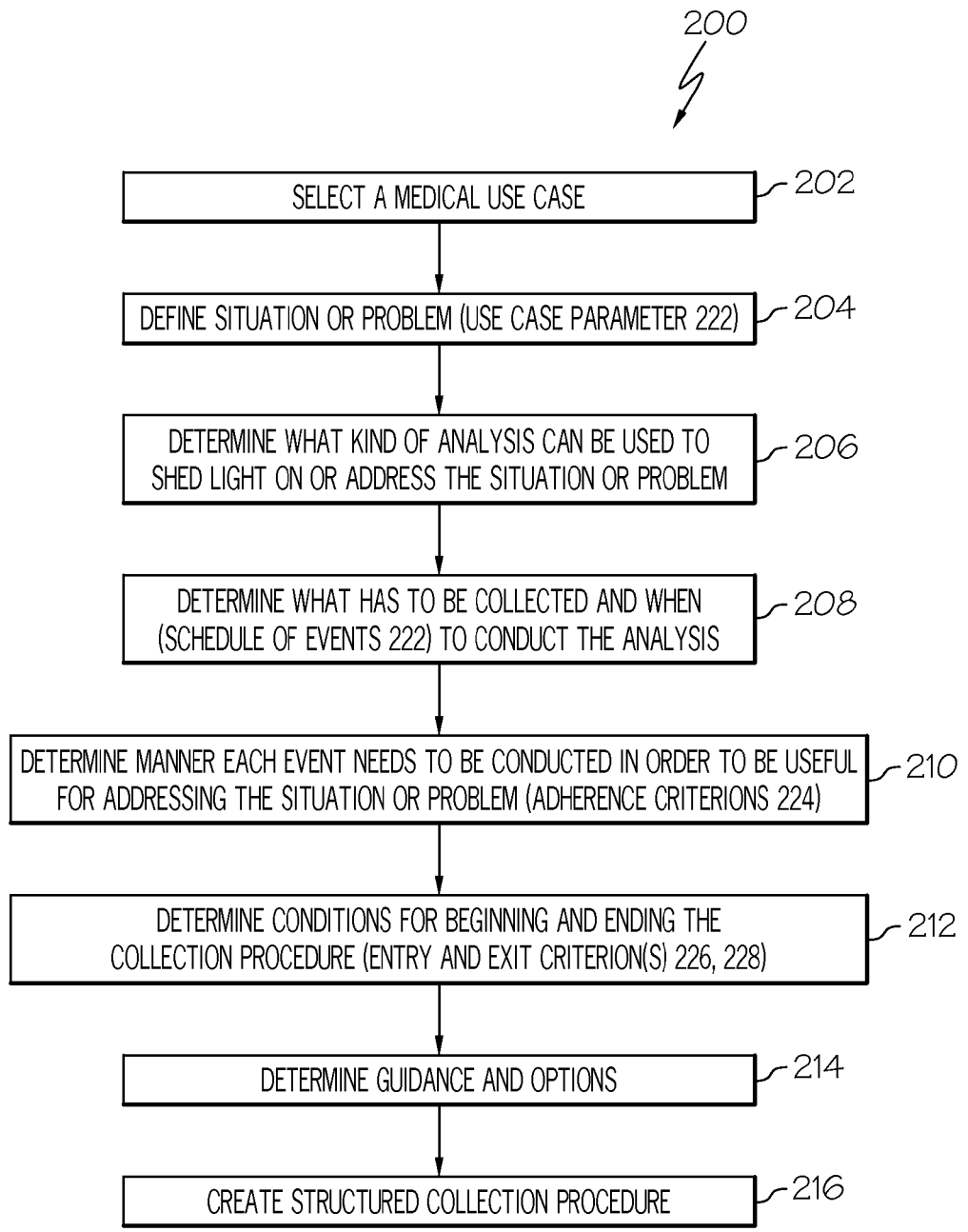
FIG. 5A depicts a method of creating a structured collection procedure for a medical use case and/or question according to an embodiment of the present invention.
Figure 5B:
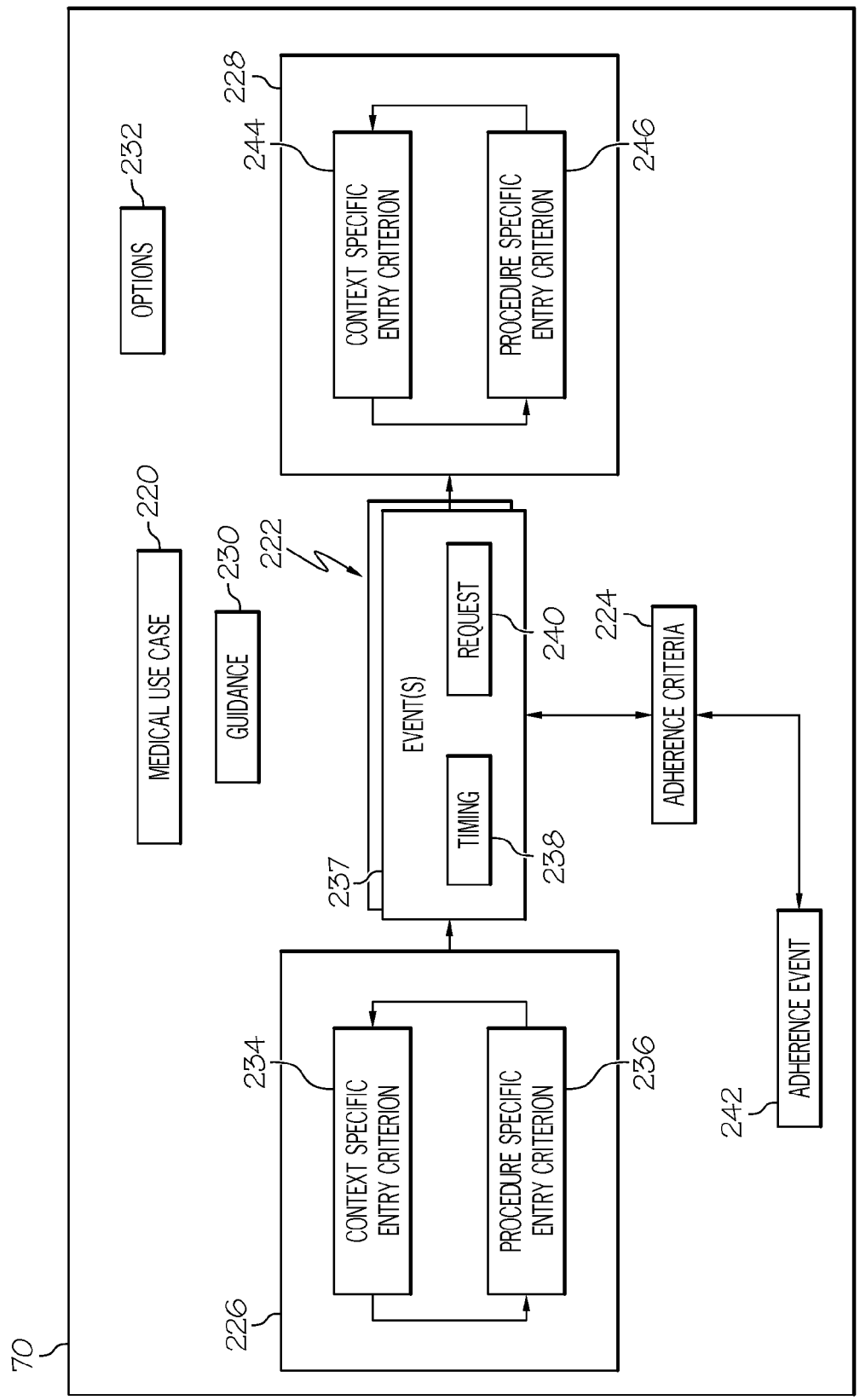
FIGS. 5B and 5C show parameters defining a structured collection procedure and factors which can be considered to optimize a patient's therapy using the structured collection procedure, respectively, according to one or more embodiments of the present invention.

FIG. 5A depicts a method 200 of creating a structured collection procedure 70 illustrated by FIG. 5B for a medical use case or question which may be implemented in any one of the above described devices 18, 24, 25, 26, 28, 36, 52 as stand alone software, as part of the diabetes software 34 or portions there of as part of paper tool 38. In step 202, a medical use case or question, hereafter referred to generally as use case(s), is selected and/or can be defined. It is to be appreciated that a use case may be, for example, one selected from the following medical use cases or questions: a desire to know the effects of eating a particular food; a desire to know the best time to take medication before and/or after with a meal; and a desire to know the effects of exercise on bG levels. Other use cases may be questions concerning finding a diagnosis, how best to initialize therapy for a patient, finding a determination of status of a patient disease progression, finding the best ways to optimize a patient therapy, and the like. Still other examples can be providing such structured collection procedures 70 which can be used to help address medical questions regarding fasting blood glucose, pre-prandial glucose values, postprandial glucose values, and the like. Other medical questions can be to control the biomarker in a predefined context, to optimize the biomarker in a predefined context, related to therapy onset, type of therapy, oral mono-therapy, oral combination therapy, insulin therapy, lifestyle therapy, adherence to therapy, therapy efficacy, insulin injection or inhalation, type of insulin, split of insulin in basal and bolus, and the likes. For example, medical questions regarding oral monotherapy and oral combination could include those involving sulfonylureas, biguanides, thiazolidinediones, alpha-glucosidase inhibitors, meglitinides, dipeptidyl peptidase IV inhibitors, GLP-1 analogs, taspoglutide, PPAR dual alpha/gamma agonists, aleglitazar. The selected use case can be assigned to a medical use case parameter 220 depicted in FIG. 5B.

Figure 5C:
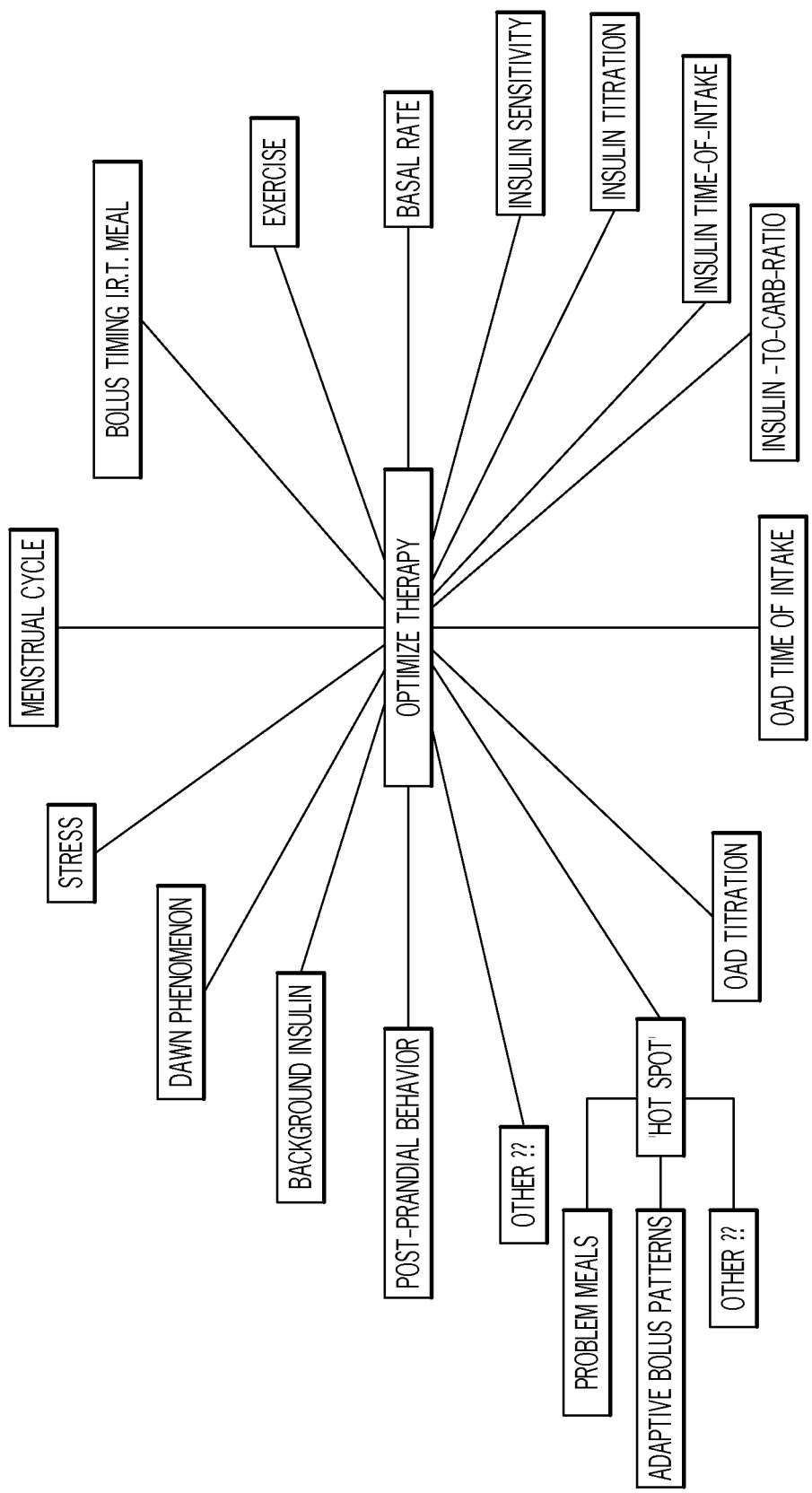

In step 204, the situation or problem surrounding the selected use case can be defined. This can be accomplished via looking at all the factors which may affect a change in the use case. For example, in the use case of desiring to know how best to optimize a patient's therapy some factors to look at may include stress, menstrual cycle, pre-dawn effect, background insulin, exercise, bolus timing with respect to a meal, basal rate, insulin sensitivity, post-prandial behavior, and the like such as shown by FIG. 5C.

In step 206, a determination can be made as to what kinds of analysis can be used to address or shed light on the situation or the problem. Such analysis may be, for example, selected from the following: evaluating the change in fasting blood glucose (FPG) values over the course of the collection procedure 70, monitoring one or more particular value over the duration of the collection procedure 70, determining an insulin to carbohydrate (I:C) ratio, determining insulin sensitivity, determining best time for administering a drug with respect to another variable, such as meal(s), and the like. In step 208, a sampling group determination can be made as to which information has to be collected, such as what biomarker(s) and the context(s) in which the biomarkers shall be collected, as well as when this information needs to be collected to conduct the analysis. For example, the sampling group can be defined as a string of data objects, each of which consists of: target type, e.g., time based which can use a target time (e.g., used for an alerting feature), a lower time window bound, an upper time window bound, etc., or data based which defines a data type (single, aggregate, or formula), the conditions for accepting the data (e.g., none, below a value, above a value, a formula, etc.), the type of collection (e.g., user input, sensor, data, etc.), as well as any reminder screen text (e.g., static, and/or dynamic in both formatting and value insertion) for each collection. The result of this process is a schedule of collection events 222 (FIG. 5B). Next in step 210, the manner in which each or a group of the schedule of collection events 222 is/are to be conducted in order to be useful for addressing the situation or problem of the selected use case is then determined. This results in one or more adherence criterions 224. In addition to and/or instead of the manner for performing a collection, the adherence criterion(s) 224 may also be based on one or more biomarker values falling into a pre-defined range or is equal to a certain pre-defined value. In other embodiments, the adherence criterion(s) can be a formula (s) which uses a biomarker datum or group of such data to determine if the resulting value falls into the pre-defined range or is equal to a certain pre-defined value.

For example, adherence criteria 224 can describe the parameters around the events 237 that the patient 12 needs to perform such as tests within a certain window, fasting for a given amount of time, sleeping for a given amount of time, exercise, low stress, not menstruating, etc. As such, an adherence criterion 224 can establish the context of the information about to be provided. Adherence criteria 224 can also be used as mentioned above previously in another context to provide an assessment of whether the data is acceptable, and when used in such a context may be referenced to as "acceptance" criteria. For example, before a sample is taken, the adherence criteria 224 can establish whether steps leading up to taking of the sample are accomplished. For example, the processor 102 in response to a request 240 displays the question, "Have you been fasting for the last 8 hours?", wherein a "Yes" response received by the processor via the user interface 146 meets the adherence criterion 224 for this step. In another example, after the sample is taken, the processor 102 can assess the received data for reasonableness using other adherence (acceptance) criterion(s). For example, based on prior data, a fasting bG sample should be between 120-180 mg/dl, but the received value was of 340 mg/dl, and thus fails such adherence (acceptance) criteria since being out of the predefined range for an acceptable value. In such an example, an adherence event 242 occurs wherein the processor 102 could prompt for an additional sample. In such a case, if the re-sampling fails too (i.e., not between 120-180 mg/dl), the assessment provided by the processor 102 is that the patient 12 has not fasted, and thus the processor 102 as instructed by the adherence criterion upon a failing of the re-sampling extend automatically the events 237 in the schedule of events 222 accordingly.

Next in step 212, the condition(s) and context(s) in which the schedule of events 222 is to be started and ended can be determined. This results in one or more entry criterions 226 and exit criterions 228 being provided for the schedule of events 222 as well as possibly for a group of other schedule of events to which the schedule of events 222 belongs if providing a package of structured collection procedures, e.g., procedures 70a, 70b, 70c, and 70d, which may run concurrently and/or sequentially one after the other.

For example, the one or more entry criterions 226 can be used to determine whether the patient meets the conditions to use the collection procedure by the processor 102 checking that, for example, the patient 12 meets the entry criterion 226 based on current age being in a range, HbA1c being in a range, that the patient has a particular disease, has had the disease over a minimum period of time, has a Body Mass Index (BMI) in a range, had a Fasting Plasma Glucose (FPG) in a range, had a particular drug sensitivity, is taking a particular drug, taking a particular drug dosage, meets one or more prerequisites of another structured collection procedure, has completed one or more of another structured collection procedure, does not have one or more particular pre-conditions, e.g., pregnant, not fasting, or contraindications, e.g., feeling ill, feverish, vomiting, etc., and combinations thereof. Entry criterion 226 can also initiate the schedule of events 222 by an initiation event such as a time of day, a time of week, meal, taking a meal with a time offset, exercise, and exercise with a time offset, use of a therapeutic drug, use of a therapeutic drug with time offset, physiological circumstances, biomarker range, and biomarker within a predetermined range calculated as an offset from a prior biomarker value. Example of a physiological circumstance can be that entry criterion will be met to start a structured collection procedure when a pre-determined number of a physiological event, e.g., hyperglycemia, hypoglycemia, a certain temperature at a certain of day, and the like, occur within a pre-defined amount of time, e.g., hours, day, weeks, etc. Accordingly, the entry criterion can be used to support the use of need to met prerequisites, indications for usage, and/or contraindications for usage. For example, an entry criterion 226 could define a prerequisite condition which in order for the structure collection procedure 70 to run an Insulin Sensitivity optimization, the processor 102 must verify first that a structured collection procedure for a Basal titration is completed and/or has a desired result and/or as well as another structured collection procedure for an insulin to carbohydrate ratio is completed and/or has a desired result. In another example, an entry criterion 226 could define a condition which needs to meet certain indications for usage in which certain structured collection procedures could provide segregated uses for diabetics who are Type 1 vs. Type 2 as well as types of structure collection procedures which can be used to titrate for specific drugs. In another example, the entry criterion 226 could define a condition which needs to meet certain contraindications for usage, in which for example, certain structured collection procedures 70 will not run if the patient 12 is pregnant, sick, etc.

Examples of the one or more exit criterions 228 can be based on the processor 102 determining that a particular value is reached, that a mean average of the primary samples values are in a range, that a particular event(s) and/or condition(s) have or have not occurred, and combinations thereof. Other conditions when the procedure may stop can include adverse events such as a hypoglycemic event, the patient is sick, the patient undergoes a therapy change, etc. Additional detail may also by provided by the processor 102 on the display 108 to the patient 12 based on what the specific exit criterion has been met. For example, in one example, if the patient 12 measures a glucose value indicating hypoglycemia, upon exiting the procedure, the processor 102 run automatically another alternative procedure which instructs the patient 12 to ingest carbohydrates and measure his blood glucose value every half an hour until the blood glucose exceeds 120 mg/dL. For this alternative procedure, the patient 12 can also be requested by the processor 102 to document his meals, activity, stress, and other relevant details to ensure that the conditions that led to hypoglycemia are recorded. The patient 12 may also be instructed by the processor 102 to contact the clinician 14 in this and other such special cases as deemed fit. Exit criteria can also include, for example, criterion for ending such as exiting after a successful completion, or exiting after an indeterminate completion, such as expiration of a predetermined timeout (logistical end), e.g., no result after n days, where n=1 to 365 days, or by termination e.g., exit with unsuccessful termination due to a fail-safe. It is to be appreciated that the structured collection procedure 70 can also be defined to end automatically not only based on meeting the exit criterion 228, but also when the patient 12 fails to perform a request to an acceptable level of compliance and/or when a patient physiological state has changed such that the patient is should not carry out the schedule of events 222, thereby failing adherence criteria 224, wherein the adherence event 242 is to end the structured collection procedure.

In step 214, guidance 230 for the user during collection can be determined as well as any options 232 for customizing the collection. For example, for guidance 230, the clinician 14 can use a default list of messages, or tailor messages to guide the patient 12 during execution of the collection procedure 70. As an example, one message could be provided on a successful data acquisition (i.e., meets the adherence criteria 224) would read, "Thank you. Your next scheduled measurement is at 1230 pm." Alarms, such as provided by indicator 148, can also be associated with the collection procedure 70 that remind the patient 12 to take a measurement and can include a snooze functionality should the patient 12 need additional time to conduct the measurement. The snooze functionality as well as other device features are discussed further in later sections.

The result of steps 208-214 is the structured collection procedure 70 being created in step 216 which associates together the use case parameter 220, the scheduled of events 222, the adherence criterion(s) 224, the entry criterion(s) 226, the exit criterion(s) 228, guidance 230, and the options 232. In one embodiment, at the time of generating a collection procedure 70, the clinician 14 also generates printed material that explains to the patient the following aspects (at a minimum): the purpose of the collection procedure 70 and expected ideal outcome, i.e., setting a goal for the collection procedure 70; the collection procedure 70 design and the number of measurements needed; the entry criteria 226 that the patient 12 must satisfy before initiating the collection procedure 70 and before taking each reading; and the exit criteria 228 under which the patient 12 should cease to continue the collection procedure 70. Such printed material as well as the guidance 230 that can be provided during the execution of the collection procedure 70 ensures that the patient is fully aware of why the data collection procedure is being carried out.

Examples of the structured collection procedure 70 may be, for example, a structured collection procedure for determining an insulin-to-carbohydrate ratio, for determining bolus timing in respect to meal start, and for determining an exercise equivalent to ingested carbohydrates. In step 218, the structured collection procedure 70 is then made available for implementation and use in the system 41, such as in any of the above discussed manners mentioned with regards to FIGS. 1, 2, and 3. A structured collection procedure 70 accordingly may be provided via the above process, such as by either the medical community or healthcare companies 64, to help the clinician 14 address and/or investigate a defined medical use case or problem.

FIG. 5B shows the interactions of the parameters 222, 224, 226, and 228 of the structured collection procedure 70 for obtaining contextualized biomarker data from a diabetic patient to address a medical use case upon which the structured collection procedure is based. As mentioned above, the use case parameter 220 may be provided to identify the medical use case or question to which the parameters 222, 224, 226, and 228 address. For example, the processor 76 of the clinician computer 25, the processor 102 of the collection device 24, and/or the server 52 may read the medical use case parameters 220 from a plurality of structured collection procedures 70a, 70b, 70c, 70d (FIG. 2), such as provided on these devices and/or within the system 41, and provide a list of the available structured collection procedures, such as on the display 82 of the clinician computer 25 or the display 108 of the collection device 24. Additionally, the clinician computer 25, the patient computer 18, and/or the server 52 can use the medical use case parameter 220 for locating/sorting/filtering such structured collection procedures according to a medical use case(s).

As mentioned above, the entry criterion(s) 226 establishes the requirements for initiating the structured collection procedure 70 to obtain patient data which includes biomarker data, particularly, collected in a predefined context. In one embodiment, the processor 102 of the collection device 24 can use the entry criterion(s) 226 to determine when an associated structured collection procedure 70 is appropriate for the patient's physiological context and to ensure that all of the necessary inputs to the associated structured collection procedure have been established. Therefore, it is to be appreciated that the start date and/time of a structured collection procedure may dynamically change automatically by the processor 102 of the collection device 24 if the predefined condition(s) of the entry criterion(s) 226 is not satisfied. Accordingly, until the entry criterion 226 is satisfied, the start date and/time of the associated structured collection procedure 70 can be at some unknown time in the future.

For example, in one embodiment, a structured collection procedure 70 can be chosen automatically by the processor 102 from a plurality of structured collection procedures 70a, 70b, 70c, 70d, such as provided in memory 110 of the collection device 24, memory of the computer 18, 25 and/or from server 52, based on satisfying the condition(s) of a defined entry criterion 226 for an associated structured collection procedure. For example, in one embodiment, a first structured collection procedure, such as procedure 70d, is useful for showing trends in blood glucose levels ("bG Level Trending"). Therefore, an entry criterion 226 for the first structured collection procedure 70d may be for the patient to have a bG level mean which has elevated over a defined period (e.g., a past number of days, weeks, and months from the current date) above a certain pre-defined rate. For a second structured collection procedure, such as procedure 70a, its entry criteria 226 may require a particular number of bG measurement for a pre-breakfast measurement over a defined period (e.g., a past number of days, weeks, months, from the current date) being below a pre-defined bG value. In such an example, the processor 102 upon start up in one embodiment when commanded, such as via input received via the user interface in another embodiment, or at a scheduled time as programmed by the software 34 in still another embodiment, can run through the various entry criteria 226 provided by the various structured collection procedures 70a and 70d that are, for example, provided in memory 110 of the collection device 24 and determine whether the stated condition(s) for the entry criteria 226 of a particular structured collection procedure 70 is satisfied. In this example, the processor 102 determines that the historical data from past measurements in memory 110 indicate that the patient's bG level mean has been elevating, and that the entry criterion 226 for the first collection procedure 70d has been met, but not the entry criteria for the second collection procedure 70a. In this example, the processor 102 then automatically selects and starts the first structured collection procedure 70d based on the above-mentioned analysis.

It is also to be appreciated that the use of the entry criterion 226 can help to reduce the misallocation of medical expenses by assuring that the indications of use for the structured collection procedure 70 have been met before starting the schedule of collection events 222. The entry criterion 226 as well can help assure that any requests to perform multiple structured collection procedures do not overlap if incompatible, are not unnecessary repeats of each other, or provide a significant burden on the patient. In this manner, many of the noted problems in which a patient may avoid any further attempts to diagnose their chronic disease or to optimize therapy can be both addressed and avoided automatically by the processor 102 of the collection device 24 via use of the entry criterion 226.

As shown by FIG. 5B, the entry criteria 226 can include context specific entry criterion 234, procedure specific entry criterion 236, and combination thereof. Examples of context specific entry criterion 234 can include one or more variables to identify meals, low blood glucose events, insulin type and dosage, stress, and the like. In another example, the context specific entry criterion 234 can be defined such as in the form of a specific question(s), to which the processor 102 requires a specific answer to be received from patient via input from the user interface 146. For example, the processor 102 in executing the entry criterion 226 may display on the display 108 the question of whether the patient is willing and able to perform the structured collection procedure 70 over the required period. If the patient responses affirmatively via the user interface 146, then the entry criterion 226 has been satisfied and the processor 102 continues automatically with performing the collection events 237 according to the their associated timing as defined in the structured collection procedure 70. If the patient responses in the negative to the displayed question, then the processor 102 will not continue with the structured collection procedure 70, and may for example, re-schedule the asking of such a question to a future time, such as if designated by an options parameter.

Examples of procedure specific entry criterion 236 can include one or more variables to identify disease state, disease status, selected therapy, parameter prerequisites, insulin to carbohydrate ratio prior to testing insulin sensitivity, incompatible collection procedures, and the like. The procedure specific entry criterion 236 can be defined such that the processor 102 will continue automatically with the structured collection procedure 70 with one of three initiators—the patient 12, the clinician 14, or data, e.g., if the condition(s) of the entry criterion 226 is satisfied. For example, the procedure specific entry criterion 236 can be satisfy if the clinician 14 has prescribed the structured collection procedure 70, such as via an authorized user entering via the user interface 146 a valid password to unlock the particular structured collection procedure for use, in one embodiment. In another embodiment, the clinician 14 can send the password or an authorization code from clinician computer 25 and/or server 52 to the collection device 24 which prescribes (authorizes) the collection procedure 70 for use by the patient 12 on the collection device 24. It is to be appreciated that one or more structured collection procedure 70 can be provided in memory 110 of the collection device 24 which cannot be used by the patient 12, and which can be also hidden from being viewed on the display 108, such as in a selection list, by the patient until authorized by the clinician 14.

The procedure specific entry criterion 236 can be satisfy by a user for example, by the user selecting a particular structured collection procedure 70 from a listing of structured collection procedures 70a, 70b, 70c, 70d provided on the display 108. An example of a data initiated procedure for criterion 236 would be that a biomarker measurement(s) provided to the processor 102 indicates a certain condition which must have occurred or be present in order for the entry criteria 226 for the particular structured collection procedure to be satisfied. Such a condition, for example, can be the occurrence of a single event, such as a severe hypoglycemic event, or a series of events, such as hypoglycemic events within a given, a predetermined time frame, such as in 24 hours from a start time, in one week from a start time, etc, a calendar date-time, and the like.

Accordingly, the entry criteria 226 can be a single criterion or multiple criteria that establish context and/or condition of the patient's physiology that are relevant to the medical use case being addressed by the structured collection procedure 70. In another embodiment, the entry criteria 226 can be assessed after patient data has been collected, such as, on historical patient data.

The schedule of events 222 specifies one or more events 237 which each comprises at least one or more variables defining a performance time 238, the guidance 230 to perform the event, requests 240 for patient actions, which may include a request for information from the patient and/or a request for collection of at least one type of biomarker data from the patient, and combinations thereof. For performance time 238, the schedule of events 222 can specify timing of each event 237, such as for a biomarker sampling at a particular time on three consecutive work days, or one sample at time of wake-up, one sample thirty minutes later, and another sample one hour later.

The guidance 230 for each event 237 and for any criteria 224, 226, 228 may include, for example, providing electronic reminders (acoustic, visual) to start, end and/or wake up at a particular time, to perform a bG collection at a particular time, to ingest a particular meal or food(s) at a particular time, to perform a certain exercise(s) at a particular time, take medication at a particular time, and the like. Guidance 230 may also include information, questions and requests to record particular information about physiology, health, sense of well-being, etc., at a particular time, suggestion to improve compliancy with the collection procedure, encouragement, and positive/negative feedback.

It is to be appreciated that the events 237 define all the steps that are necessary to be preformed in advance of as well as after a biomarker sampling according to a request 240, such that a reproducible set of circumstances, i.e., context before and/or after the sampling, is created in the biomarker data for the biomarker sampling. Examples of such biomarker data, in the context of diabetes, include fasting blood glucose values, pre-prandial glucose values, postprandial glucose values, and the like. Examples of a set of circumstances can include data associated with the biomarker value which identifies collected information in the patient data about meals, exercises, therapeutic administration, sleep, hydration, and the likes.

Each of the events 237 in the schedule of events 222 can be time-based, event-based, or both. An event 237 can also be a start of a meal, a wake-up time, start of exercise, a therapeutic administration time, a relative offset used with a prior glucose value, or a time indicating movement above or below a predetermined biomarker value threshold. The events 237 can also include any required patient actions necessary to be performed in advance of and during biomarker sampling such that reproducible circumstances are created at the time of biomarker sampling. This can includes one or more of meals, exercise, therapeutic administration, sleep, hydration, and the like. Additionally, the events 237 in the schedule of events 222 can be adjusted (number, types, timing, etc.), to accommodate work schedule, stressors, and the like of the patient 12.

As mentioned above previously, the adherence criteria 224 is used to assess qualitatively whether an event 237 performed according to the schedule of events 222 provided data which is acceptable to addressing the medical use case upon which the structured collection procedure 70 is based. In particularly, the adherence criteria 224 can provide variables and/or values used to validate data from a performed event 237. For example, an adherence criterion 224 can be a check performed by the processor 102 of the collection device 24 that a value collected in response to an event 237 is within a desired range, or is above, below, or at a desired value, wherein the value may be a time, a quantity, a type, and the like. The same or different adherence criteria 224 may be associated with each of the events 237 within the schedule of events 222 as well with the entry criterion(s) 226 in one embodiment, and as being the exit criterion 228 in another embodiment, such as illustrated by FIG. 6D (i.e., "stop exercising when bG back in target range" which defines both the adherence and exit criteria). In one embodiment, one or more events 237 in the schedule of events 222 may be modified (e.g., added, deleted, delayed, etc.) if a particular event or events fail to met the adherence criterion 224 for the particular event or events. In one embodiment, the failure of the adherence criterion(s) 224 can trigger an adherence event 242. In one embodiment, upon occurrence of an adherence event 242 due to the associated adherence criterion 224 for an event 237 not being met or satisfied, the processor 102 may require one or more additional actions to be performed as a consequence. For example, the processor 102 may prompt on the display 108 additional information to the patient, and/or prompt a question to determine whether the patient 12 is sick, stressed, or unable to perform the request e.g., eat the meal, or exercise. If the patient answers "Yes", e.g., via the user interface 146, then as part of the adherence event 242 the processor 102 can provide a delay to the schedule of event (i.e. suspend). In one embodiment, the delay can continue until the patient indicated that he or she is better in response to another question prompter by the processor 102, such as the next day or after a predefined amount of time as also part of the adherence event. For example, the patient 12, as part of an event 237, is prompted by the processor 102 to administer a drug, but the patient is not at home, such as for example, where his/her insulin is located. The patient 12 can select the delay via the user interface 146, wherein the processor 102 re-prompts the patient as part of the adherence event 242 after a predetermined amount of time. This delay may also have an upper limit in which if the schedule of events 222 is not re-started within a certain amount of the time, the structure testing procedure 70 in such a circumstance may just end. In another embodiment, another form of an adherence event 242 is a violation event, which results when the person executing a structure testing procedure 70 fails to make a recommended change in response to a request. For example, the request or part of an event 237 may be for the patient to adjust a drug dosage from 10 U to 12 U, wherein the patient answers in the negative to a question on the displayed on the display 108 asking if the patient will or has complied with such a change. In response to such a violation event, the processor 102 may also send a message and/or provide a delay as previously discussed above concerning the adherence event.

In another example and in one embodiment, a bG measurement must be collected before each meal in order for a structured collection procedure 70 to provide data that is useful in addressing the medical use case or question for which it was designed, such as identified by the use case parameter 220. If, in this example, the patient fails to take a bG measurement for the lunch meal in response to a request 240 for such a collection according to the schedule of the event 222, and hence the adherence criteria 224 for that event 237 fails to be satisfied, the processor 102 in response to the associated adherence event 242 can be programmed according to instructions in the collection procedure 70 to cancel all remaining events 237 in the schedule of events 222 for that day, mark the morning bG measurement stored in the data file (such as data file 145 (FIG. 4) as invalid, and reschedule for the schedule of event 222 for the next day. Other examples of further actions in which the processor 102 may take in response to an adherence event 242 may be to dynamically change the structure testing procedure by switch to a secondary schedule of event, which may be easier for the patient to perform, provide additional events for measurements to make up the missing data, change the exit criteria from a primary to a secondary exit criterion providing modified criterion(s), change the adherence criteria from a primary to a secondary adherence criterion, fill in the missing data for the failing event with historical data or an estimate based on the historical data, perform a particular calculation to see if the structured collection procedure 70 can still be successfully performed, send a message to a particular person, such as a clinician, of the failing event, provide a certain indication in the associated data record 152 to either ignore or estimate the missing data point, and the likes. In still another embodiments, the adherence criteria 224 can be dynamically assessed, such as for example, based on one or more biomarker values and/or input received from the user interface in response to one or more questions, via an algorithm which determines whether the collected data provides a value which is useful in addressing the medical use case or case. In this example, if the calculated adherence value is not useful, for example, does not fall into a desired range or meet a certain pre-define value, then further processing as defined by the resulting adherence event would then take place, such as any one or more of the processes discussed above.

The exit criteria 228, as mentioned previously above, establishes the requirements for exiting or completing the structured collection procedure 70, so that the structured collection procedure 70 has adequate contextual data to answer the medical question addressed by the structured collection procedure 70. The exit criterion 228 can help increase the efficiency of the structured collection procedure 70 by minimizing the number of required samples needed to address the medical use case. By "addressing", it is meant that sufficient patient data has been collected in which the clinician 14 may render an assessment to the medical use case. In other embodiments, the assessment may be indicated by a given confidence interval. A confidence interval is a group of discrete or continuous values that is statistically assigned to the parameter. The confidence interval typically includes the true value of the parameter at a predetermined portion of the time.

As with the entry criteria 226, the exit criteria 228 can comprise one or more of context specific exit criterion 244, procedure specific entry criterion 246, and combinations thereof. Examples of context specific exit criterion 244 can include one or more variables to identify mood, desired blood glucose events (i.e., blood glucose level), to indicate stress, illness, contraindications, such as for example, hyperglycemia, hypoglycemia, vomiting, a fever, and the likes. Examples of procedure specific entry criterion 246 can include one or more variables to identify a number of events meeting the adherence criteria, biomarker values being in a desired pre-determined range and/or at a desired pre-determined value, a desired disease state, desired disease status, no change in the biomarker after a pre-determined period, or no significant progress over a pre-determined period to a desired biomarker value, and the like. It is to be appreciated that in one embodiment the exit criterion 228 can establish the condition(s) needed to be met for entry criterion 226 of a second structured collection procedure 70. For example, upon having a suitable Insulin-to-Carbohydrate (I:C) determined with a first collection procedure, such as for example, structure collection procedure 70b (FIG. 6B), running a structured test for determining the best time for administering a bolus in regards to a start of a meal, such as for example, structured testing procedure 70c (FIG. 6C), which needs a current I:C ratio, can be conditioned such that the processor 102 can implement automatically a schedule of events of the second structured collection procedure 70c upon meeting the exit criterion of the first structured collection procedure 70b at some unknown time. In other embodiment, for example, the exit criterion 228 of a first structured collection procedure 70 that is being run by the processor 102 according to the schedule of events 222 and the entry criterion 226 of the second structured collection procedure 70 both can be based on the same one or more contraindications, such as mentioned above. In such an embodiment, upon occurrence of a contraindication being provided to and/or detected by the processor 102, such as via the user interface 146 and/or the biosensor 140, respectively, which in this example meets the exit criterion 228 of the first structured collection procedure 70, the processor 102 would automatically start the schedule of events of the second structured collection procedure 70 as the entry criterion 226 of the second structured collection procedure 70 has also been met. An example of such a second structured collection procedure 70 which can be started via exiting a first structured collection procedure can be one which has a schedule of events 222 which requests a biomarker samplings at a routine interval, e.g., every 30 minutes, every hour, every day at a particular time, etc., until the contraindication(s) clears (e.g., biomarker value(s) reaches a desire range or value, patient 12 indicates to processor 102 via user interface 146 no longer having a contraindication(s), expiration of a predefined period, etc.). Such an embodiment is useful if recording the context and values of the events after the occurrence of the contraindication(s) is a desire and in which the first collection procedure should be exited when a contraindication(s) occurs.

The exit criteria 228 can be a single criterion or multiple criteria that establish the conditions to exit the structured collection procedure 70. The conditions are provided in one embodiment such to ensure that adequate contextualized biomarker data has been obtained to answer the medical question being addressed by the collection method. For example, such that a predetermined number of valid samples have been acquired, or that the variability in the samples is below a predetermined threshold. Therefore, it is to be appreciated that the end date and/or time of the collection procedure 70 may be dynamic and be changed automatically by the processor 102 if the predefined condition(s) of the exit criterion(s) 228 is not satisfied. Likewise, the conditions of the exit criterion 228 may be dynamic and be changed automatically be the processor 102 such for example if a particular adherence criterion 224 is satisfied or not satisfied. For example, in one embodiment if adherence criterion 224 for a particular collection event 237 is met, then the processor 102 is instructed to use a first exit criterion and if not met, then the processor 102 is instructed to use a second exit criterion that is different from the first exit criterion. Accordingly, until the exit criterion 228 is satisfied, the end date and/or time of the structured collection procedure 70 can be at some unknown time in the future. In another embodiment, the exit criteria 228 can be assessed after patient data has been collected, such as, on historical patient data.

It is to be appreciated that the entry and exit criteria 226, 228 together with the adherence criteria 224 can help to reduce both the time to perform the structured collection procedure 70 and the expense associated with the collection by defining one or more of the acceptable conditions, values, structure and context needed to perform the schedule of events 222 in an effort to make every collection event 237 count and/or reduce consumption of test strips 30 with unneeded collections that do not help address the medical use case or question. Hereafter reference is made to FIGS. 6A-6E.

Structured Collection Procedure Examples

FIGS. 6A-E illustrate examples of some structured collection procedures 70a, 70b, 70c, and 70d depicting their functions which can easily be translated by one of ordinary skill in the related art into instruction code which may be implemented on any one of the devices the above described devices 18, 24, 25, 26, 28, 36, 52. Therefore, for brevity, no discussion is provided in regard to pseudo-code or actual code relating to these illustrated functions.

Figure 6A:
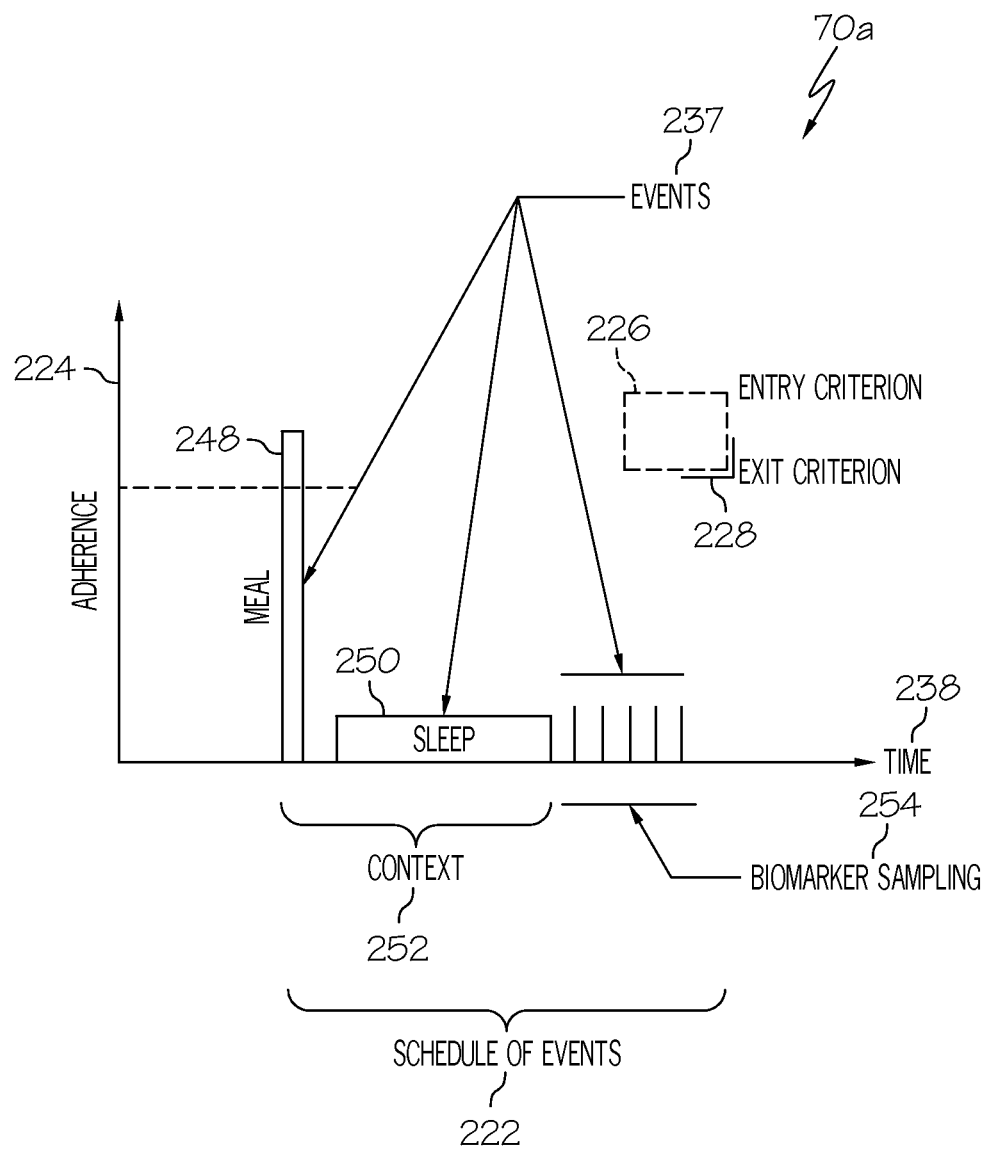
FIGS. 6A, 6B, 6C, 6D, and 6E show various structured collection procedures embodiments defined according to the present invention.

FIG. 6A diagrammatically illustrates an embodiment of a structured collection procedure 70a used to obtain contextualized biomarker data from a diabetic patient. The horizontal axis shows the performance times 238 of the various events 237, and the vertical axis shows adherence criterion 224 without values. In the illustrated embodiment, the events 237 can include recording information regarding a meal 248 and sleep 250 in which to provide context 252 for the five-biomarker samplings 254 also events 237 that are part of the schedule of events 222. In this example, the adherence criterion 224 for the meal 248 can be a value which must be greater than a minimum value, e.g., for a carbohydrate amount. The entry criterion 226, for example, can comprise a biomarker value being above a particular value such as required to meet contextualization requirements to begin the structured collection procedure 70*a*. The exit criterion 228 as well can comprise a biomarker values being below a particular value such as also required to meet contextualization requirements to end the structured collection procedure 70*a*. Such a structured collection procedure 70 is useful for helping to address a number of medical use cases.

GLP1 Structured Testing Procedure

For example, several epidemiological studies have confirmed that elevated postprandial glucose (PPG) levels are a significant predictor of cardiovascular mortality and morbidity in type 2 diabetes (T2D). For this reason, there is a family of human once-weekly long acting glucagon-like peptide-1 (GLP 1) drugs which can be prescribed to T2Ds who show high post prandial bG values. These GLP 1 drugs are similar to the natural hormone GLP-1 which has a key role in blood sugar regulation by stimulating insulin secretion and suppressing glucagon secretion. Therefore, a structured collection procedure 70 can be provided in one embodiment which proposes an intensive measurement of bG values during the time after one or more meals over time allows therapy efficacy to be shown by means of observed reduced postprandial bG values. Based on such observed values, doses recommendation for a GLP 1 drug and/or whether a particular GLP 1 drug is the right drug at all for the patient can be determined.

For example, the structured collection procedure 70 could be provided on a collection device 24 for when a patient has been prescribed to administer a particular drug, e.g., a GLP 1 drug. In the case of a GLP 1 drug, in which determination of drug efficacy is desired, the entry criterion 226 for such a structured collection procedure could then be that the patient must affirm to the processor 102 in response to a question displayed on the display 108 to perform the structured collection procedure 70 over a period of time (e.g., over the next 4 to 24 weeks) and/or the processor 102 has determined that the mean PPG level of the patient from prior post prandial bG values over a period (e.g., week, month, etc.) are high (e.g., greater than 141 mg/dl). Still other factors could be used as the entry criterion(s) 226, such as fasting blood glucose being more than a certain value, e.g., 126 mg/dl or less than a certain value, e.g., 240 mg/dl.

After the conditions of the entry criterion(s) 226 have been satisfied and confirmed by the processor 102, the schedule of events 222 is then automatically run by the processor 102. The schedule of events 222 would specify desired collection events 237 in which the processor 102 would automatically prompt the patient for entering post prandial bG values after breakfast, lunch, and dinner (i.e., performing a bG measurement on a sample provided to a test strip that is read by the measurement engine and provided to the processor for storing in a data record and display). As customized by the prescribing physician, the schedule of events 222 could also define a collection event 237 with a performance time 238 in which the patient must administer the drug as well as to provide a reminder of the dosage and a request 240 for confirmation from the patient when the drug has been administered. For example, the processor 102 in executing the schedule of events 222 would automatically prompt the patient to administer dosages at the times specified by the collection events 237 in the schedule of events 222, e.g., 10 mg of Taspoglutide on a certain day of the week, and then after a period, a second dosage according to a second interval, e.g., after 4 weeks, then 20 mg also on a certain day of the week. A collection event 237 could also be defined in the schedule of events 222 in which the processor 102 makes a request on the display 108 for information, such as whether the patient is feeling well, to provide an indication of energy level, to provide an indication of size of meals consumed, and the like.

A condition(s) for the adherence of each entered post prandial bG value could be provided via the use of adherence criteria 224 in which any post prandial bG value entered (i.e., measured) an amount of time before or after the prompting, e.g., a testing window of ±30 minutes, such a measured value would not be accepted as a valid measurement for the schedule of events 222 by the processor 102. In one embodiment, the processor 102 can take further action automatically based on the adherence criteria 224 assessment preformed automatically by the processor 102. For example, if a bG measurement was taken before a measurement prescribed by a collection event in the schedule of events 222 and outside the defined testing window, e.g., −30 minutes before the collection event time, the processor 102 in such a case will automatically notify the patient that a measurement is still needed at the prescribed time as the previous measurement was not accepted since outside the testing window. Likewise, if after the testing window, e.g., the collection event time+30 minute, the processor 102 can automatically notify the patient that the previous measurement was not accepted since outside the testing window and provide encouragement on the display 108 to the patient to make an effort take a measurement within the testing window.

The exit criterion 228 for such a GLP 1 structured collection procedure 70 could be an indication that the mean bG value, in using a minimum amount of time (e.g., days, weeks, months, etc.), a minimum number of accepted measurements, or both, has reached a desire value. Likewise, the exit criterion 228 could be an indication that the mean bG value, after a maximum amount of time (e.g., days, weeks, months, etc.), a maximum number of accepted measurements, or both, has not reached a desire value. Still further, the exit criteria 228 can be other factors which indicate that the drug or dosage is not at all right for the patient, such as the patient responding as having nausea and/or vomiting each day for a minimum number of days in response to a collection event for such information prompted by the processor 102 on the display 108. Still other factors could be used as the exit criteria 228, such as fasting blood glucose being less than a certain value, e.g., 126 mg/dl or greater than a certain value, e.g., 240 mg/dl. The data collected from such a drug base structured collection procedure 70 can then be used by a physician to make a dosage recommendation for the GLP 1 drug and/or determine whether the particular GLP 1 drug is the right drug or not for the patient.

Figure 6B:
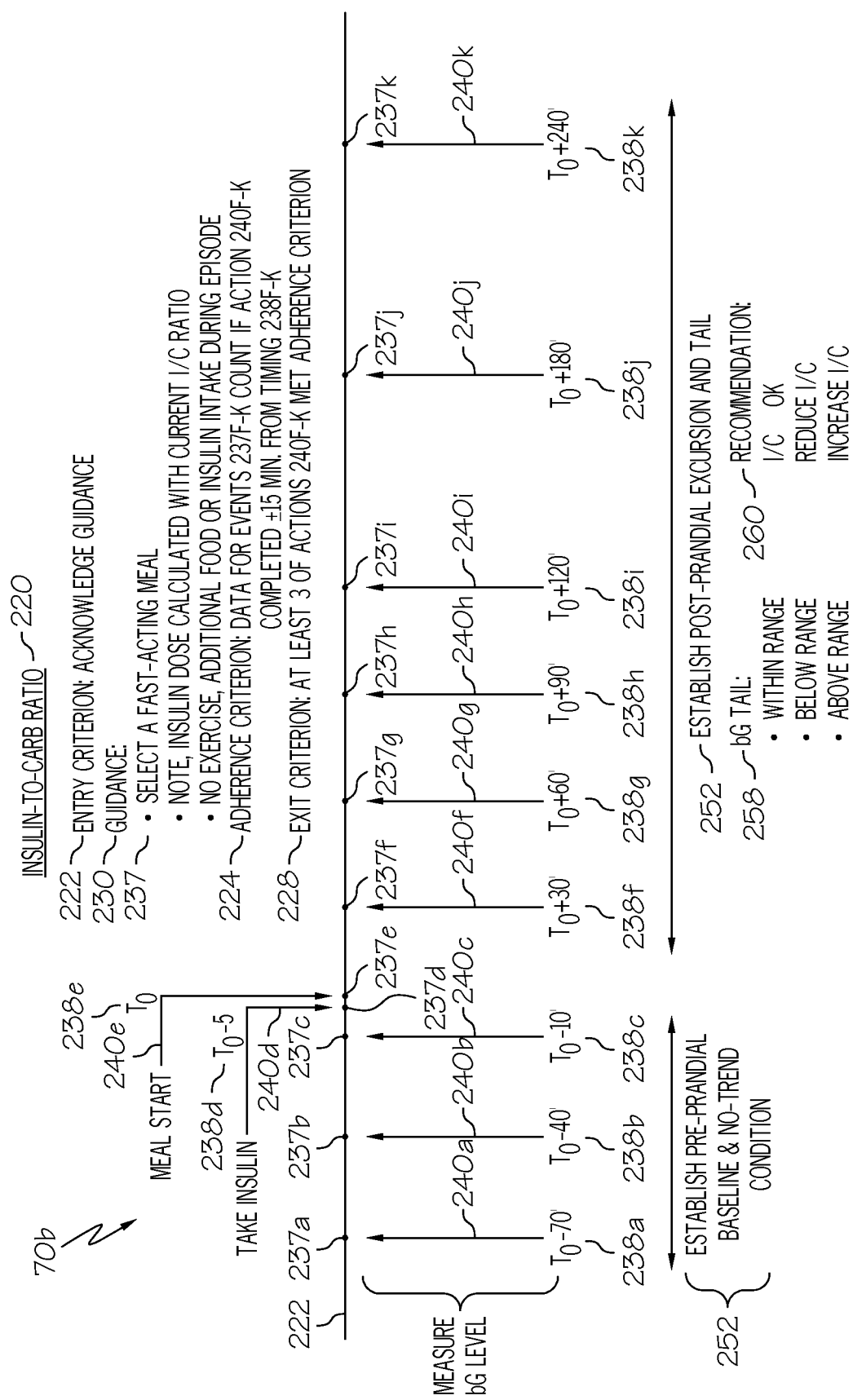

Another example is diagrammatically depicted by FIG. 6B which shows a structured collection procedure 70*b* which has a defined medical use case parameter 220 indicating that the procedure can be helpful for determining suitability of an insulin to carbohydrate (I:C) ratio. As illustrated, the entry criterion 226 is defined as having the patient simply acknowledge guidance 230 of selecting a fast-acting meal, to note that the insulin dose is calculated with the current I:C ratio as well as agreeing not to exercise, take additional food or insulin during the testing period. For example, the processor 102 can present on the display 108 such guidance 230, which the user can then acknowledge after reading with either a "Yes" or a "No" entered via using the user interface 146 for the desired entry choice. If the user enters "Yes", then the entry criterion 226 is satisfied, and the processor 102 automatically starts the schedule of events 222 defined in the structured collection procedure 70*b*. In another embodiment, the entry criterion 226 may be or include satisfying a request for selecting a fast-acting meal. For example, the request 240 for selection can be the processor 102 displaying on the display 108 a selection menu providing a listing of fast-acting meals to which input of such a selection via the user interface 146 is needed. For example, selection of a fast-acting meal may be made via a press of one of the buttons 147, 149 or via the touch screen interface if provided by display 108. Such a selection can then be stored in memory 110 of the collection device 24 such as setup data 163 (FIG. 4) which may be part of the data file 145 (FIG. 4) for the structured collection procedure 70b. In an alternative embodiment, a particular fast-acting meal may be recommended by the structured collection procedure 70b.

As shown, the schedule of events 222 can comprise one or more events, such as the plurality of events 237a-k illustrated and with each having associated performance times 238a-k and requests for action 240a-k. As shown, the requests for action 240a-c, and 240f-k are requests for the user to take a bG level measurement, request 240d is to take an insulin dose, and request 240e is to eat the fast acting meal. Also shown is that events 238f-k each have an adherence criterion 224, which must be met if the data for events 238f-k are to be recorded in the data file 145. In this example, the adherence criteria 224 requires that the actions 240f-k be completed within ∀20 minutes of their corresponding performance times 238f-k in order for a data record 152 recording the received value(s) for the corresponding event 237f-k to count towards completing the collection procedure 70b. In one embodiment, the processor 102 will make each of the requests 240a-k at their associated performance times 238a-k in order to obtain resulting data values e.g., data values 256a-k (FIG. 4) at the time the requests are performed.

For example, the processor 102 can prompt the patient 12 with a request 240a to take a bG level (biomarker) measurement at performance time 238a. The resulting measurement when received by the processor 102, such as automatically from the measurement engine 138 after reading the test strip (biosensor) 140 for the desired biomarker, is then recorded automatically by the processor 102 in the date file 145 as a corresponding data value 256a for the associated event 237a. For actions 240d and 240e, at a required time, the processor 102 can automatically prompt the patient 12 to take the prescribed action at the required time, and again automatically prompt the patient thereafter to confirm that the required action has been taken, or that a predefine status has been achieved. A date-time stamp 169 can also be provided in the date record 152 automatically by the processor 102 upon triggering of the requests 240a-k, acknowledgement of the requests 240a-k, upon completion of the event 237a-k, upon receiving a data value 256a-k for the event 237a-k, and combinations thereof. Additionally, in another embodiment, the patient 12 can record data values 256a-k for one or more events 237a-k by entering the data directly into the device 24 via the user interface 146, wherein the processor 102 stored the entered data values/information in the associated data record 152 for the event 237a-k, or in other embodiments can record a voice message with the information for later transcription into digital data. In still other embodiments, the patient 12 can be guided by the collection device 24 to record data for an event 237a-k using a paper tool 38.

As mentioned previously above, each event 237 can be a recording of a biomarker value, or a request for a required patient action that is necessary in order to create a context for the biomarker value, such as for example, meals, exercise, therapeutic administration, and the like. In the illustrated embodiment, the context 252 for completing events 237a-c is to establish a pre-prandial baseline and a no-trend condition, and for events 237f-k to establish a post-prandial excursion and tail. Such context 252 for these events may also be associated with the corresponding data records 152 for each event as contextual information 156 (FIG. 4). Such information is useful later when reconstructing the data and/or when there is a desire to know the context for which the data record was created.

It is to be appreciated that any patient action taken outside of the required requests for patient actions 240a-k can also be recorded by the processor 102 but will not be considered by the processor 102 as part of the collection procedure 70b. Data 256a-k for events 237a-k that are prospective can be identified based on a type of event, the time of the event, the trigger of the event, and combination thereof. Each of the performance times 238a-k can be fixed or variable based on prior data. Some of the event 237a-k in other embodiments can also be a past, current, or a future event such as for meals, exercise, and the like, or data values such as for hypoglycemic events, hyperglycemic events, or data of a specific value of interest. In some embodiments, the events 237a-k can be identified via a paper tool 38 that is procedure based.

As also shown, the structured collection procedure 70b will end if the condition of the exit criterion 228 is satisfied. In this example, the exit criterion 228 is satisfied if at least three of the actions 240f-k met the adherence criterion 224. For example, the processor 102 may provide a unique identifier (e.g. an incremental count) 167 (FIG. 4) in the data file 145 for each event 237a-k performed and to which satisfied the adherence criterion 224 if required. In the illustrated embodiment of FIG. 4, events 237a-c and 237e-k each receive a unique identifier but not event 237d, e.g., <null>, since not satisfying an associated adherence criteria (not shown). In addition, analysis logic 258 and resulting recommendations 260 can also be provided in the structured collection procedure 70b which the processor 102 may apply automatically to the data collected upon satisfying the exit criterion 228 in one embodiment.

Figure 6C:
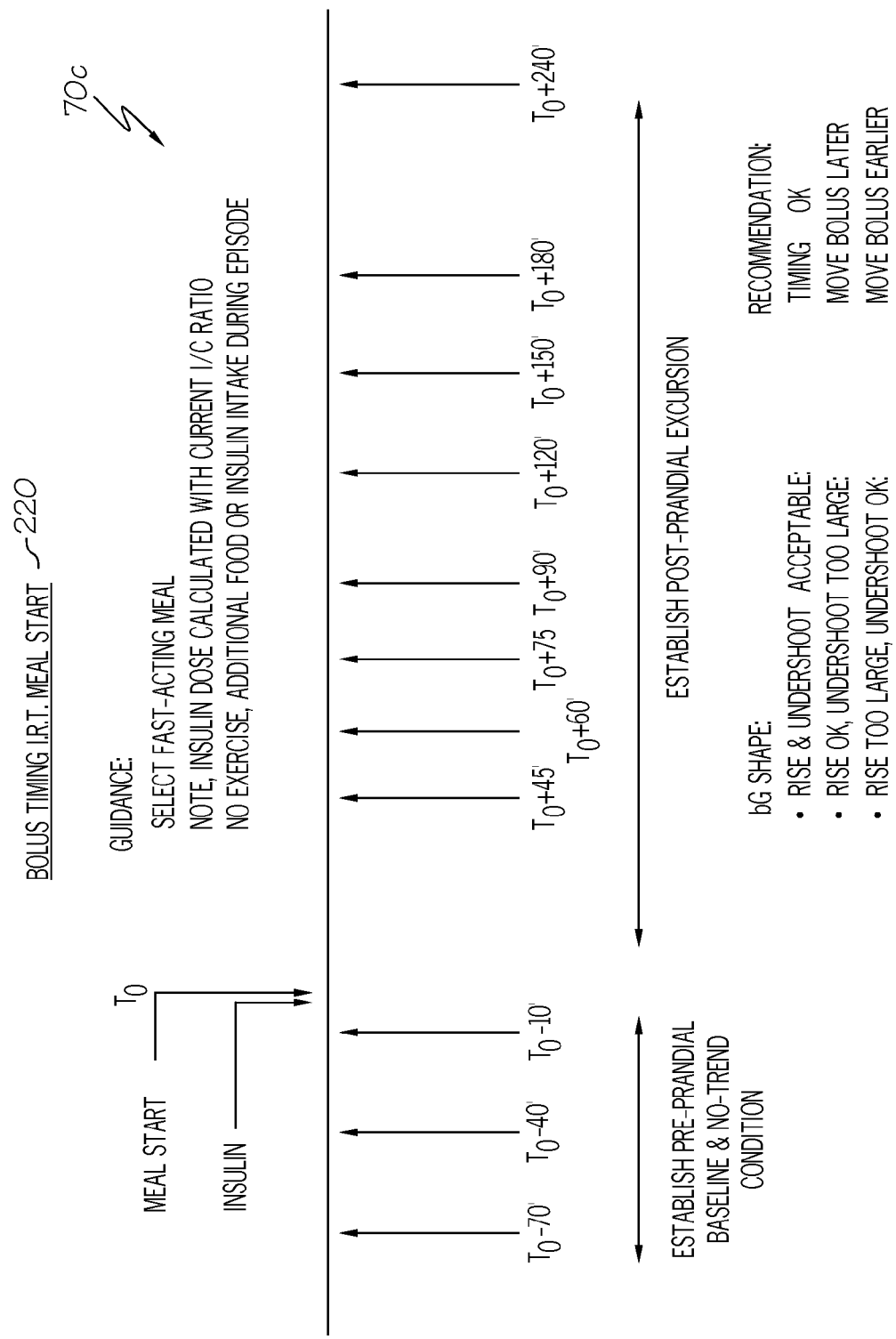
Figure 6D:
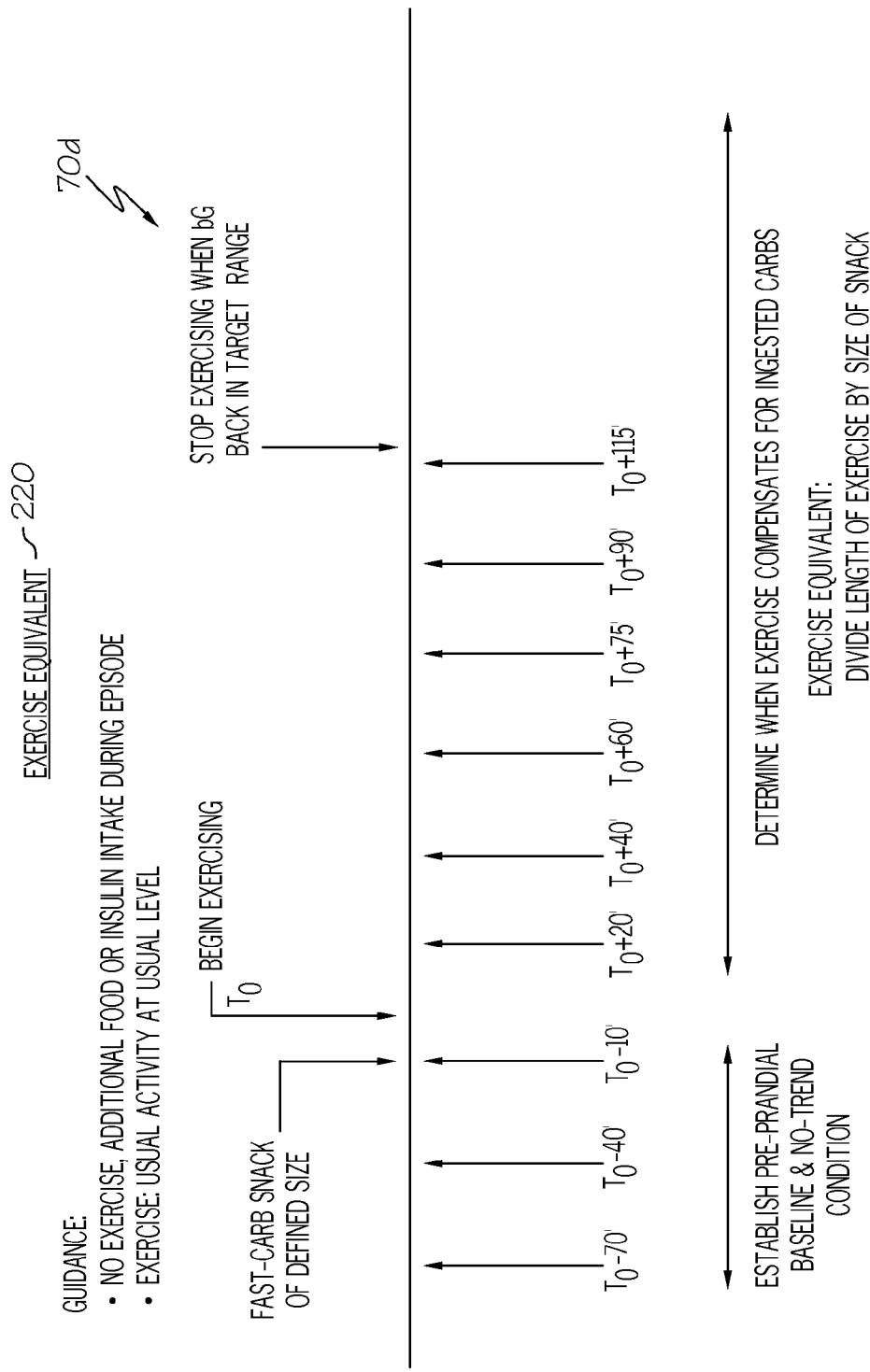

Similar features are also provided in the examples illustrated by FIGS. 6C and 6D, wherein FIG. 6C depicts a structured collection procedure 70c which has a defined medical use case parameter 220 indicating that the procedure is helpful for determining suitability of a bolus in regards to a meal start. Likewise, FIG. 6D depicts a structured collection procedure 70d which has a defined medical use case parameter 220 indicating that the procedure is helpful for determining suitability of an exercise equivalent to a carbohydrate intake. In addition to the above examples, other such structured collection procedures may be designed to address other various medical use cases such as, for example, the following: determining the effects of eating a particular food on a biomarker level of a patient; determining the best time to take medication before and/or after a meal; and determining the affect of a particular drug on a biomarker level of a patient. Still other structured collection procedures can be provided which may be useful in addressing questions concerning how best to initialize therapy for a patient, finding a determination of status of a patient disease progression, finding the best ways to optimize a patient therapy, and the like. For example, the clinician 14 can define and/or use a pre-defined structured collection procedure 70 which looks at factors which may have an effect on the therapy of the patient. Such factors can include, for example, stress, menstrual cycle, pre-dawn effect, background insulin, exercise, bolus timing with respect to a meal, basal rate, insulin sensitivity, post-prandial behavior, and the like.

Figure 6E:
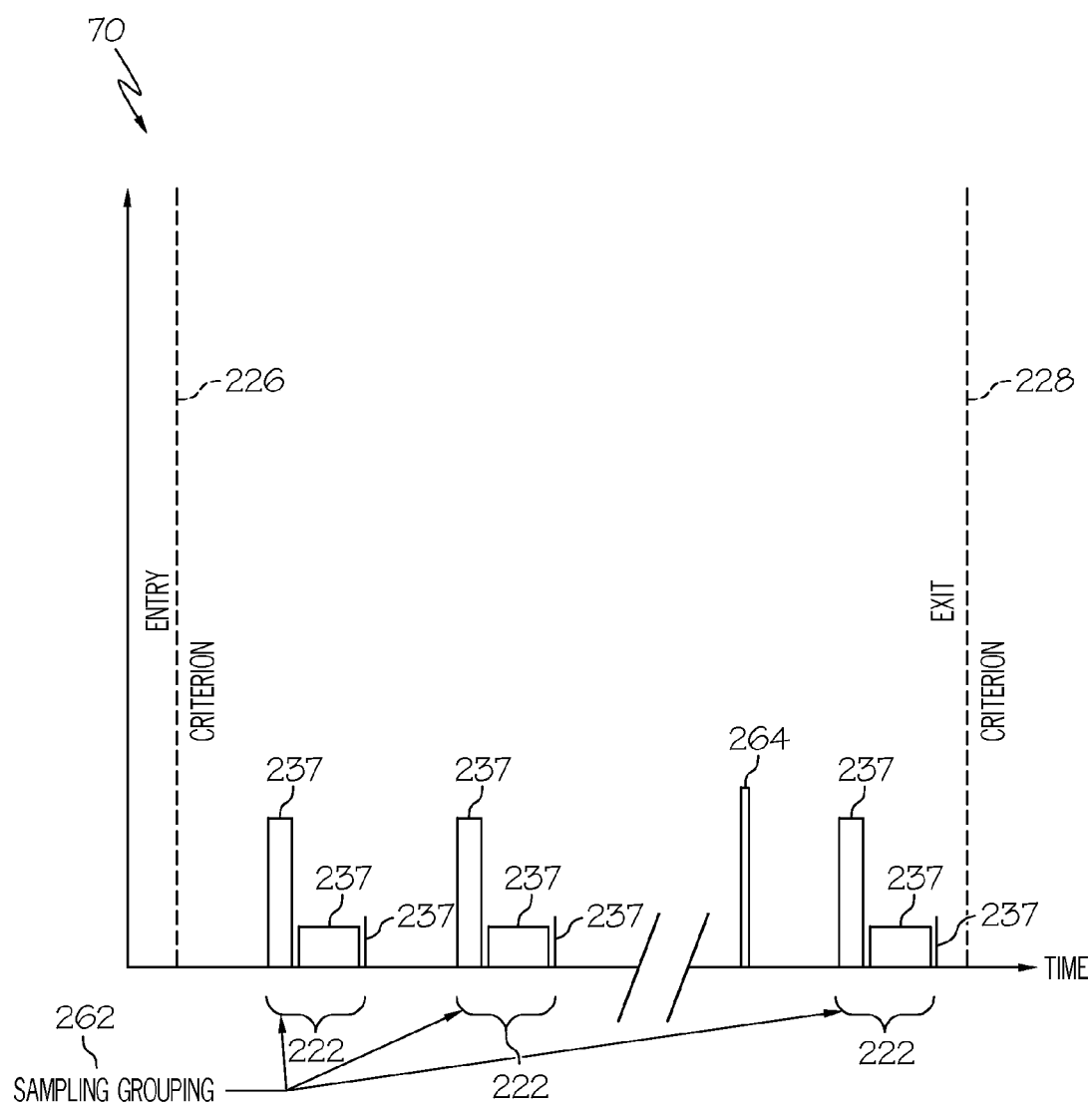

FIG. 6E shows a diagram structured collection procedure 70 comprising one or more multiple sampling groups 262 each comprising a recurring schedule of events 222 provided between the entry criterion 226 and the exit criterion 228. In this example, the schedule of events 222 comprises one or more events 237 occurring each day at consistent times of day. As the structured collection procedure 70 in the process of obtaining contextualized biomarker data from a diabetic patient 12 can span over multiple days, even week and/or months before the exit criterion 228 is met, one or more checks 264, such as for parameter adjustment, and/or evaluation of whether to re-run the sampling groups 262, can also be provided between the entry and exit criterions 226, 228 in one embodiment. The duration between such checks 264 can be used for physiological system equilibration, evaluation of treatment efficacy, or convenience. For example, either between each sample grouping 262 or after a predefined number such sampling grouping 262 (as shown), an analysis for the check 264 can be performed by the processor 102 to determine whether an adjustment to any parameter in the collection procedure 70 is needed.

For example, such analysis may be either for a parameter optimization or efficacy assessment. For the parameter optimization, the processor 102 can run calculations on the samples provided within a previous schedule of events 222 or sample grouping 262, using information from prior optimizations, clinician set parameters, and a collection or therapy strategy, recommends a new parameter value. For the efficacy assessment, the processor 102 can evaluate data not utilized by the optimization analysis. Additionally, it is to be appreciated that after a group of samples, i.e., sampling group 262, are taken the processor 102 can also evaluate the data from the sampling group 262, such as if such data is need in order to alter/optimize a person's therapy. Adherence criteria can be applied to perform this evaluation to the data of the sampling group 262 or set. For example, a first adherence criterion 224 can be used by the processor 102 to assess whether a minimum amount of data is provided by the sampling group 262 and if not, for example, the alteration/optimization of the patient's therapy will not take place. Another adherence criterion 224 could permit the processor 102 assess whether the data is acceptable to permit an adjustment called for by the check 264, such as looking at spread of the data, whether these is too much variability (noise), as well as other data attributes to use the data. In this example, if meeting such adherence criterion, then processor 102 has assessed that there is minimum risk that adjusting a parameter of the procedure could readily result in a severe event, e.g., hyper- or hypoglycemic event. Lastly, an adherence criterion can be used by the processor to assess the exit criteria based on the data of sampling group, for example, the exit criterion is met when the data from the sampling group 262 satisfies the adherence criterion, such as for example, discussed above, for the sampling group.

It is to be appreciated that collection or therapy strategies can be categorized into scale based (sliding or fixed) assessments or formula based assessments. As input to the collection or therapy strategy, the processor 102 in one embodiment can utilize the data collected from a predetermined number of prior sample grouping(s) 262. This data can be either used as individual points (only the formula based collection or therapy strategies), or combined with filtering for use in a scale based assessment. In another embodiment, for example, the result of a check 264 performed by the processor 102 can also result in a status or recommendation being provided by the processor 102 automatically. Such status or recommendation may be e.g., a status of continuing with current parameter values, a recommendation to change particular parameters, a recommendation to change the adherence and/or exit criterion, a status that the processor 102 switched to a secondary adherence and/or exit criterion based on the analysis performed on the data from a prior schedule of events or prior sample grouping, or a recommendation to terminate the collection procedure, and the likes. A discussion of performing a structured collection using a structured collection procedure according to an embodiment of the present invention is provided hereafter with reference made to FIG. 7A.

Structured Collection

Figure 7A:
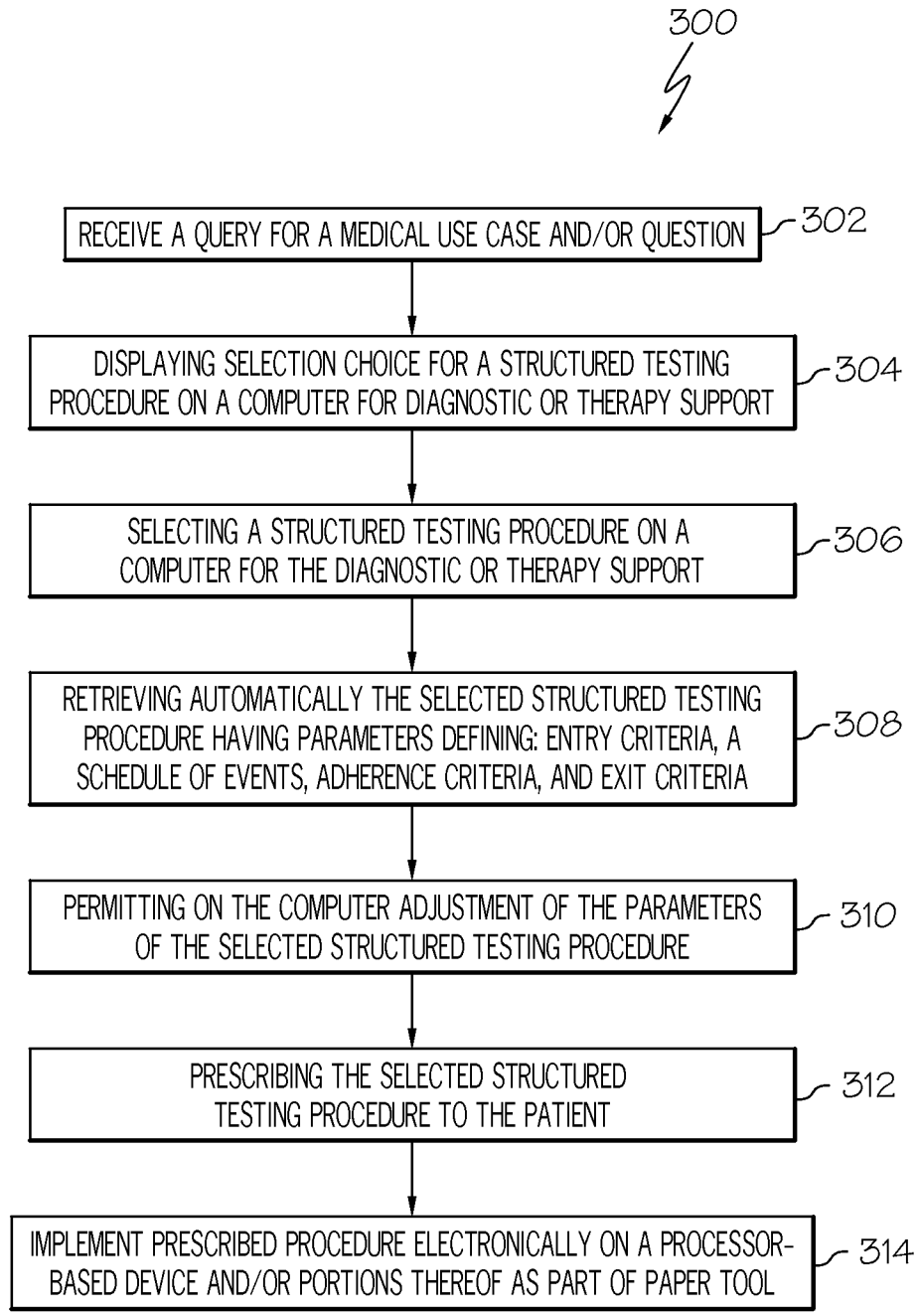
FIG. 7A depicts a structured collection for diagnostic or therapy support of a patient with a chronic disease according to an embodiment of the present invention.

FIG. 7A depicts a structured collection 300 for diagnostic or therapy support of a patient with a chronic disease. The method 300 may be implemented as instruction codes of a program running on a computer with a processor and memory, such as preferably clinician computers 25 (FIG. 2) as stand-alone software, as part of software 34, or as software provided as a service by server 52 via a secure web implementation over public network 50. Upon a processor 76 executing the program from memory 78 of the clinician computer 25, as one function among others, the processor 76 after receiving a query for a medical use case and/or question, searches memory 78, computer readable medium 40, and/or server 52 for all structured collection procedures 70a-d, which matches the submitted query in step 302. For example, the processor 76 may read the medical use case parameter 220 of each available structured collection procedures 70a-d and using a conventional search algorithm (e.g., list, tree, heuristics, etc.), provide on a display 82 a selection choice for those structured collection procedure matching the query in step 304 in one embodiment.

In one embodiment, the list displayed can reflect, for example, the structured collection procedures 70a, 70b, 70c, and 70d available for use from the server 52. In still another embodiment, the list of selection choices displayed can be dynamically created based on a type of medical use case the clinician 14 wishes to investigate. For example, prior to step 302, a list of selectable medical use cases can be displayed on the display 82 by the processor 76. In such an embodiment, the clinician 14, using the user interface device(s) 86 may selected from among the displayed medical use cases, for example, the medical use case "Determining meal effect on patient's therapy." After the clinician makes such a selection, which the processor 76 receives as input from the user interface device(s) 86, the processor 76 after using decision logic (e.g., if . . . then) provided by the software 34 would then display in step 304, for example, structured collection procedure 70b (e.g., a structured collection procedure to determine a more accurate insulin-to-carbohydrate ratio) and 70c (e.g., a structured collection procedure to determine bolus timing in regards to meal start), and not structured collection procedures 70a and 70d, which are structured collection procedures unrelated to the medical use case. Likewise, a "show all structured collection procedures" could also be a choice among the displayed medical use cases, in which the complete list of available structured collection procedures would then be displayed in step 304. In another embodiment, step 302 may be skipped and the processor 76 in step 304 can just provide a display of the structured collection procedures 70a-d available in memory 78 of the clinician computer 25.

In step 306, a clinician using the user interface devices 86 can select a structured collection procedure 70 on the computer 25 for diagnostic or therapy support. For example, the selecting process can include choosing from the list displayed in step 304, which provided one or more structured collection procedures. After the clinician makes such a selection in step 306, which the processor 76 receives as input from the user interface device(s) 62, the processor 76 of the computer 25 retrieves automatically from an electronic component, e.g., computer memory 78, server 52, or computer readable medium 40, and displays the selected structured collection procedure 70 on display 82 for viewing.

It is to be appreciated that each structured collection procedures 70a, 70b, 70c, and 70d is based on a medical use case and has parameters defining entry criteria 226, a schedule of events 222, adherence criteria 224, and exit criteria 228. As mentioned above, the entry criteria 226 establish the conditions needed to be met prior to obtaining biomarker data from the patient. Each event 237 of the schedule of events 222 comprises a performance time, patient guidance to perform the event, patient actions, a request for information from the patient, a request for collection of at least one type of biomarker data from the patient, and combinations thereof. The adherence criteria 224 is used to qualitatively assess whether an event 237 performed according to the schedule of events 222 provided data which is acceptable to addressing the medical use case upon which the structured collection procedure 70 is based. Additionally, as mentioned above, the exit criteria 228 establish the conditions needed to be met prior to exiting the structured collection procedure 70.

In step 310, after the processor 76 displays the selected structured collection procedure 70, the clinician 14, to meet the needs of the patient 12 and/or interests of the clinician, may adjust any one of the parameters 222, 224, 226, and 228 which are also displayed on the display 82. Safe guards may be implemented to ensure that only the clinician 14 can modify such parameters and/or run the software 34, such as via password protection. The processor 76 receives any such changes to the parameters 222, 224, 226, and 228 as input via user interface devices 86 and saves the revised structured collection procedure 70 in memory 78. Next, in step 312, the selected structured collection procedure 70 is prescribed on the computer 25 to the patient 12 by the clinician 14, wherein the processor 76 of the computer 25 provides as output the selected structured collection procedure 70 to the patient 12 to perform. For example, in step 314, the prescribed structured collection procedure 70 is implemented electronically on a processor based device, such as collection device 24, or any of the other above described devices 18, 28, and 36 (FIG. 1), as part of the software 34 or in other embodiment, portions thereof as part of paper tool 38.

In one embodiment, the prescribed structured collection procedure 70 may be implemented from the clinician computer 25 (FIG. 2) to the collection device 24 via communication link 72, via the public network 50 through a webpage and/or made available for downloading on server 52. In still other embodiments, the prescribed structured collection procedure 70 can be provided through the computer readable medium 40 and loaded by one of the devices 18, 24, 28, and 36, downloaded from another one of the devices 18, 24, 25, 26, 28, and 36, or downloaded via cell phone or telephone connection from server 52. Notice that a new/updated/prescribed structured collection procedure 70 available for use on the devices 18, 24, 25, 26, 28 and 36 may be provided in any standard fashion, such for via postal letters/cards, email, text messaging, tweets, and the likes.

Customizing a Structured Collection Procedure

FIG. 7B conceptually illustrates one example of a pre-defined structured collection procedure 70, which has a defined medical use case parameter 220 indicating that the procedure is helpful for medical use cases or questions which need to know the trends in blood glucose (bG) levels of a patient and/or the relationships between blood glucose values and time of day, meal size, and energy level. As mentioned above previously, the use case parameter 220 can be used as an identity tag in which the processor 102 may locate the associated structured collection procedure 70 in response to a search query, such as, for entered use case or question. For example, the search query can be entered into the collection device 24 via the user interface 146 and/or received from the clinician computer 25. Such a search query may result from a desire to know which uses case can be addressed by the structured collection procedures 70 currently available on the collection device 24, or to know which structured collection procedure 70 would be useful to address a particular use case or question. Therefore, the use case parameter 220 in one embodiment permits a structured collection procedure 70 to be automatically chosen by the processor 102 from a plurality of structured collection procedures 70a-d, such as provided in memory 110, memory 78, computer readable medium 40, and/or server 52 based on a selection, such as from a displayed list on the display 108 provided by the processor 102, or from input received by the processor 102 from the user interface of a defined medical question. In other embodiments, the use case parameter 220 may also indicate the structured collection procedure 70 is also useful for showing relationships between bG level values and time of day, meal size, and/or energy level.

In one embodiment, the pre-defined parameters of the structured collection procedure 70 can be displayed for modification/customization by the processor 102 of the collection device 24 on the display 108 and/or by the processor 76 of the clinician computer 25 on the display 82 by an authorized user. Such an authorized user may be identified, for example, on the collection device 24 and/or the clinician computer 25 by a password entered via the user interface 146, 86, respectively. In such an embodiment, the pre-define parameters of structured collection procedure 70 can be displayed on the display 108, 82 in which customizable parameters can provide editable or selectable variables via drop-down boxes with various selection choices, radio buttons, check boxes, formatted fields requesting a specific type of information (mm-dd-yyyy, number, letter, etc.), text boxes to enter messages to be displayed, and the likes. The structured collection procedure 70 can be displayed for editing in tabular format (as illustrated) in one embodiment or in a sequential manner listing one parameter at a time in a scroll-through fashion in another embodiment. In still another embodiment, structured collection procedures can be provided which cannot be modified.

As shown by FIG. 7B, the structured collection procedure 70 may further comprise parameters defining one or more criterions setting the conditions needing to be met by the patient 12 to start of the structured collection procedure, i.e., entry criterion(s) 226, to end the structured collection procedure i.e., exit criterion(s) 228, and combinations thereof. In one embodiment, the processor 102 of the collection device 24 uses the one or more criterions to automatically start, evaluate, and end the structured collection procedure 70 if the condition(s) defined by the structured collection procedure are met. In still another embodiment, adherence criterion(s) 224, which are the conditions needing to be met in order for the collected datum/data to be accepted, can also be provided in the structured collection procedure 70.

As also shown in FIG. 7B, the structured collection procedure 70 further comprise parameters defining one or more (collection) events 237 which together form the schedule of events 222. Each of the events 237 comprises one or more requests 240, e.g., for a measurement from the measurement engine 138 of a biomarker value for a sample provided to the biosensor 140, and/or for information to be entered by the patient via the user interface 146 such as in response to a question presented by the processor 102 on the display 108. In the illustrated embodiment, the requests 240 are for a bG measurement, a meal size indication (S, M, or L), and an energy level indication (1, 2, 3, 4, 5), in which 1 is lowest and 5 is highest. Other such requests 240 can include indicating whether the patient exercised, indicating a particular food that was consumed, indicating which medicine was administered, indicating dosage of the medicine administered, and the like may also be provided in other structured collection procedures 70. In the illustrated embodiment, the collection events can be customized by selecting which request 240 the processor 102 should perform via a yes/no selection box.

The structured collection procedure 70 may also include guidance 230 and timing or performance time 238 associated with each of the collection events 237 as well as with each of the entry, exit, and adherence criterion/criteria 226, 228, and 224. Such guidance 230 is provided by the processor 102 to the display 108 upon the occurrence of the associated collection event 237 or other parameters. For example, a collection event 237 for a bG measurement before breakfast may also have a request 240 for an indication of the energy level of the patient. Therefore, in this example, the associated guidance 230 which states, "Please indicate energy level" is provided on the display 108 by the processor 102. It is to be appreciated that the guidance 230 is a text box, field, area, which enables for information to be provided to the patient to help the patient in performance of the structured collection procedure 70. In this example, selection of a number from 1 to 5 may be made via a press of one of the buttons 147, 149 or via the touch screen interface if provided by display 108 as a data entry for such a request 237, which is then stored by the processor 102 in memory 110 of the collection device 24 as part of a data file 145 (FIG. 4) for the structured collection procedure 70.

The timing parameter 238 of the structured collection procedure 70 is used to specify for any one of the associated collection event 237, the entry, exit, and adherence criterion/criteria 226, 228, 224, either a specific date and/or time (mm-dd-yyyy, hh:mm), or a period (n) after a preceding collection event in which to perform the associated collection event. The periods $n_1$, $n_2$, $n_3$ in the illustrated embodiment for the respective collection events 237 indicate hours, but in other embodiments can be indicated in minutes or seconds. In another embodiment, the timing or performance time parameter 238 for an associated collection event 237 and for the entry, exit, and adherence criterion/criteria 226, 228, 224 can be modified by another collection event and/or by the criterion/criteria.

For example, in the illustrative embodiment, the entry criterion 226 is modified by the adherence criterion 224 by adding a day if the guidance 230 provided in the form of a question "Are you willing to conduct a test over 3 consecutive days?" is not affirmed by the patient 12 e.g., via a "No" selection provided on the collection device 24. In this illustrated example, the "Affirms guidance" may be a drop down selection provided in a combo box for customizing the adherence criterion 224 of the associated collection event 237, which when selected causes the processor 102 to wait for the accepted/not accepted input (e.g., via buttons 147, 149) before executing the remaining logic ("if not add 1 day to timing") of the adherence criterion 224. Still further in this example, the processor 102 in accordance with the logic provided in the adherence criterion 224 associated with the exit criterion 228, can set the timing or performance time parameter 238 of the exit criterion 228 to the date (mm-dd-yyyy) that is 3 days after completing the entry criterion 226. It is to be appreciated that the various possible combinations of logic statements which may be performed by the structured collection procedure 70 can be pre-defined and selected by a drop down box in order to be customized in one embodiment, and/or logic statements can be built in another embodiment.

The structured collection procedure 70 can also includes an options parameter 232 associated with each of the collection events 237 as well as with each of the entry, exit, and adherence criterion/criteria 226, 228, 224. The options parameter 232 can have a customizable value(s) to govern whether the data and/or results of the associated collection event 237 or any of the other parameters e.g., entry, exit, and adherence criterion/criteria 226, 228, 224, in the structured collection procedure 70 meets a particular condition such that still further processing may be carried out by the processor 102 if such a condition(s) is meet. For example, such options can be to have the processor 102 automatically send a message to the physician indicating that the patient has started the structured collection procedure 70 via satisfying the entry criterion 226, or to provide a message to the patient and/or the physician if the patient fails a collection event 237 by not satisfying an adherence criterion, or to provide a message to the physician when the patient completes the structured collection procedure 70 when the exit criterion is satisfied, or combinations thereof. For example, such an options parameter 232 can have a global list of such actions which is selected on the display 108, for example, by a selected value from a range of values associated with each option. For example, the options for each parameter can be customized via selecting from a drop down box having option choices (e.g., 1, 2, 3, 4, 5, . . . , A, B, C, etc.) and in which, for example, Option 1 of having the processor 102 provide a message to the physician if the patient fails a collection event 237 (e.g., by not satisfying an adherence criterion), is shown selected for the before breakfast collection event 237. An example in the context of patient 12 being diabetic is provided hereafter to illustrate further such features provided on a collection device 24 according to the present invention.

A typical patient with Type 2 diabetes may measure his/her blood glucose once per day after waking up in the morning. At a routine office visit, the patient's HbA1C result is found to be elevated. The physician recommends that the person goes through three days of intensified glucose monitoring, and selects the structured collection procedure which is useful for this purpose. The structured collection procedure 70 is then customized as discussed above such that during these three days collection events 237 are defined with a number bG measurement requests 240 such that the patient can be requested by the processor 102 to measure his/her blood glucose before and two hours (e.g., $n_1$=2) after breakfast, before and two hours ($n_2$=2) after lunch, before and two hours ($n_3$=2) after supper, and at bedtime. Additionally, the patient 12 can be requested via other associated requests 240 for each collection event 237 to provide an assessment of the relative size of the ingested meals at the appropriate times as well as an indication how he/she feels with regard to energy level. In the illustrate embodiment of FIG. 7B, the processor 102 can request the indication of energy level with each collection event 237 and the assessment of the relative size of the ingested meals every other collection event 237 (i.e., after the meal). Furthermore, the physician has provided a condition via adherence criterion 224 of having to perform the meal assessment within ±30 minutes of period (n) of the associated collection event 237 in order for such information to be useful in the assessment. Such information is useful to contextualize the collected data and for the analysis performed on the collected data.

Additionally, the physician would like to be notified when the patient has failed to complete the "before breakfast" collection event 237. Therefore, to facilitate the notification option, the physician customizes the structured collection procedure 70 by set the options parameter 232 associated with the "before breakfast" collection event, via a drop down box to "Send a message to the physician if adherence criterion fails." All other collection events 237 have their associated options parameter 232 default to indicate that the processor 102 is not to take any additional action with regards to the options parameter. It is to be appreciated that the above described features and arrangements in the illustrated embodiment of FIG. 7B, provide a simple and convenient interface and method for customizing a structured collection procedure, such as for parameter adjustments carried out in step 310 of method 300 previously discussed above in reference to FIG. 7A.

Implementing and Performing a Structured Collection Procedure

Figure 8A:
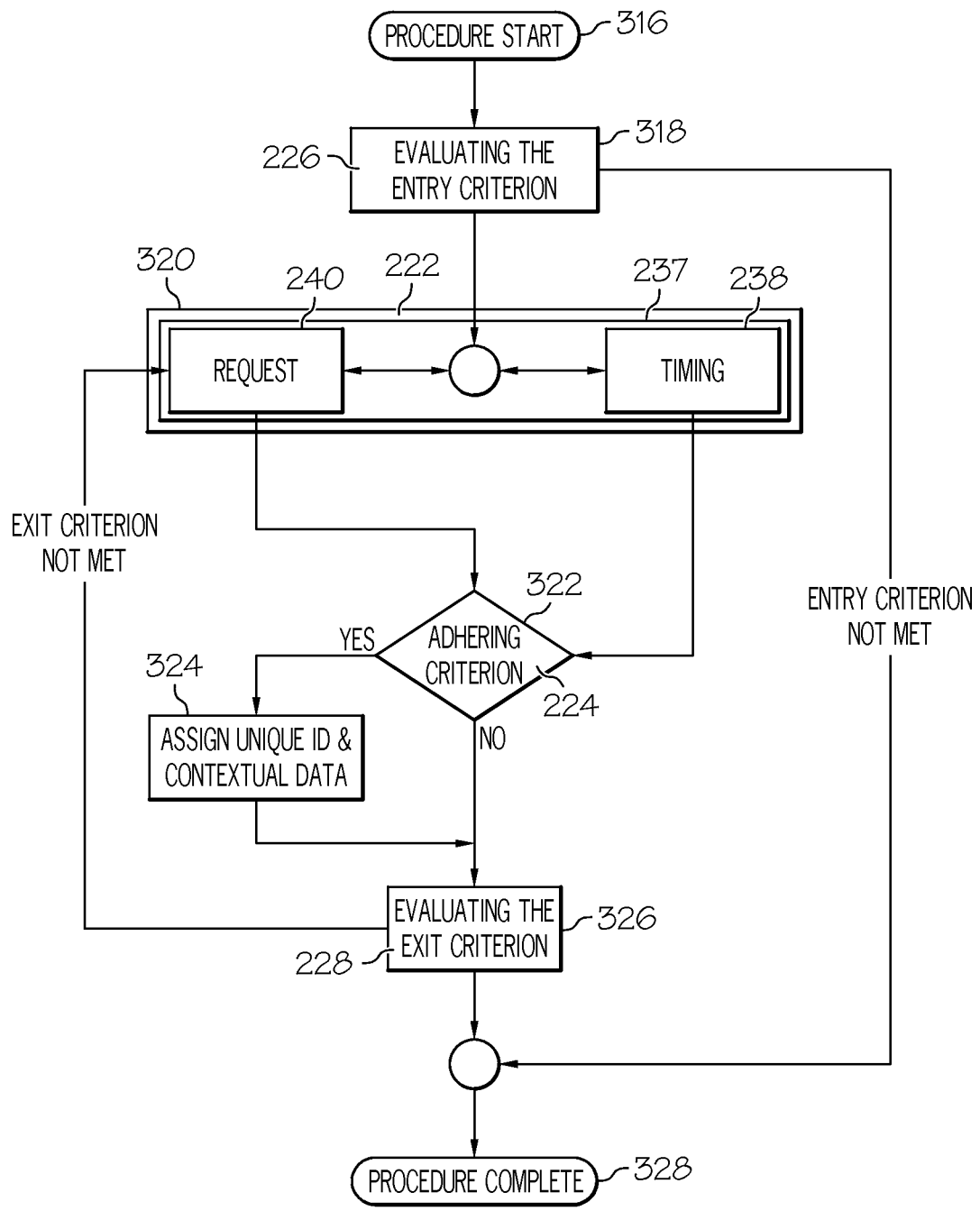
FIG. 8A shows a method for performing a structured collection procedure according to an embodiment of the present invention.

FIG. 8A shows a flowchart of the method for implementing and performing a structured collection procedure 70 to obtain contextualized biomarker data from a patient 12 according to an embodiment of the invention. It is to be appreciated that a number of structured collection procedures 70a-d (FIG. 2) prescribed in step 312 and implement in step 314 (FIG. 7A) may be stored in memory 110 (FIG. 3) of the device 24 and selected for execution at any desired time. For example, upon pressing a certain combination of the buttons 147, 149, the patient can select a desired structured collection procedures 70a-c and the date when to start a structured testing collection i.e., a set mode function. For example, a date range to choose from may be to begin the testing tomorrow and end at today +90 days, which the processor 102 can also recorded in the data file 145 (FIG. 4) as part of the setup data 163. In such an implementation, the processor 102 as instructed by the software 34 reads the setup data 163 for the selected structured collection procedure 70 and indicates on the display 108 that the device 24 is in a structured testing mode, for example, from one day before the chosen focused testing start date until the end of the structured collection procedure.

It should be appreciated that multiple structured collection procedures 70a-d can be executed sequentially or simultaneously at any given time. However, in one embodiment, the software 34 permits the user only to schedule another structured collection procedure 70 if the start date is later than the end date of the current structure collection procedure 70 being executed. The software 34 also permits the user to override a scheduled date for a structured collection procedure 70. If a structured collection procedure 70 is scheduled and the user enters the set mode function again, the software 34 causes the processor 102 to display the scheduled date on the display 108 as the default date; if the user exits the set mode without modifying the date, the previously scheduled date stays active. If a structured collection procedure 70 has started, the software 34 permits the user to enter the set mode and cause the processor 102 to cancel the current structured collection procedure 70. Upon cancellation, in one embodiment, the software 34 causes the processor 102 to de-tag (e.g., null the unique identifiers 167) the data records 152 in the data file 145 for the data collected for the cancelled structured collection procedure 70.

Upon reaching the procedure start in step 316 (FIG. 8a), the processor 102 evaluates the whether entry criterion(s) 226 is met in step 318 to begin the structured collection procedure 70 selected to obtain biomarker data to address a predefined use case or question (e.g., use case parameter 220). In step 320, the processor 102 specifies requests 240 according to their associated timing 238 for each event 237 in the schedule of events 222 for the structured collection procedure 70. It is to be appreciated that the schedule of events 222 provides a sampling plan for biomarker data collection that is performed by the processor 102 to obtain biomarker data in a predefined context. In performing the schedule of events 222 in step 320, the software 34 causes the processor 102 to assign a unique identifier (e.g. incremental count) 167 in a date record 152 which corresponds to each event 237 in the structured collection procedure 70. Optionally, each criterion 226, 228, 224 may also be provide with a date time stamp 169 to indicate when such criterion was satisfied, if desired.

Adherence criterion 224 is then applied to the input received (e.g., biomarker data or information) in response to a request 240 to determine whether the input received meets the adherence criterion 224. When a structure collection procedure 70 has started, all data collected according to requests 240 in the structured collection procedure 70 and which satisfy the adherence criterion 224, if required in step 322, are then assigned (tagged) in the data file 145 by the processor 102 with the unique identifier 167 in step 324. It is to be appreciated that the unique identified also serves to associates the collected data e.g., data values 256 with their event 237, the request 240, and a date-time stamp 169 to indicate when the collection in response to the request 240 was received by the processor 102. While a structured collection procedure 70 is being executed, in one embodiment the software 34 permits the user to perform a measurement on the device 24 at any time without interfering with the episode.

In one embodiment, the software 34 permits reminders for biomarker measurements to be 'snoozed' as mentioned above for a period, such as for example, 15 minutes and up to a number of times, for non-critical measurements. In another embodiment, biomarker measurements or data entries that are performed close enough in time to a request 240 in step 320 are designed as valid measurements or data entry for the request 240 by the software 34. As such, the processor 102 will tag the associated data record 152 for the event 237 with the unique identifier 167 for such a biomarker measurement or data entry accordingly. In the case of biomarker measurements, if the measurement is accepted as valid for the request 240, the software 34 causes the processor 102 to prompt the user to input additional information if needed by the structured collection procedure 70 to provide context 252 for data resulting from the request 240. Such additional input, may include, for example, a rating of energy level from 1 to 5, where 1 is low and 5 is high; meal size from 1 to 5 where 1 is small and 5 is large, and exercises from yes or 1 to mean over 30 minutes, and no or 2 to mean less than 30 minutes. Such additional information or contextual information 156 when inputted via the user interface 146 is stored by the processor 102 in the data file 145 associated with the unique identifier 167 for the data event request 240 requiring the additional information also in step 324.

In one embodiment, biomarker measurements determined by the processor 102 as not being close enough in time to the data event request 240 defined by the structured collection procedure 70 will not be tagged with a unique identifier 167 in the data file 145 by the processor 102. Such is illustrated in the shown data file 145 with request 240d and data values 256d not being associated with a unique identifier 167 e.g., <null>. An example of a definition of 'close enough in time to the collection procedure' as instructed by the structured collection procedure 70 and/or software 34 to cause the processor 102 to make such a determination may be defined as being relative to a prescheduled time or a snoozed time. For example, for pre-prandial measurements up to 15 minutes in anticipation is acceptable; for post-prandial measurements, up to 10 minutes in anticipation is acceptable; and for bedtime measurements, up to 15 minutes in anticipation is acceptable. Other definitions may be provided in other structured collection procedures 70 and/or software 34.

In step 326, the processor 102 then evaluates whether the exit criterion 228 for the selected structured collection procedure 70 is satisfied. If not, then the processor 102 continues with performance the schedule of events 222 until the exit criterion 228 is satisfied. Upon satisfying the exit criterion 228, the collection procedure 70 ends in step 328. In one embodiment, the structured collection procedure 70 may also end if in step 318, the entry criterion 226 is also not met.

In some embodiments, the structured collection procedure 70 can be configured for performance as a paper tool 38; diabetes software 34 integrated into a collection device 24 such as a blood glucose meter 26; diabetes software 34 integrated into the computing device 36, such as a personal digital assistant, handheld computer, or mobile phone; diabetes software 34 integrated into a device reader 22 coupled to a computer; diabetes software 34 operating on a computer 18, 25 such as a personal computer; and diabetes software 34 accessed remotely through the internet, such as from a server 52. When diabetes software 34 is integrated into a collection device 24 or a computing device 36, the diabetes software 34 can prompt the patient to record diary information such as meal characteristics, exercise, and energy levels. The diabetes software 34 can also prompt the patient to obtain biomarker values such a blood glucose values.

GUI Interface Providing a Selectable Structured Collection Procedure

Figure 8B:
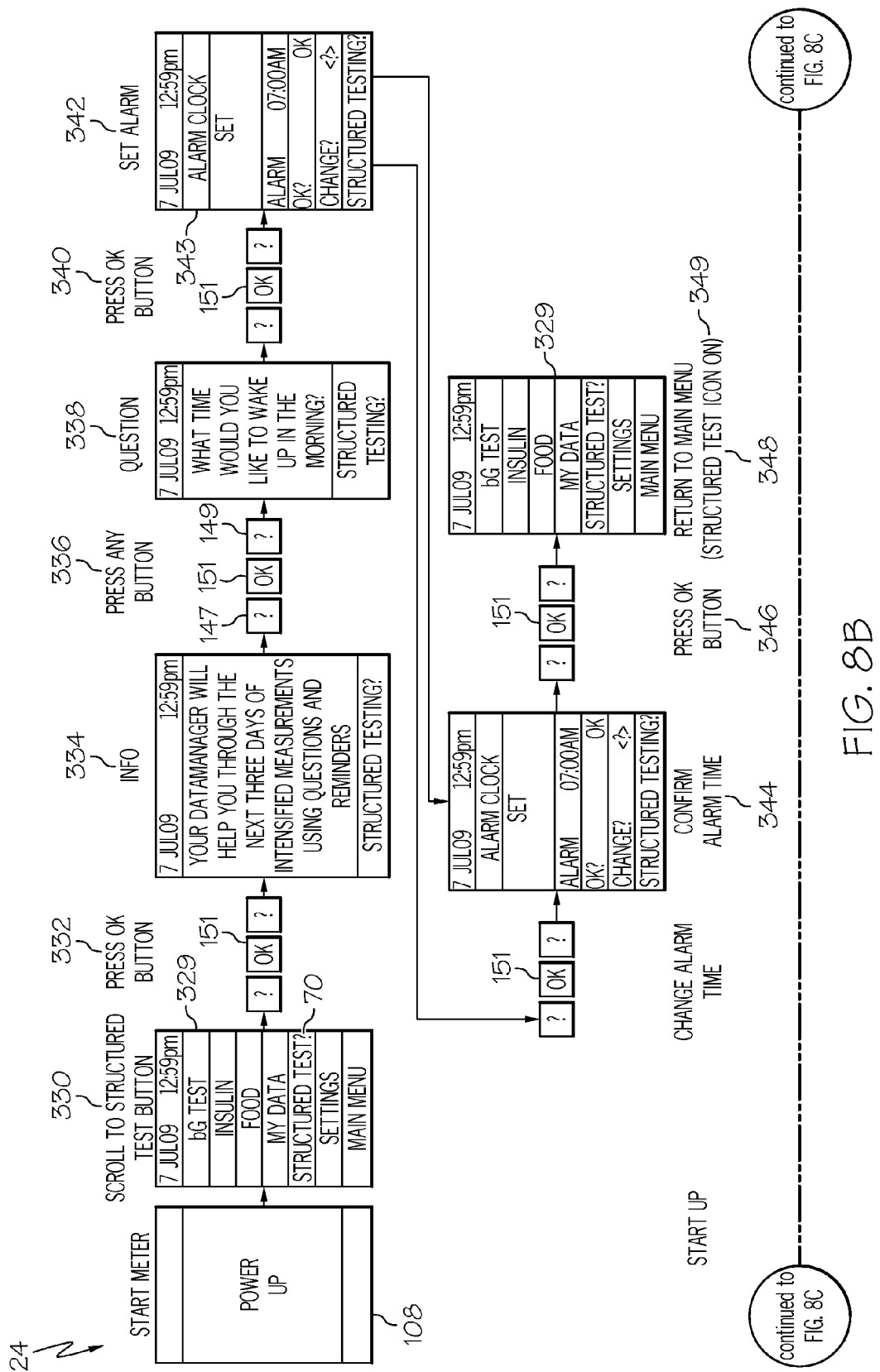
FIGS. 8B and 8C show a method of implementing a structured collection procedure via a graphical user interface provided on a collection device according to an embodiment of the present invention.
Figure 8C:
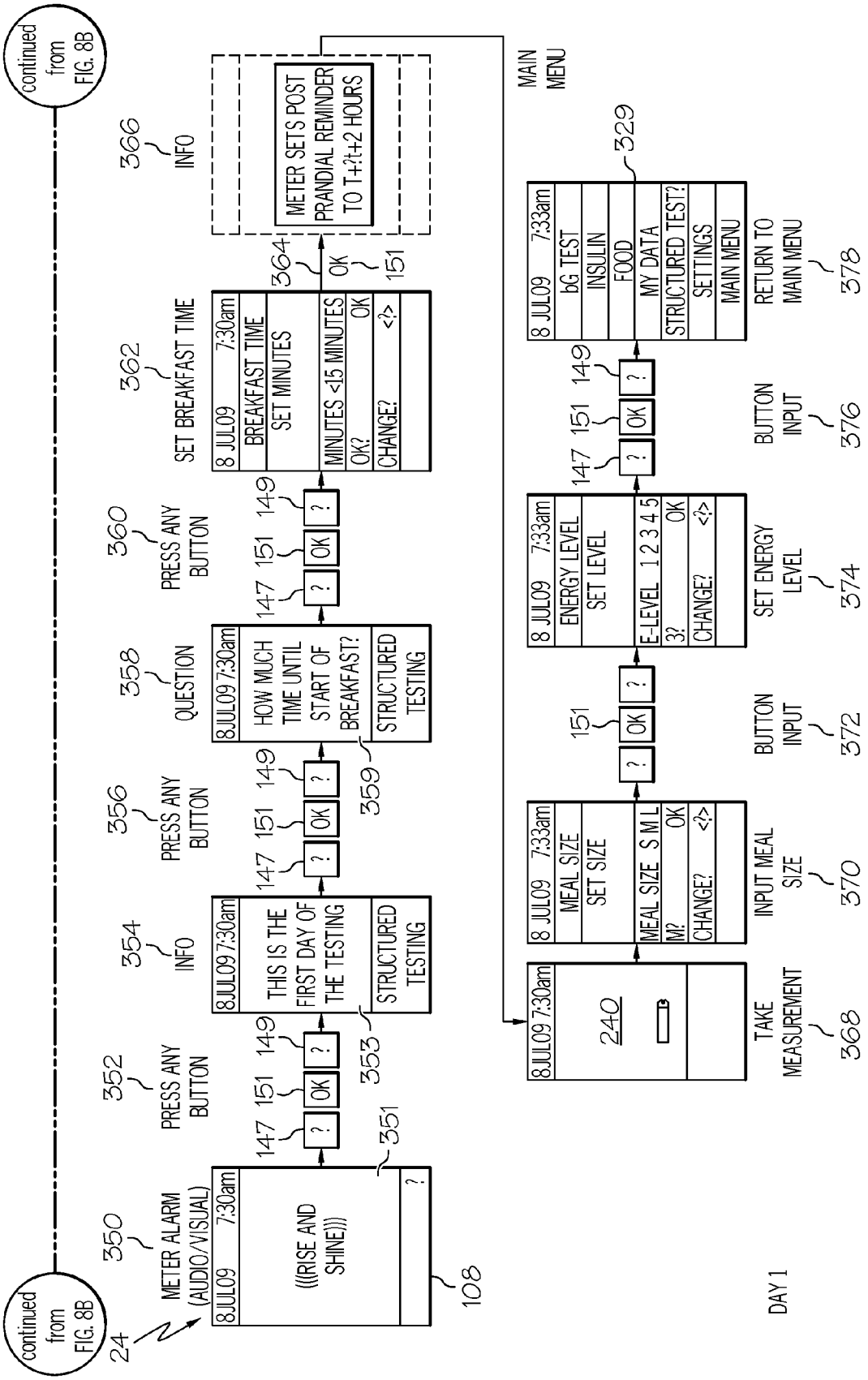

FIG. 8B shows a method of implementing the structured collection procedure via a graphical user interface provided on a collection device 24, which when executed on the collection device, cause the processor 102 to perform the following steps. Upon pressing a certain combination of the buttons 147, 149, the patient 12 can scroll to the structured collection procedure 70 available for selection in a list 329 provided by the processor 102 on the display 108 of the collection device 24 in step 330. If desiring to start the structured collection procedure, the patient 12, for example, selects via pressing an OK button 151 in step 332, the desired structured collection procedure 70. In this example, the entry criteria 226 (FIG. 6) of the structured collection procedure 70 provides information in step 334 which the processor 102 displays to the user on the display 108. After reading the displayed information, the user presses any button in step 336 in which the next procedure in the entry criteria 226 is performed by the processor 102. In this illustrated example, as part of the entry criteria 226, a question is then asked in step 338 by the processor 102. If the patient 12 is still desirous of starting the structured collection procedure, the patient 12 selects the OK button 151 in step 340; otherwise, any other press via button 147, 149 will cause the processor to go back to the list 329, thereby stopping the set-up procedure for the structured collection procedure 70.

After the patient 12 presses the OK button 151, the processor 102 in step 342 will provide on the display 108 an alarm clock 343 for setting the time to begin the selected structured collection procedure 70. It is to be appreciated that all the required events 237 for biomarker sampling, patient information, etc., is automatically schedule by the processor 102 in accordance with the schedule of events 222 for the structured collection procedure 70 in which timing, values, questions, etc., therein may have been adjusted by the clinician 14 as discussed previously above in reference to FIGS. 7A and 7B. Therefore, other than entering the start time as permitted by the entry criteria 226, no other parameter adjustments in the structured collection procedure 70 is required by the patient 12 (or permitted in one embodiment).

In the illustrated embodiment, the patient in step 344 can adjust the start time of the structured collection procedure for the next day, e.g., Day 1, via buttons 147, 149. Upon confirming the start time in step 346 via pressing the OK button 151, the start time is recorded in memory 110 as part of the setup data 163 in the data file 145 (FIG. 4) for the structured collection procedure 70 by the processor 102. The processor 102 then displays the selection list 329 on the display 108 in step 348, thereby completing the set-up procedure, which satisfies the entry criterion 226, and indicates on the display 108 that the collection device 24 is in a structured testing mode 349.

It should be appreciated that in on embodiment multiple structured collection procedures can be executed sequentially or simultaneously at any given time, and hence in one embodiment the mode 349 provided on the display 108 will indicated which structured testing is being performed. However, in one embodiment, the software 34 does not permits the user to schedule another structured collection procedure, unless the start date is later than the end date of the current structured collection procedure being executed via the user interface 146. It is to be appreciated that processor 102 may re-schedule the following structured collection procedures automatically if the current structured procedure is still running due to the exit criteria 228 not being met. The software 34 in another embodiment may also permit the user to override a scheduled date for a structured collection procedure. If a structured collection procedure is scheduled and the user enters the set mode function again, the software 34 causes the processor 102 to display the scheduled date on the display 108 as the default date; if the user exits the set mode without modifying the date, the previously scheduled date stays active. If a structured collection procedure has started, the software 34 permits the user to enter the set mode and cause the processor 102 to cancel the current structured collection procedure, if desired.

In step 350, an alarm condition 351 can be provided by the processor 102 the next day (as indicated by the symbol Day1) as was set in the above-mentioned procedure the previous day (as indicted by the symbol Start Up). Upon the user selecting any button 147, 149, 151 in step 352, the processor 102 as instructed by schedule of events 222, provides a first scheduled event 237 which is information 353 to be displayed on display 108 in step 354, which the patient 12 acknowledges with any button 147, 149, 151 being pressed in step 356. Next in step 358, the processor 102 is instructed by the schedule of events 222 to execute a second scheduled event, which is to display on the display 108 a question 359 for the patient, which the patient 12 acknowledges with any button 147, 149, 151 pressed in step 360. In the illustrated embodiment, the patient in step 362 indicates the start time of breakfast in minutes from the wake up alarm 351 previously acknowledged in step 352. Upon confirming the meal start time in step 364 to the processor 102, via pressing the OK button 151, the meal start time is recorded in memory 110. For example, the meal start time is recorded in the data file 145 in the associated data record 152 as data for the event 237 by the processor 102. Additionally, in step 366, the processor 102 displays to the patient 12 the information regarding the timing for the next schedule event as a reminder. In step 368, upon reaching the next scheduled event indicted by the schedule of events 222, the processor 102 provides a request 240 on the display 108 for the patient to take a measurement, e.g., a blood glucose measurement. Additionally, in step 370, the processor 102 also makes a request 240 for information on the size of the meal that is to be ingested as required by the schedule of events 222 in order to provide contextual information 156 to the measurement value.

As mentioned above previously, for each event the software 34 causes the processor 102 to assign a unique identifier (e.g. incremental count) 167 (FIG. 4) to the data of each request 240 provided in the schedule of events 222 which meet the adherence criterion 224 in the associated date record 152 for the event 237. Therefore, while the structured collection procedure is being executed, the software 34 permits the user to perform a measurement on the collection device 24 at any time outside the schedule of events 222. Such a measurement since not being performed according to a request 240 will not be evaluated for the adherence criterion 224, and thus will not be provided with a unique identifier 167 in the date file but will only be provided with a date-time stamp and its measurement value. Such data is still recorded in the data file 145, as such data may still be useful for another analysis.

In another embodiment, the software 34 also permits reminders for biomarker measurements, such as provided in step 238. For example, in one embodiment, the processor 102 provides an alarm and/or alert message for a reminder via the indicator 148 and/or on the display 108, respectively, to provide a measurement. For example, at the time 238 of a particular request 240 for taking a biomarker measurement (or reading), the processor 102 prompts the patient 12 by al least displaying on the display the message, "It is now time for your reading." An audible alarm and/or tactile alarm (vibrations) can be provided by the processor 102 via indicator 148 in another embodiment. For example, in one embodiment, the collection device 24 will provide such a prompt even when already powered on, such as by the patient 12 for another reason, e.g., to conduct a non-scheduled event, when in, for example, a window of time in which to take the requested measurement/reading, or even when powered downed, such as in a standby mode, by waking up to provide the reminder via the prompt. In another embodiment, the provided reminder or prompt can be 'snoozed' for a pre-defined period as mentioned above, that still falls within the window of time in which to take the requested (critical) measurement/reading such as for example, 15 minutes or any other such suitable time that falls in the window of time. It is to be appreciated that the snooze feature for a measurement/reading that is considered critical to the structured testing procedure 70, e.g., a measurement/reading needed for helping to address the medical use case or question, needed to meet adherence criteria 224, and/or needed in subsequent analysis for some determination, etc., the snooze feature will not extend the request 240 beyond the window of time provided by the collection procedure 70 via, e.g., adherence criterion 224 for the request 240. For example, in one embodiment one or more events 237 in the schedule of events 222 can be pre-defined as critical as well as being a primary sample via use of the options parameter 232 (FIG. 7B) provided in the structured collection procedure 70. For example, an event 237 which is designated as critical is one that cannot be missed, but if missed can be replaced by another sample already in the date file 145. In still another embodiment, the snoozing can be up to a number of times, for non-critical measurements. For example, certain events 237 in the structured collection procedure 70 could be designated as having a non-critical request 240, which can be snoozed, such as via selecting such an option that is provided as one of the options parameter 232 (FIG. 7B). The options parameter 232 in this embodiment could for example provide the snooze option as well as a selectable time interval (e.g., 1-60 minutes, etc.) and a selectable number of times (e.g., 1-5, etc.) that the user is permitted to snooze the request 240. In still another embodiment, the collection device 24 permits for an alarm shut off i.e., the indicator 148 if providing the reminder (audible, vibratory) can be shut off for the entire window of time via the user interface 146, but wherein processor 102 still accepts the measurement/reading as long as it is made in the window of time. In still another embodiment, the collection device 24 provides a skip reading option also received by the processor 102 via a selection entered using the user interface 146, e.g., from a list of selectable options, such as for example, snooze, alarm shut off, skip reading, provided on the display 108, in which again no reminder/prompt will be provided as patient 12 has indicated to the processor 102 that he/she does not want to take that particular requested measurement/reading. It is to be appreciated that selecting the skip reading selection option can result in an adherence event 242 resulting in further processing, such as discussed previously above in early sections, if adherence criterion 224 had been associated with the event 237 prompting the request 240.

In still another embodiment, the adherence criteria 224 can require biomarker measurements to be performed close enough in time to a data event request 240. Therefore, if such biomarker measurements are performed within the period specified by the adherence criteria 224, the processor 102 can indicate that the measurements or data entry for the event is acceptable and tags (i.e., assigns the unique identifier 167) the value of the biomarker measurement or data entry in the data file 145 accordingly. In the case of biomarker measurements, if the measurement is accepted as valid for the data event request 240 (i.e., meets the adherence criterion(s) 224), the schedule of events 222 may causes the processor 102 to prompt the user to input additional information if needed by the structured collection procedure 70, such as mentioned above regarding step 370 to provide contextual information 156 (i.e., context) to the measurement received in response to a request 240.

Such contextual information 156 when inputted via the user interface 146 can be stored by the processor 102 in the data file 145 associated with the unique identifier 167 for the data event request 240 requiring the additional information. Biomarker measurements determined by the processor 102 as not being close enough in time to the data event request 240 as defined by the adherence criteria 224 will not be tagged in the data file 145 by the processor 102. Such is illustrated in the shown data file 145 (FIG. 4) with data event request 240d and data values 256d not being associated with a unique identifier 167. An example of a definition of 'close enough in time to the collection procedure' as instructed by the adherence criteria 224 to cause the processor 102 to make such a determination may be defined as being relative to a prescheduled time or a snoozed time. For example, for pre-prandial measurements up to 15 minutes in anticipation is acceptable; for post-prandial measurements, up to 10 minutes in anticipation is acceptable; and for bedtime measurements, up to 15 minutes in anticipation is acceptable. Other definitions may be provided in other adherence criteria 224 for other events in the schedule of events 222 as well as in other structured collection procedure.

Figure 9:
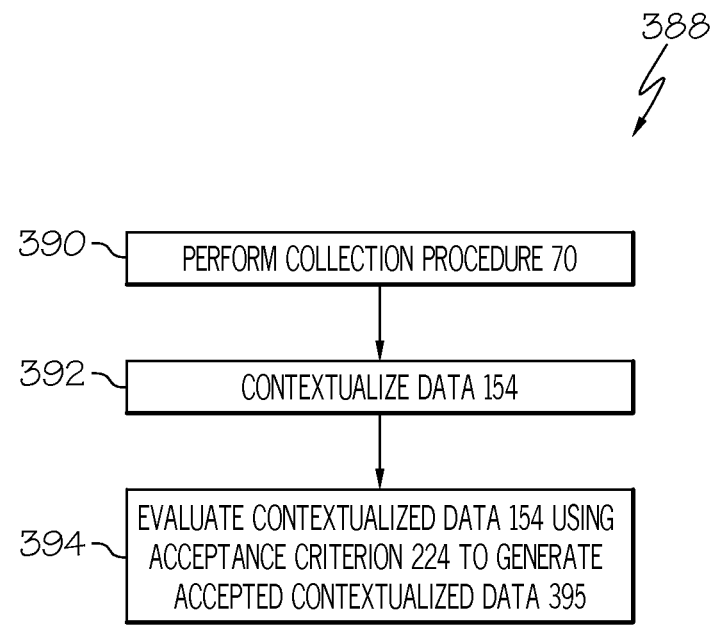
FIG. 9 shows a method for performing a structured collection procedure to obtain contextualized biomarker data from a patient according to another embodiment of the present invention.

In the illustrated embodiment, the user uses the buttons 147, 149 to scroll to a selection, which is entered by the processor in the data record 152 for the associated request 240 via pressing Okay button 151 in step 372. In one embodiment, the meal size can be indicated via a number range, such as for example, from 1 to 5, where 1 is small and 5 is large. In the illustrated embodiment, additional input for contextual information 156 regarding a rating of energy level from 1 to 5, where 1 is low and 5 is high is requested in step 374, which is entered in the data file 145 as mentioned previously above via the processor 102 receiving input for the request 240 by using the user interface 146 in step 376. In other embodiment, other contextual information 156 may include indicating whether the patient exercised and/or how long. For example, the user interface 146 may be use in which yes or 1 to mean over 30 minutes, and no or 2 to mean less than 30 minutes. In the illustrated embodiment, as the exit criterion 228 is now meet via successfully performing steps 368-376, the structured collection procedure 70 ends in step 378, wherein the processor 102 again displays the list 329, such that the patient 12 may perform other tasks on the collection device 24 if so desired. Reference is now made to FIG. 9 hereafter.

Method of Contextualizing Biomarker Data

FIG. 9 depicts a method 388 of contextualizing biomarker data for diabetes diagnostics and therapy support according to an embodiment of the invention. It is to be appreciated that in the previous embodiments discussed above with reference to FIGS. 8A and 8B, the contextual information 156 was requested and recorded with the associated biomarker value by the processor automatically during the structured collection procedure 70. However, in embodiments where such automation is not provided on the collection device 24, and the patient is using a paper tool 38, the collection data can be later associated with its contextual information 156 after, for example, the structured collection procedure 70 is performed in step 390 to create at least data event values 256. If not already done by the collection device 24, such as in the case of a device with limited memory and processing power or when recordings are made on paper tool 38, such data may be provided to another one of the devices 18, 25, 36 that is running the software 34 and has the ability to associate at least the data event values 256 (FIG. 4) with their respective data event requests 240. This associating of at least the data event values 256 with their respective data event request 240, the date-time stamp 169, and the contextual information 156 results in contextualized (self-monitoring) data 170 in step 392.

It is to be appreciated that data as used in structured testing according to the present invention deals with the prospective collection of contextualized data. Considering FIG. 10A, in this example, the inherent advantage of context becomes clear when one considers the utility of having a subway map on the left-hand side without context and one on the right-hand side with context, which makes it possible to easily navigate the system and travel from one place to another. In a similar manner, contextualization can play an important role in diabetes. Context associated with data, for example, can be due to therapy, an event (such as meals, exercise, an event 237, request 240, etc.), and time of request for data collection itself (e.g., timing 238). As such, any data collected by the patient with measured values can be contextualized by being associated with one or more the above mentioned factors e.g., therapy, events, and time, each of which are discussed further hereafter.

Therapy can be defined, for example, as an on-going treatment intended to alleviate the patient's impaired glucose control. This treatment generally involves anti-diabetic agents such as insulin, oral medications, and diet and exercise. A therapeutic (or a therapeutic combination) has a specific pharmacodynamic effect on a patient's glycemia owing to different mechanisms of action. A change in either the dose(s) of the therapeutic(s) or a change in the therapeutic(s) itself, will lead to a change in the patient's glucose control. Consequently, the collected bG data is strongly linked to underlying therapy and dose and this information is used to contextualize the data. A change in dose or therapeutic will lead to a different context. It is to be appreciated that the therapy context can be set by the clinician 14 in consultation with the patient at the time of designing the collection procedure 70, such as discussed previously above with regards to FIG. 5A.

In one embodiment, the events 237 in a collection procedure 70 can include specific conditions around bG measuring points that play a role in altering the patient's normal glucose levels. As mentioned previously above, events 237 can be meal or exercise based, and are pertinent for data contextualization. In this context, the underlying assumption is that the patient operates, more or less, under a well-defined schedule. At the time of creating the collection procedure 70, the patient 12 can discuss lifestyle events with the clinician 14 so that the collection procedure 70 can be tailored according to the needs of the patient 12. As an example and with reference to FIG. 10B, consider a typical collection procedure 70 whereby the patient 12 does not exercise regularly so that the majority of the events are meal based events that consist of breakfast, lunch, and dinner. Such a lifestyle of the patient 12 leads to six candidate points for bG measurement (pre and post for each of the meals) for the schedule of events 222 in the collection procedure 70. During the process of creating/customizing (FIG. 5A and/or FIG. 7B) of the collection procedure 70, the clinician 14 may specify that the patient collect one or more or all of these points as per the schedule of events 222 of the collection procedure 70. Any data collected in addition to these points, i.e., outside the requirements of the collection procedure 70, can be classified as non-collection procedure readings by the processor 102. In a similar manner, for a Type 1 diabetic patient that exercises regularly, the clinician 14 can tailor/customize a collection procedure 70 to include additional measurements around the exercise event. The event information, in this example, is then used to contextualize the data in an appropriate manner depending on the event 237.

Time represents the actual time at which a measurement is made and is in absolute terms, e.g., date-time stamp 169 (FIG. 4). Additionally, time can also be represented in terms of deviations, i.e., offset from a particular event. As an example, a postprandial reading is taken at a specific time after a meal and this time may be different across different days. This scenario arises as the patient may not be able to take an event based reading t the same time every day. Consequently, there is a distribution of times at which the same measurement has been made at different days. The knowledge of this distribution can become useful for analysis of such timing as well as the parameter timing 238 in the collection procedure 70.

Additionally, with the contextualized data 170, the physiological state of the patient 12 at the time of the measurement can be described. The patient's physiological state can influence a biomarker value, so knowledge of the patient's physiological state aids in the understanding of a biomarker value. The biomarker data can be contextualized because the biomarker data is collected in the context of predetermined events such as last time of meal, meal type, meal distribution, exercise information, sleep quality, sleep duration, waking time, and stressors such as illness and the like. Time-resolved data permits interpreting the biomarker data in context with other information, such as compliance with a structured collection procedure 70 and patient lifestyle events.

Referring again to FIG. 9, the contextualized data 170 is evaluated using adherence criterion (or criteria) 224 to generate accepted contextualized data 395 that meets the adherence criterion 224 in step 394. As the adherence criterion 224 can provide a basis for comparison of a data event value 256 with a standard, so the data event value can be either accepted and used or rejected and not used, the adherence criteria 224 can be used to filter data in one embodiment. In another embodiment, step 394 may precede step 392.

Figure 11:
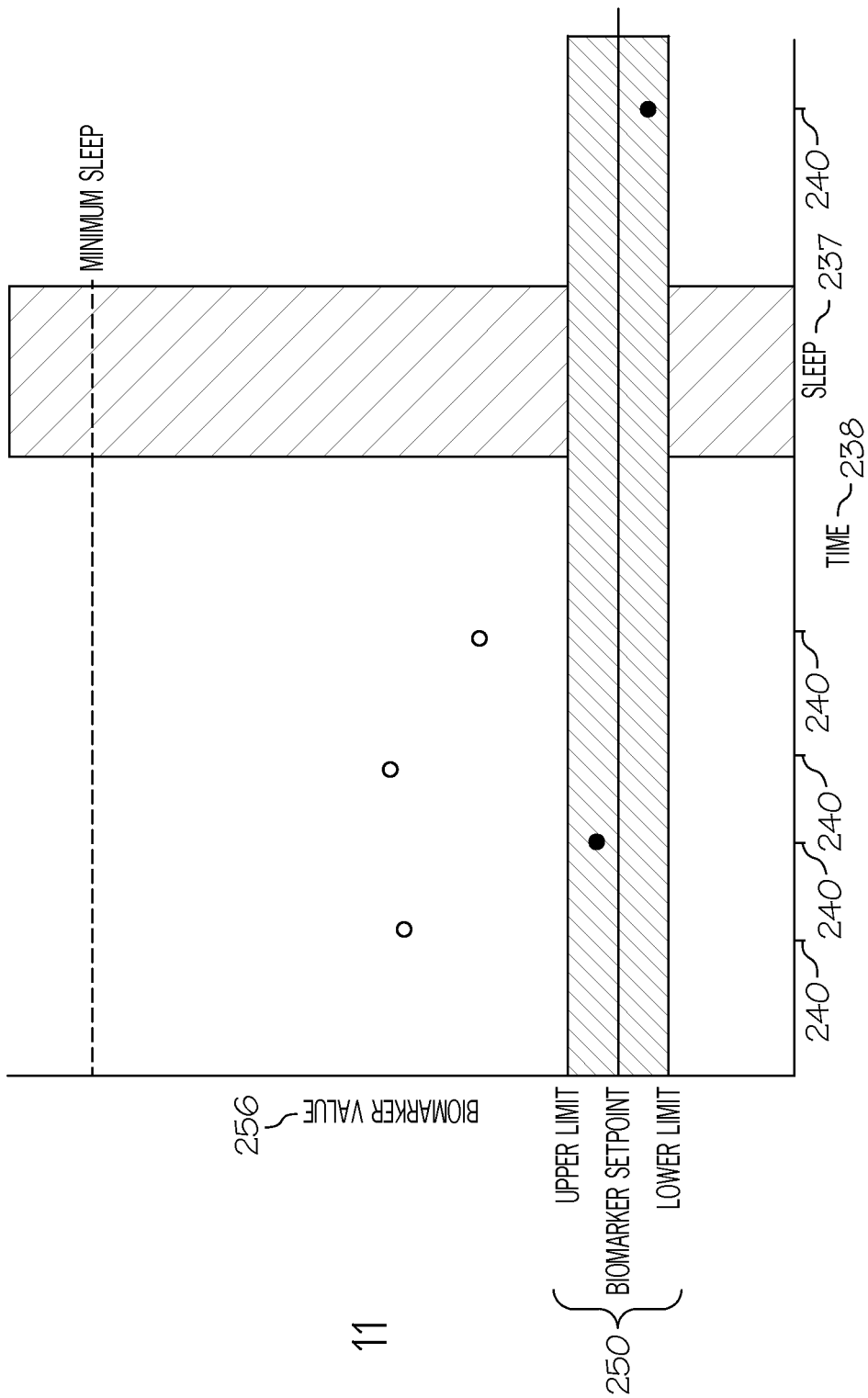
FIG. 11 depicts a diagram of accepted contextualized data intermingled with non-acceptable contextualized data according to an embodiment of the present invention.

FIG. 11, for example, shows a diagram of accepted contextualized data 395 intermingled with non-acceptable contextualized data 397. The diagram vertical axis shows biomarker values 256 including context 252 in the form of a biomarker setpoint, a biomarker upper limit, and a biomarker lower limit. The diagram horizontal axis shows performance times 238 of measurement requests 240 and a sleep period event 237 in which the actual sleep surpassed a recommended minimum amount of sleep as indicated by the dashed line. The accepted contextualized data 395 is that which met the adherence criterion 224. The non-acceptable contextualized biomarker data 397 are either not within the structured collection procedure 70 or did not meet adherence criterion 224. By excluding the non-acceptable contextualized biomarker data 397, the accepted contextualized biomarker data 395 can help improve decision-making Statistical techniques can be used to view the accepted contextualized biomarker data 395 in a form that conveys additional information to a clinician 14. Examples of statistical techniques include regression methods, variance analysis, and the like. Hereafter further details about another embodiment of the software 34 are provided.

Software

As mentioned above in previous sections, the software 34 can operate on the patient computer 18, the collection device 24, a handheld computing device 36, such as a laptop computer, a personal digital assistant, and/or a mobile phone; and paper tools 38. The software 34 can be pre-loaded or provided either via a computer readable medium 40 or over the public network 50 and loaded for operation on the patient computer 18, the collection device 24, the clinician computer/office workstation 25, and the handheld computing device 36, if desired. In still other embodiments, the software 34 can also be integrated into the device reader 22 that is coupled to the computer (e.g., computers 18 or 25) for operation thereon, or accessed remotely through the public network 50, such as from a server 52. Additionally, one or more collection procedures 70 can be provided as part of the software 34, provided as updates to the software 34, or provide as individual files which can be operated on and used by the software 34.

Figure 12:
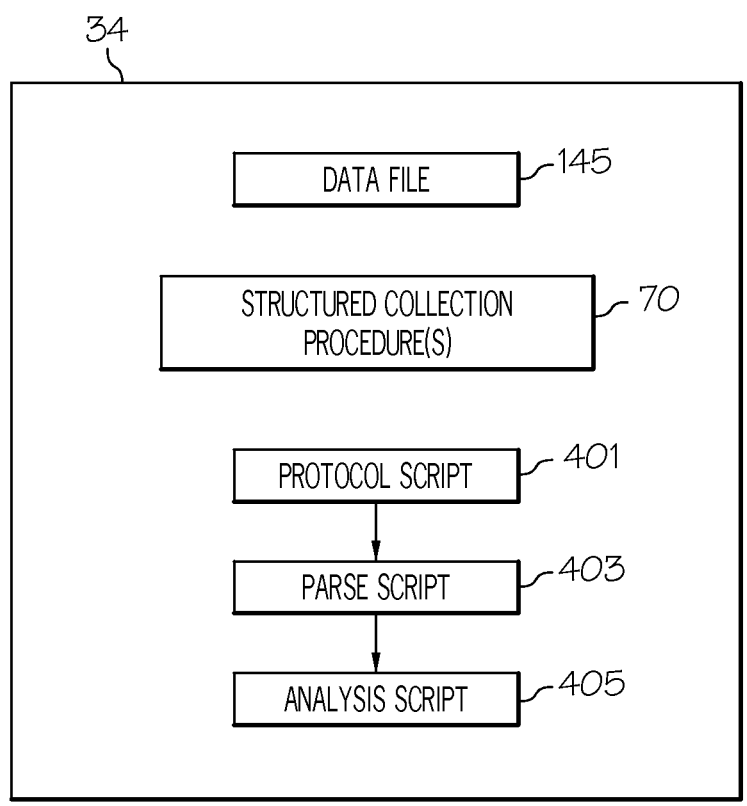
FIG. 12 depicts elements of software according to an embodiment of the present invention.

In the embodiment discussed hereafter, the software 34 runs on the collection device 24 and provides three basic elements: one or more structured collection procedures 70, data file 145, and one or more scripts. As the features of the structured collection procedure 70 and data file 145 are the same as previously discussed above no further details is provided. The one or more scripts are small independent programs that reside on the collection device 24 and each can perform a specific set of tasks. Such scripts can include a protocol script 401, a parse script 403, and an analysis script 405 such as depicted by FIG. 12, each of which are discussed in detail in the following paragraphs.

Protocol Script

The protocol script is a script that actually enables the execution of the collection procedure 70 by the processor 102 on the collection device 45. At the time of initiation of collection procedure 70, the protocol script in one embodiment causes the processor 102 to create a data structure that outlines the amount of data expected as outlined by the collection procedure 70. In another embodiment, the data structure can have a variable size, or be a fixed size but with a buffer e.g., an array in the data structure, should additional data be collected during the collection procedure 70. For example, such have buffer can account for situations when the collection protocol 70 can be extend, if desired, or needs to be extended due to not meeting a desired condition, e.g., a patient biomarker value has not reached a desired value, such as, for example, up to a maximum size of allocable memory for the data structure in memory 110 of the collection device 24. This data structure, such as data file 145, stores at a minimum the time of initiation of the collection procedure 70, actual measurement of biomarkers, such as data event value 256, and time of the measurements, such as date-time stamp 169, and optionally all other information used for additional contextualization, such as the contextual information 156, and request 240, such as meals, exercise, etc. As an alternative embodiment, one can also consider the data structure to be a calendar that is generated by the clinician 14 which can include details in terms of the day, and the time of day when a measurement needs to be made. This calendar feature also enables the patient to see readily when he has to make the next measurement. The protocol script also causes the processor 102 to perform all of the functions necessary for the processor 102 to execute the collection procedure 70. Once appropriate data is collected, e.g., a successful run of the collection procedure 70, the protocol script causes the processor 102 to mark the data structure with a completion flag 257 in one embodiment or provides it as state condition of the software 34 in another embodiment and passes control of the processor 102 as provided in the software 34 to the parse script. In the former embodiment, the completion flag 257 can also be used to provide information regarding the reason for ending/terminating, such as to identify the type of completion (end, logistical (timeout), adherence terminated, etc.). For the latter embodiment, as one or more structured collection procedures 70 may be loaded onto the collection device 24 at the factory as mentioned previously above, providing state conditions for each collection procedure 70 in the software 34 helps to support the requirement that the procedure only be available after authorization by the clinician 14. In one embodiment, such state conditions of each collection procedure 70 can be tracked by the software 34 and can include one or more of a 'Dormant' state, an 'Authorized' state, a 'Pending' state, an 'Active' state, and a 'Completed' state. The Dormant state is useful when the collection device 24 is shipped with one or more embedded collection procedures 70, but until authorized for use, such as described above previously, cannot be use (or seen) by the patient 12 on the collection device 24. In this case, the collection procedure 70 is said to be in a Dormant state. The Authorized state is when the collection procedure 70 becomes usable after the clinician 14 authorizes it for use on the collection device 24. During this state, the collection procedure 70 can be configured (e.g., by the clinician) and initiated for start as also configured, e.g., via selection by the clinician, the patient 12, or by a start date. The Pending state is when a start date is set, but prior to execution, e.g., in which the collection procedure 70 is waiting for some unknown time until the entry criterion 226 is met before executing the schedule of events 222. Once the collection procedure 70 begins executing on or after the start date, via meeting the entry criterion 226 in one embodiment, the collection procedure is said to be in the Active state in which at least the schedule of events 222 is being implemented by the processor 102. The Completed state functions in a similar manner as to the completion flag 257 when the collection procedure 70 has ended as mentioned above previously.

Parse Script

The parse script is the script that causes the processor 102 to parse the contextualized data, such as e.g., contextualized data 395 (FIG. 11), once the collection procedure 70 data collection is complete. The parse script causes the processor 102 to try to resolve any exceptions (e.g., in real time, i.e., as the procedure 70 is being executed) that may have arisen at the time of execution of the collection procedure 70, e.g., for only critical data events 237 in the collection procedure 70 (e.g., a mandatory data collection for a biomarker value) in one embodiment. If at the end of the execution of the parse script exceptions remain for at least the mandatory data required for the collection procedure 70, then the parse script will cause the processor 102 to signify that appropriate data has not been collected. Consequently, the collection procedure 70 is marked by the processor 102 as incomplete via the completion flag 257 not being provided by the processor 102 in the data file 145. If there are no exceptions at the end of a parse script, e.g., at least for the critical events in one embodiment, and/or events designated as primary samples in another embodiment, and/or for all events in still another embodiment, the collection procedure 70 is marked complete via the processor 102 providing the completion flag 257 in data file 145, which contains the collected and contextualized data. The role of the parse script will be explained hereafter subsequently in a still another embodiment illustrating an execution stage.

Analysis Script

The analysis script causes the processor 102 to analyze the completed collection procedures 70 that have their own associated datasets, e.g. data file 145. The analysis performed by processor 102 according to the analysis script can be simple (mean glucose value, glucose variability, etc.) or it can be more complex (insulin sensitivity, noise assessment, etc.). In one embodiment, the collection device 24 can perform the actual analysis itself, or the analysis can be carried out on a computer, such as computer 18, 25. In one embodiment, the results from the analysis script can then be displayed either on the display 108 of collection device 24 by the processor 102 or on the display of a peripheral device. Reference to the scripts and program instructions of the software 34 are discussed hereafter with reference made to FIGS. 13 and 14 as well as to FIGS. 2 and 5B.

Collection Procedure Execution

Figure 13:
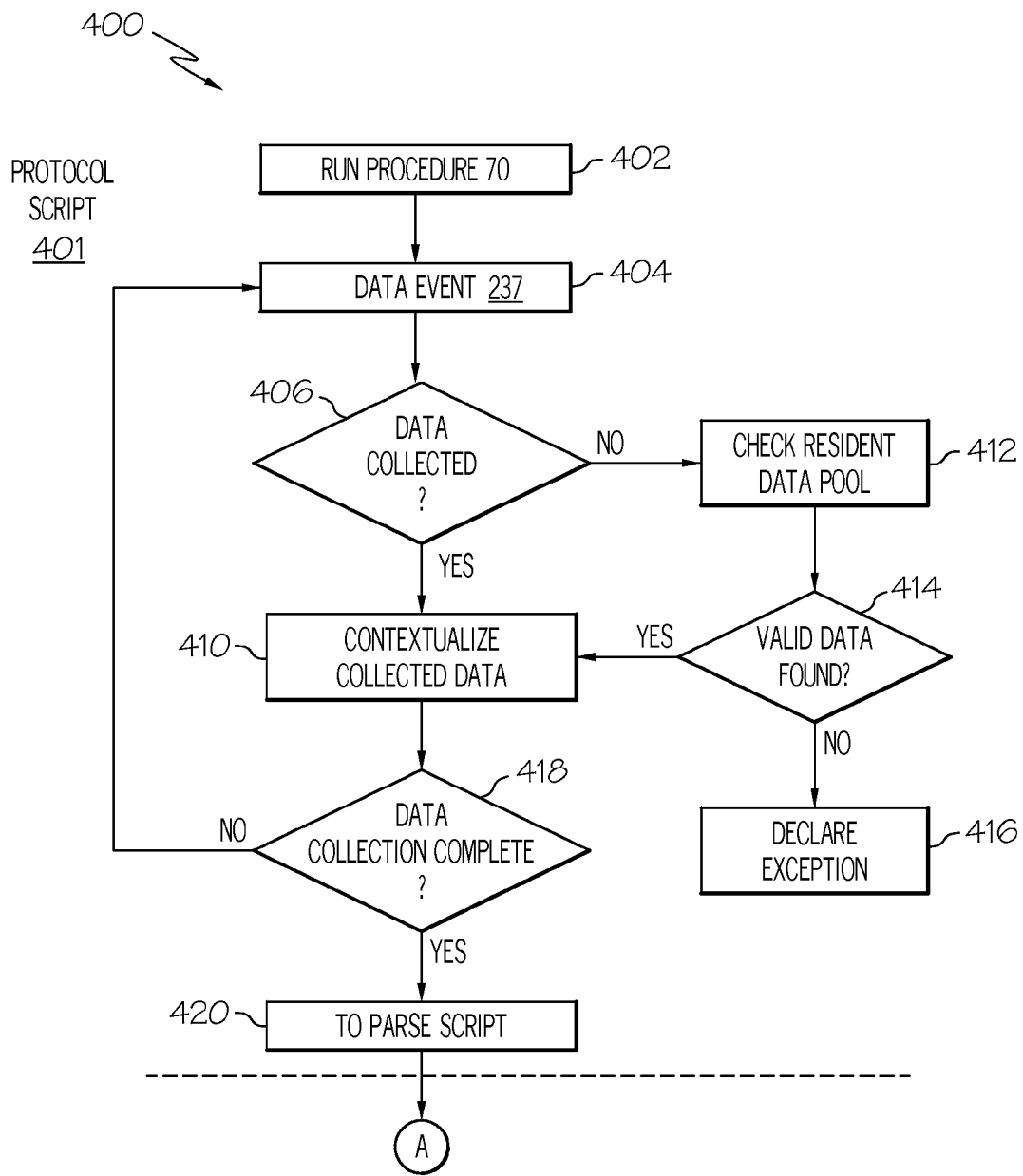
FIGS. 13 and 14 depict a collection procedure execution method according to an embodiment of the present invention.
Figure 14:
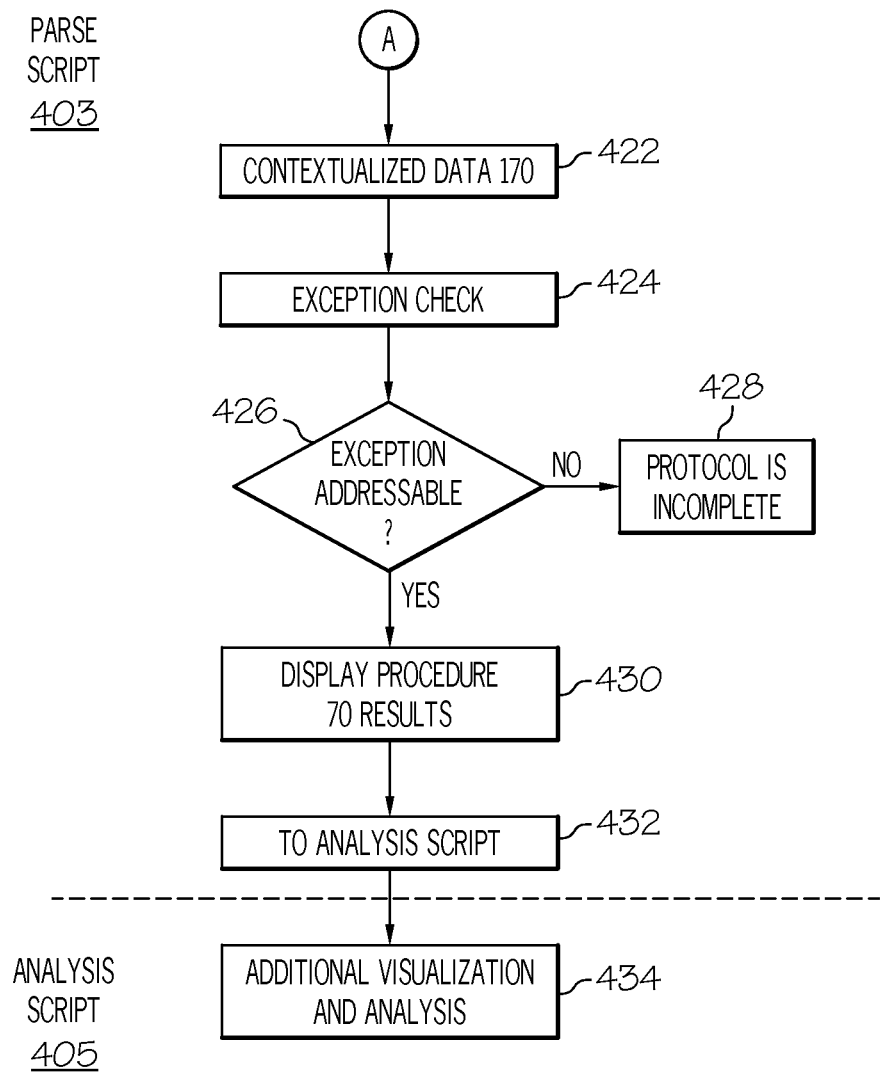

FIGS. 13 and 14 depict a collection procedure execution method 400 performed by the processor according to the program instructions of the software 34 using the above mentioned scripts during a collection procedure 70. The dash-dot lines indicate the boundary between the different domains of the different scripts and are the boundaries across which exchange in control takes place. It is to be appreciated that the hereafter disclosed embodiments of the present invention can be implemented on a blood glucose measuring device (such as a meter) that has the capability to accept one or more structured collection procedures 70 and the associated meter-executable scripts discussed above.

Figure 10B:
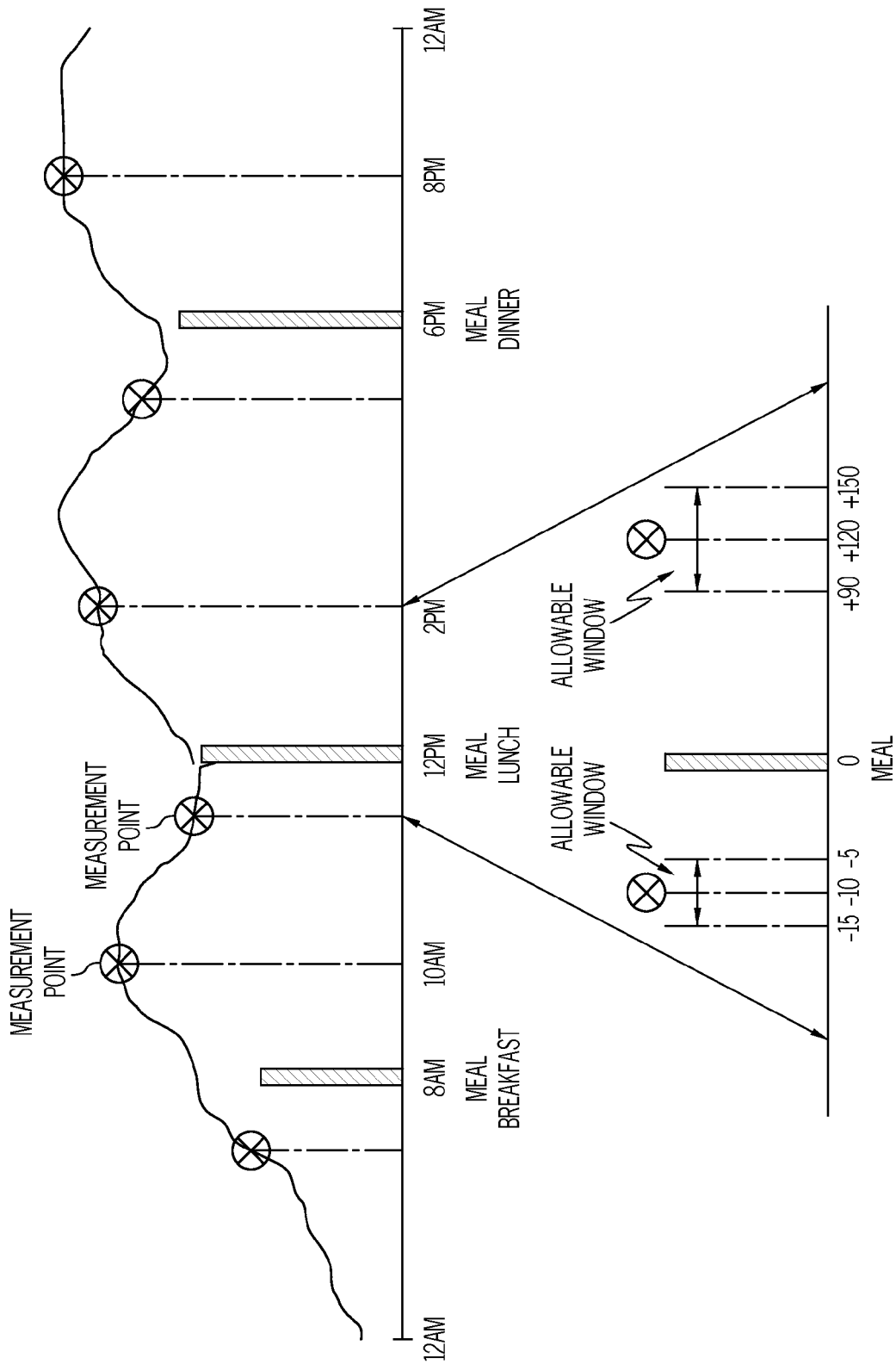
FIG. 10B depicts a typical collection procedure according to an embodiment of the present invention.

With reference first to FIG. 13, once a collection procedure 70 is initiated on the collection device 24 by the processor 102 using the protocol script 401 in step 402, such as in any of the above manners discussed previously above in earlier sections, after meeting entry criterion 226 (if provided in the collection procedure 70), a data event instance, e.g., an event 237, occurs according to the schedule of events 222 in step 404. For the event 237, in this example, the processor 102 prompts via a request 240 for the patient 12 to take a reading around a lunch event as mandated by the collection procedure 70. For example, the prompting of the request 240 may be an alarm provided by the processor 102 via indicator 148 that goes off, whereby the patient 12 is asked also on the display 108 by the processor 102 to take a reading. In one embodiment, the snooze feature as well as the skip reading feature are provided by the software 34, where the patient 12 can use the user interface 146 to enable a delay or to skip the data collection. For example, selecting the delay feature as discussed previously above in earlier sections can cause the processor 102 to prompt the patient 12 again for the event 237 a predefine amount of time after enabling the delay to the data collection. For example, such a feature could be used in case the patient 12 cannot take the reading at the time of the prompting in one embodiment, e.g., at the beginning of the window of time in which to provide the measurement/reading. Likewise, the skip feature would be selected if the patient believes he/she cannot perform the measurement/reading within the window of time. An example of a window of time or a specific time-window around an event is shown by FIG. 10B ("allowable window").

The processor 102 according to the protocol script 401 then uses adherence criterion 224 in step 406 to determine whether the data collection for the event 237 was successful by meeting the conditions of the adherence criterion 224 in one embodiment. For example, a successful data collection will occur if the patient 12 successfully collects the data within the specified time-window. In another embodiment, the same processing may be applied to one or more sampling group 262. Successfully collected data for such events in the schedule of events 222 and/or sampling grouping 262 is then contextualized by processor 102 according to the protocol script 401 in step 410, for example, by associating in the data file 145 with the collected data, e.g., data 256, the current time e.g., the date-time stamp 169 (FIG. 4), the event 239 and/or request 240, and available contextual information 156, e.g., about the patient's therapy as well as the unique identifier 167, if needed, as discussed also previously above in earlier sections.

If, in the above example, the patient 12 fails to collect data within the specified time-window, then in step 412 the processor 102 according to the protocol script 401 scans the contextualized data resident on the collection device 24 to determine if a similar data-point is available that meets the requirements of the missed data-point. This data-point will be selected by the processor 102 according to the protocol script 401 in step 414 only if it fulfils all requirements of the data-point intended to be collected.

As an example, if the collection procedure 70 requires a paired measurement, i.e., pre- and post-meal measurements, then it is important for both of these measurements to be made around the same event. In this case, substitution of any one value from a prior value is not permissible; should such occur, an exception is marked for the event under consideration. In this scenario, the pertinent element in the data-structure is incomplete at that location wherein the processor 102 in step 416 will declare an exception, such as providing a <null> value to the unique identifier 167 in the specific data record 152 for the event 237 which caused the exception. Should no such constraint exist, then a data-point from the data resident on the collection device 24 can be selected by the processor 102 in step 414 and added to the contextualize collected data in step 410. This substitute data-point will have the same contextual information, event context, and collected within a specified time-window of the original collection period if such is a requirement. In step 418, according to the protocol script 401, the processor 102 will check to see data collection is completed for all of the events 237 in the schedule of events 222 of the collection procedure. The processor 102 also checks whether exit criterion 228 is met, if such is provided by the collection procedure 70. If not, then the processor 102 proceeds with the next event in the schedule of events 222 by returning to step 404 wherein the data collection then proceeds for the remainder of the collection procedure 70 in a similar fashion. It is to be appreciated that frequent messages as part of the guidance 230 of the collection procedure 70 can be displayed by the processor 102 to the patient 12 on the display 108 to guide the patient throughout the entire data collection. It is to be appreciated that as part of the protocol script that whenever any specified exit criteria is met, the processor 102 can end the collection procedure 70 in one embodiment or present as an option on the display 108 for the patient to select ending the procedure 70 in another embodiment. Once the data collection is completed in step 418, the protocol script 401 then hands over control of the processor 102 to the parse script 403 in step 420.

With reference to FIG. 14, which highlights the role played by the parse script 403, when control is passed upon completion of the collection procedure 70, the parse script 403 checks the contextualized data 170 in the data file 145 for incompleteness. To accomplish this, the processor 102 reads the contextualized data 170 from memory 110 in step 422 and looks for any exceptions (e.g., <null> value for any unique identifier 167) provided in the data file 145 as an exception check in step 424 according to the parse script 403. When possible, the processor 102 tries to address any these exceptions using data available on the collection device 24 should it be possible in step 426. As an example, applicable data either may be available from non-collection procedure 70 events or from data collected as part of another collection procedure 70. If the exception cannot be addressed from existing data, then in step 428 the collection procedure 70 is marked incomplete. At this point the completion flag 257 for the collection procedure 70 is set as incomplete (e.g., not set, <null>, a pre-define value, etc.). Otherwise, if there are no exceptions and/or all exceptions have been addressed in step 426, then the processor 102 sets the completion flag 257 as completed and then can display the result of the collection procedure 70 in step 430. The processor 102 in accordance with the parse script 403 then collects all of the data associated with the collection procedure 70 (i.e., data file 145) and hands control over to the analysis script 405 in step 432.

In step 434, the analysis script will cause the processor 102 to perform all the necessary analysis, such as analysis 258 (FIG. 6B) that is detailed in the collection procedures 70, on the data collected in step 432, if the completion flag 257 is marked complete in the data file 145. In one embodiment, simple analysis routines calculations can be performed on the collection device 24, whereas more complex collection procedures 70, the analysis can be done on a computer, such as computer 18 or 25.

When a collection device 24 containing one or more collection procedures 70 is connected to a device reader 22, such as the Smart-Pix device, that is connected to computer 18 or the clinician computer 25, the software 34 cause the associate processor to display automatically a list of the completed collection procedures 70 and their associated data files 145.

In one embodiment, the software 34 can interact with the device reader 22, such as provided as a SmartPix device, for visualization of results, or with any other device including computer 18, 25, etc., that can display the results of the analysis of the data from the collection procedure 70. At this point, if on the clinician computer 25, the clinician 14 can decide to view the results of completed and analyzed collection procedures 70 or carry out analysis of completed collection procedures 70. The clinician 14 can also review any collection procedure 70 that did not complete and try to evaluate the exceptions that exist in the collection procedure 70. This interaction gives the clinician 14 an opportunity to give the patient feedback on his data and/or evaluate reasons for the failure to complete existing collection procedure(s) 70.

Use Case Example

Figure 15:
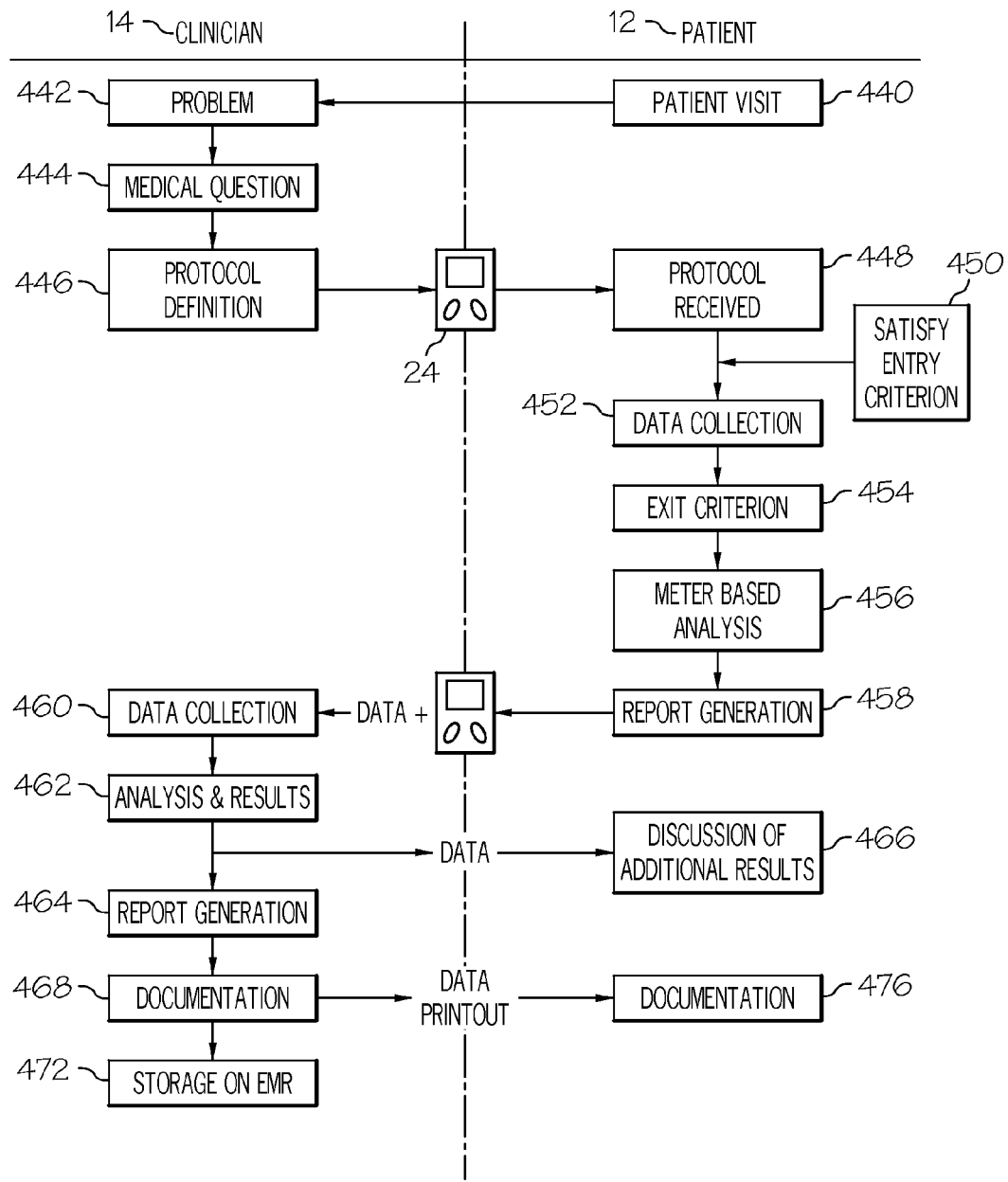
FIG. 15 shows a method of providing diabetes diagnostics and therapy support according to a use case embodiment of the present invention.

Referring to FIG. 15, a use case example is provided which highlights a sequence of actions carried out by the clinician 14 as well as the patient 12. This sequence encompasses an overview of the clinician 14-patient 12 interaction from the formulation of the medical question to the completion of the collection procedure 70. The dash-dot line indicates the boundary between the clinician 14 and patient 12 domains and it is the boundary across which information exchange takes place. The discussion on the completed collection procedure 70 also serves to encourage the patient and provides the clinician 14 with an opportunity to provide feedback on patient performance and progress.

In step 440, patient visits the clinician 14 and in step 442, the clinician identifies a problem, which results in the selection of medical use case (medical question) in step 444. After selecting the medical question, such as on computer 25, the clinician uses the computer to select and define/customize the structured collection procedure 70 in step 446 using method 200 and/or 300 (FIGS. 5A and 7A). After prescribing the structured collection procedure 70, the computer 25 provides the structured collection procedure 70 to the collection device 24, which is received in step 448. The patient 12 starts the data collection according to the structured collection procedure 70 using the collection device 24 after satisfying the entry criterion 226 provided in the procedure 70 in step 450. During the data collection in step 452, events 237 are automatically scheduled by the collection device 24 in accordance with the scheduled of events 222 contained in the structured collection procedure 70. Adherence criterion 224 is applied to at least to all biomarker measurements, which are evaluated and recorded for meeting the adherence criterion automatically by the collection device 24. In step 454, the structured collection procedure 70 is completed once the exit criterion 228 is met. Next in step 456, any available collection device based analysis 258 may be performed by the patient 12 if desire. Next in step 458, a report may also be generated, such as the data report mentioned in step 434 (FIG. 14). In step 460, the data (e.g., the complete data file 145) either from the collection device 24 or from the patient computer 18 is preferably sent to the clinician computer 25. The collected data is received in step 460, is then analyzed in step 462. Next, in step 464 a report can be generated, which may be used to facilitated a discussion of any additional result in step 466 with the patient 12. Next, documentation is printed in step 468, which can be given to the patient 12 in step 470 as well as recorded (stored) in an electronic medical record of the patient 12 in step 472.

Generation, Modification, and Transfer of Collection Procedures

Embodiments of the present invention also enable the generation, modification, and transfer of collection procedures 70 to and from a structured testing enabled device, such as collection device 24. As the collection procedures 70 stem from and aim to address specific medical use cases or questions, the transfer of the resultant information e.g., data file 145, from one device to another is carried out in a secure manner. Additionally, a method whereby all of the collection procedure related information (e.g., data file 145) for a patient or a group of patients can be managed in a secure and efficient manner.

It is to be appreciated that the discussion provided hereafter includes aspects related to the interaction between the clinician 14 and the patient 12 as discussed previously above concerning FIG. 15. In particular, the disclosure hereafter provides details regarding the infrastructure required to manage the generation, transfer, and analysis of the collection procedures 70. Reference hereafter is also made to the system 41 of FIG. 2, as aspects pertaining to the transfer of devices and information (data, reports, etc.) to and from the devices 18, 25 and 52 are provided.

In one illustrated embodiment, the system 41 can comprise server 52 being a web-server that serves as a repository of a plurality of collection procedures 70a, 70b, 70c, 70d, as software 34 that resides on the clinician computer 25, and the collection device 24, such as provided as a blood glucose meter. Henceforth these components are referred to as the "server", "software", and the "meter" respectively. Additionally, the computer 25 where the software 34 resides is termed as the "client".

In one embodiment, the server 52 can serve as a central repository for a number of collection procedures 70a, 70b, 70c, and 70d that address specific medical questions. Accordingly, one or more collection procedures 70 can be downloaded from the server 52 to the clinician computer 25. In such an embodiment, all communications between the server 52 and the client computer 25 is done in a secure and web-based format. Additionally, in another embodiment, there is no full two-way data transfer between the computer 25 and the server 52 such that patient data can never be transferred to the server 52. Furthermore, in other embodiment, a request for a collection procedure from the server 52 can be made only with a valid identifier. Such an embodiment ensures that only authorized clients are allowed to access the server 52 to download the requested collection procedure(s) 70.

In one embodiment, each collection procedure 70 downloaded from the server 52 can be used only once (e.g., if the completed flag or state is set, the procedure 70 cannot be run again until reauthorized by the clinician 14). Each successive download of the collection procedure 70 requires access from an authorized client user with a valid ID 71 (FIG. 2). The server 52 also provides the client computer 25 with updates thereby ensuring that the software is the most recent version. There also exist restrictions on the communication from the client computer 25 to the server 52. The server 52 can only access information related to the installed version of the software 34. It is not possible for the server 52 to access any data resident in the client database e.g., memory 78. Additionally, the data on the client computer 25 is access controlled so that it cannot be used and accessed without the necessary permissions.

The software 34 residing on the client computer 25 serves as the interface between the server 52 and the collection device 24. The software 34 at the front end includes a user-friendly interface that provides the clinician 14 with ready information pertaining to the overall practice. This information may include details about all assigned patients, details about the patients the clinician 14 is scheduled to see on a given day, as well as the details about patients that need extra attention. The software 34 also interfaces with a database that includes relevant patient data that is arranged by an individual patient ID, such as used by and provided in the healthcare record system 27. The software interface also allows the clinician 14 to access the patient 12 details using the patient identifier. In this manner the software 34 provides the clinician 14 with information about the collection procedure(s) 70 that the patient 12 has already completed (i.e., those with a completed set for the completion flag 257), the associated results, and also the collection procedure(s) 70 that the patient 12 is currently performing. All of the data residing on the client computer 25 is secure and access-controlled. The server 52 has no means to access the data. The clinician 14 can access data from all patients in the practice. In addition, an individual patient 12 can access his data, such as from a server of the clinicians, using his patient identifier in a secure web-based format. This data is downloaded to the database on computer 25 from the collection device 24 and associated to the patient 12 using the patient identifier.

At the time of data download from the collection device 24, the software 34 also performs an analysis on the data to ensure that the integrity of the data is maintained and no corruption in the data has taken place at the time of transfer. The client computer 25 with the help of the software 34 can also send emails to the individual patients and these emails can contain information about an upcoming appointment, reminders on what the patient is supposed to do after an appointment and reports that are results of a completed collection procedure 70. When the clinician 14 downloads a collection procedure 70 from the server 52 for a particular patient, the collection procedure 70 is associated with the patient identifier. In this way, it is possible to account for what collection procedures 70 are currently underway for his patients.

A downloaded collection procedure 70 can also be modified by the clinician 14 using the software 34 to tailor the collection procedure 70 to individual patient needs as previously discussed above in earlier sections (FIG. 7B). At the time of modification of the collection procedure 70, the clinician 14 also has the option to alter the analysis that will be carried out on the modified collection procedure 70. Additionally, even for standard collection procedures 70 that have not been modified, the clinician 14 has the option to add additional options for analysis.

Furthermore, the clinician 14 can decide and set guidelines as to when the procedure 70 must terminate. For example, the clinician 14, can decide and set how many adherence violations are allowed, i.e., how many measurements the patient can miss, such as via using the options parameter 232 in the collection procedure 70.

In one embodiment, once a collection procedure 70 is introduced into the collection device 24 by the clinician 14 (details discussed in the next section), the collection procedure 70 cannot be altered by the patient 12. Additionally, the collection procedure 70 is associated with both the clinician 14 (the prescriber) and the patient identifiers to ensure accounting of the collection procedure 70 and associated data (e.g., data file 145).

The software 34 also allows the clinician 14 to select the type of report that will be generated once the completed collection procedure 70 has been analyzed. This report is tailored for the device on which it will be viewed. The report could be for a mobile device such as a telephone, a palm device or a meter, or a computer, or a printed format. The software 34 also has the ability to connect with an electronic medical records system to add patient data and results of analysis performed on the data from a collection procedure 70 to the medical records.

The collection device 24 serves as the mechanism by which prospective and contextualized data is collected by the patient 12 as recommended by the collection procedure 70. The collection device 24 can be owned by the patient or it can be owned by the clinician 14 and loaned to the patient 12 for the duration of the data collection associated with the collection procedure 70. The clinician 14 can introduce the collection procedure 70 into the collection device 24 by a number of mechanisms. For example, the collection procedure 70 can be downloaded from the server 52 and added to the collection device 24 via a connecting cable that links the client computer 25 to the collection device 24 in one embodiment. The collection procedure 70 can also be obtained in another embodiment on a chip (e.g., computer readable medium 40) that can be inserted into the collection device 24. This collection procedure 70 is then loaded into firmware of the collection device 24 where it can be initiated by the patient 12. The collection procedure 70 can also be introduced using an RFID tagged chip (e.g., computer readable medium) in still another embodiment.

Along with the downloaded collection procedure 70, the collection device 24 also has the ability to display instructions to the patient 12 that guide the patient at the time of data collection. Additionally, as discussed above, the collection procedure 70 can introduce into the collection device 24 both the patient identifiers as well as the clinician identifier. Similarly, the data collected from the collection device 24 can be associated with the patient identifier and clinician identifier, such as part of setup data 163 (FIG. 4) in the data file 145. Additionally, the setup data 163 in the data file 145 can include information about the collection device 24 (i.e., measurement noise, calibration data), as well as strip lot numbers and other information about the strips used for any data collection event 237. Such information may be helpful at the time of data analysis.

Figure 16:
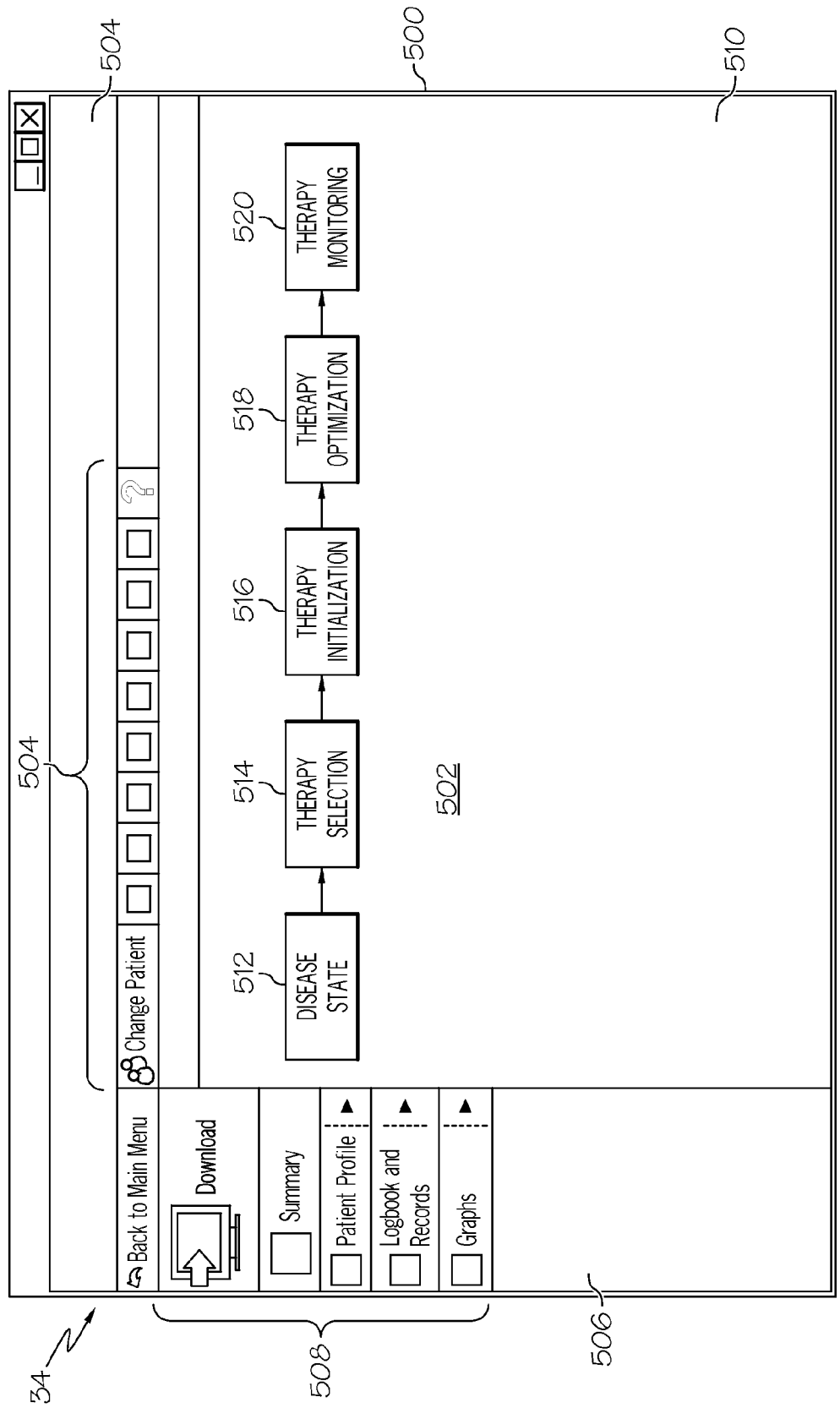
FIGS. 16, 17, and 18 depict different screen shots of a graphical user interface according to an embodiment of the present invention.
Figure 17:
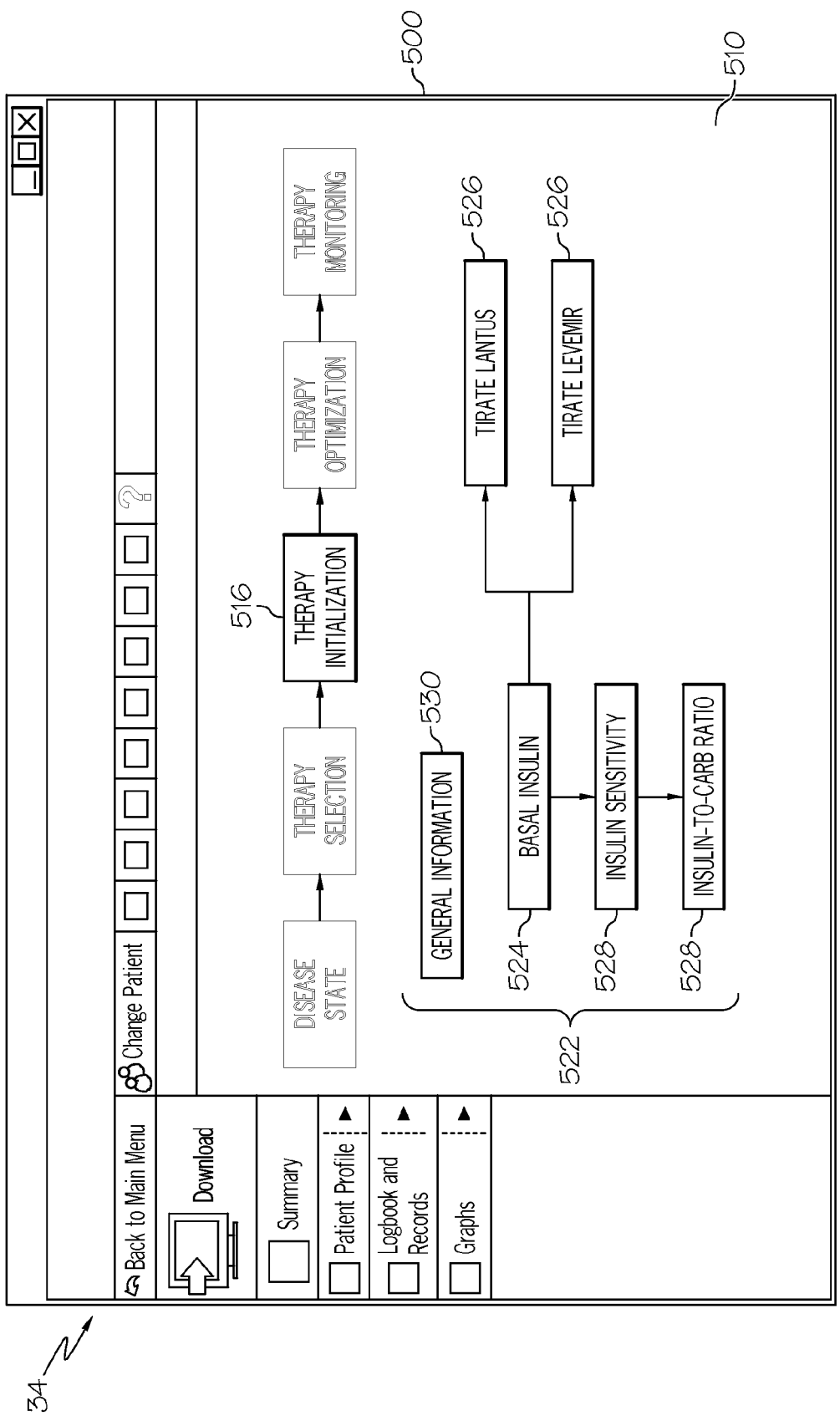
Figure 18:
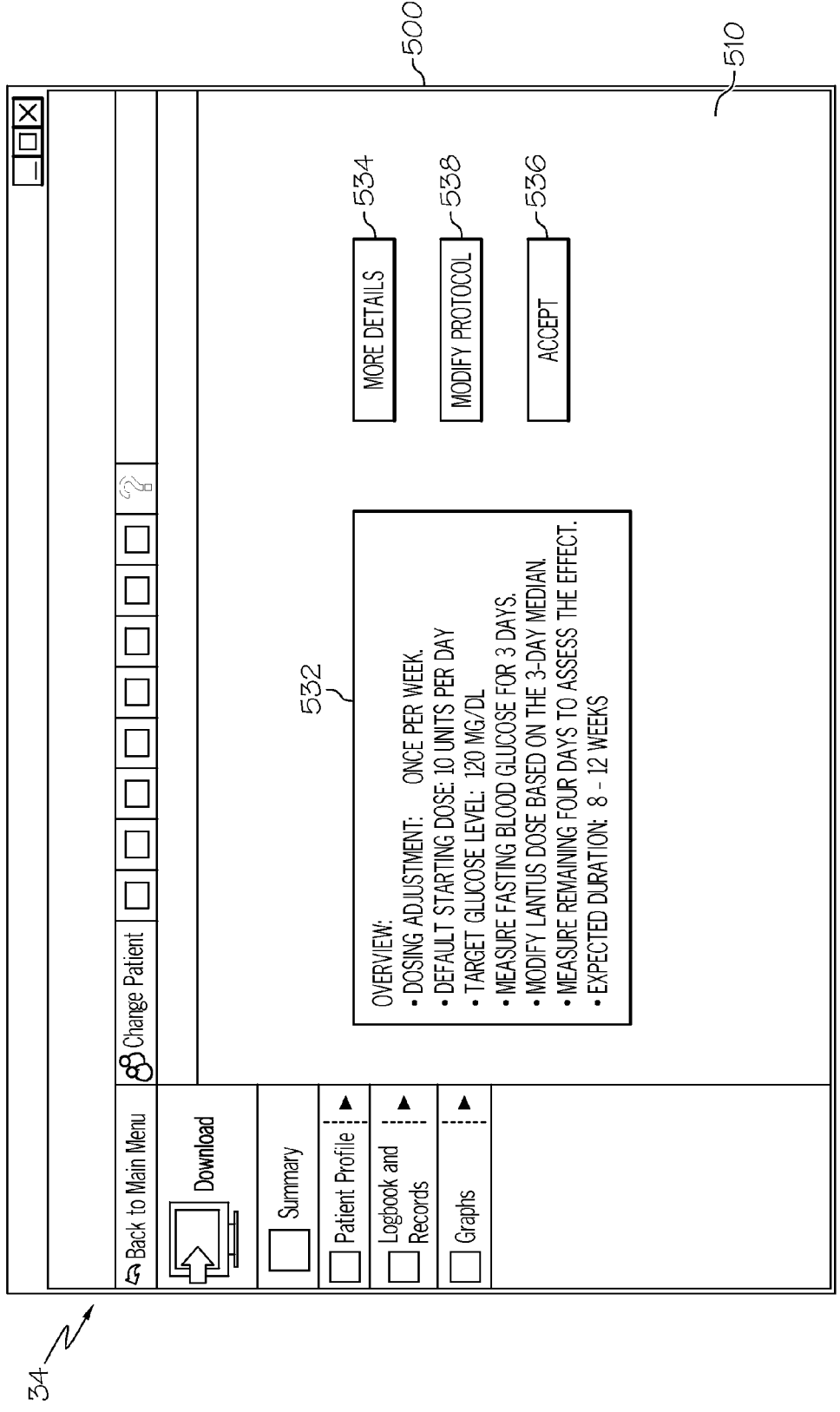

At the completion of the collection procedure 70 the collection device 24 can be connected to the software 34. At that time data, such as data file 145, is transferred securely and stored by the processor 76 of the client computer 25 according to the software 34 running thereon. Once the analysis performed on the data from the collection procedure is completed by the software 34 on the client computer 25, the computer 25 also has the ability to store results of the analysis for patient reference. Reference is now made to FIGS. 16-18 hereafter.

Software GUI

In one embodiment, a typical workflow highlighting further features of the software 34 useable through a graphical user interface (GUI 500) provided thereby on a computer, such as computer 25 and/or server 52, are presented. In this example, the typical scenario is when the clinician 14 opens the case file for a particular patient is considered. As shown in FIG. 16, the clinician 14 can readily visualize important details about a displayed patient file 502 using the GUI 500 of the software 34 running on the client computer 25. On a top pane 502 of the GUI 500, the clinician 14 can see and use various administrative tasks 504, such as changing the displayed patient file, create an email containing information form the patient file, create a fax containing information from the patient file, save the patient file, bookmarking data in the patient file, select existing bookmarks, print information/graphs from the patient file, etc.

On a left pane 506 of the GUI 500, the clinician 14 has additional options 508 such as the option to download patient data, such as data file 145, when a collection device 24 is connected to the computer 25 or 18 (wired or wirelessly). The other options 508 also can also include viewing details regarding a patient profile, logbook, and additional records, and graphs based on calculated data, etc. As indicated by FIG. 16, the summary option is selected, which shows its content in a main pane 510.

The main pane 510 indicates all of the typical steps in a workflow for therapy administration for the patient 12. These steps can include the following: Disease State 512, Therapy Selection 514, Therapy Initialization 516, Therapy Optimization 518, and Therapy Monitoring 520. Each step provided as an icon on the GUI 500 is discussed hereafter.

Disease State 512 is a determination of the disease state, e.g., the patient is a Type 1 or a Type 2 diabetic. Typically, the disease state determination is carried out when the patient 12 first visits the clinician 14 or when the clinician 14 suspects that a particular patient might be at risk. Therapy Selection 514 follows thereafter once the disease state is determined, and the clinician 14 needs to select an appropriate therapy that takes into account the patient's disease state. As Therapy selection 514 can include the processes of methods 200 and 300 shown by FIGS. 5A and 7A, respectively, no further discussion is provided. Therapy Initialization 516 is the process of therapy initialization involves establishing the initial details by means of which therapy is administered to the patient 12. This may include details about the starting dose of the therapy, time when the therapeutic is taken, and the likes. Further details about Therapy Initialization 516 are provided hereafter in reference to FIG. 17. Therapy Optimization 518 involves the determination of the best effective dose for the patient such that it will not cause side effects. Finally, Therapy Monitoring 520 involves routinely monitoring the patient 12 to detect therapy obsolescence after the selected therapy has been optimized. Thus, the GUI 500 provides the clinician 14 with all of the useful information in a user-friendly format.

FIG. 17 represents the scenario when the clinician 14 has already determined the disease state and selected a therapy, via Disease State 512 and Therapy Selection 514, and is at the step for Therapy Initialization 516. As shown, the software 34 shades in the GUI 500 the steps already completed wherein only the step currently underway, e.g., Therapy Initialization 516, is highlighted. In addition, in one embodiment, the software 34 does not permit the clinician 14 to progress to the next step without accomplishing all the required actions in the current step (in other words, all previous steps have been accomplished). However, the software 34 provides the clinician 14 with the option to go back and modify prior steps via selecting the particular icon for the step in the GUI 500.

In this example, the patient 12 is diabetic, and currently for Therapy Initialization 516 the clinician 14 needs to initialize a long acting insulin therapy for a Type 1 diabetic patient. As shown, the clinician 14 is presented on the GUI 500 for this step with all available initializing options 522 for initializing the therapy. For example and as shown, the clinician 14 can select a type of drug 524, such as show as a long acting basal insulin, and select procedure selection icons 526 associated with the drug 524 and each associated with a collection procedure 70 that is available for addressing a therapy question (s) regarding a particular drug (e.g., Lantus, Levemir) listed associated (and available) with the type of drug 524. The software 34 through the GUI 500 also permits the clinician 14 to decide if additional therapy related parameters 528, such as insulin sensitivity, insulin to carbohydrate ratio, and the like, should be undertaken if such is needed. Additionally, further details for the therapy initialization can be viewed via selecting an icon for general information 530.

When the clinician selects one of the procedure selection icons 526, the software 34 provides a snapshot 532 of the conditions set in the associated collection procedure 70, such as illustrated by FIG. 18. Typical initial conditions provided in the snapshot 532 can include: frequency of dosage (dosing adjustment), (default) starting dose, target levels, schedule of events (e.g., Measure fasting blood glucose for 3 days), recommendations for computation (e.g., modify drug dose base on the 3-day median, measure remaining for days to assess the effect), and the like. If more details regarding the selected collection procedure 70 are desired, such as related medical literature, case studies that may have formed the basis for the structured testing procedure, and the like, can be viewed via More Detail icon 534. The clinician 14 has also the choice to either accept the collection procedure 70 as provided, via the Accept icon 536 or suggest modifications to the collection procedure 70 via the Modify protocol 538. As selecting the Modify protocol 538 can open on the GUI 500, for example, a screen representation of all the parameters in the procedure 70 for modification, such as depicted by FIG. 7B, and as such was previously discussed above in earlier sections no further discussion is provided. Once modifications are made to the collection procedure 70, the clinician 14 can review and accept the changes. Upon accepting the collection procedure 70, via selecting the Accept icon 536 on the GUI 500, the software 34 cause the processor e.g., processor 76, to send the completed collection procedure 70 to the collection device 24 as discussed previously above in earlier sections. Certain advantages of the above mentioned embodiments of the present invention are noted hereafter.

Although not limited thereto, the embodiments of the present method offer the following noted advantages. Certain embodiments enable contextualization of collected data by taking into account factors such as meals and existing medications. All of the data analysis can be carried out on prospective data, i.e., contextualized data collection is carried out keeping in mind the medical question that needs to be addressed. The collection procedures 70 are each geared towards collecting bG data to address a specific medical issue, e.g., control of postprandial glycemic excursions, regulating the fasting blood glucose value, characterizing the patient insulin sensitivity, monitoring the patient's therapeutic response, and the like. Using such collection procedures, makes the task of collecting BG values goal oriented as the patient knows the reason why he or she is carrying out such tests. It is believed that awareness of the reason for conducting tests would lead to an increase in adherence.

Also, certain embodiments provides the infrastructure necessary to manage multiple simultaneously running collection procedures 70 on different collection device 24 by different patients 12, while ensuring secure web-based communication for receiving and transmitting the collection procedures 70 and the results obtained from the analysis of these collection procedures 70. For example, certain embodiments help the clinician 14 by: making it easier for the clinician 14 to impact all of the stages of a patient's therapy ranging from disease state determination to regular monitoring under a working regular therapy; making it possible for the clinician 14 to manage the various stages of collection procedure 70 execution for a group of patients in a secure, and web-based format; offering the clinician 14 flexibility by providing the option to select collection procedures 70 from a pre-determined list or modify a collection procedure 70 based on patient needs; making the interaction between the clinician 14 and the patient 12 more effective as the communication is entirely data-centric and guided by, for example, a medical question at hand.

Specific examples of therapy optimization are described below, specifically in the context of insulin titration.

Structured Collection Embodiments for Optimizing the Titration of Insulin

Figure 19A:
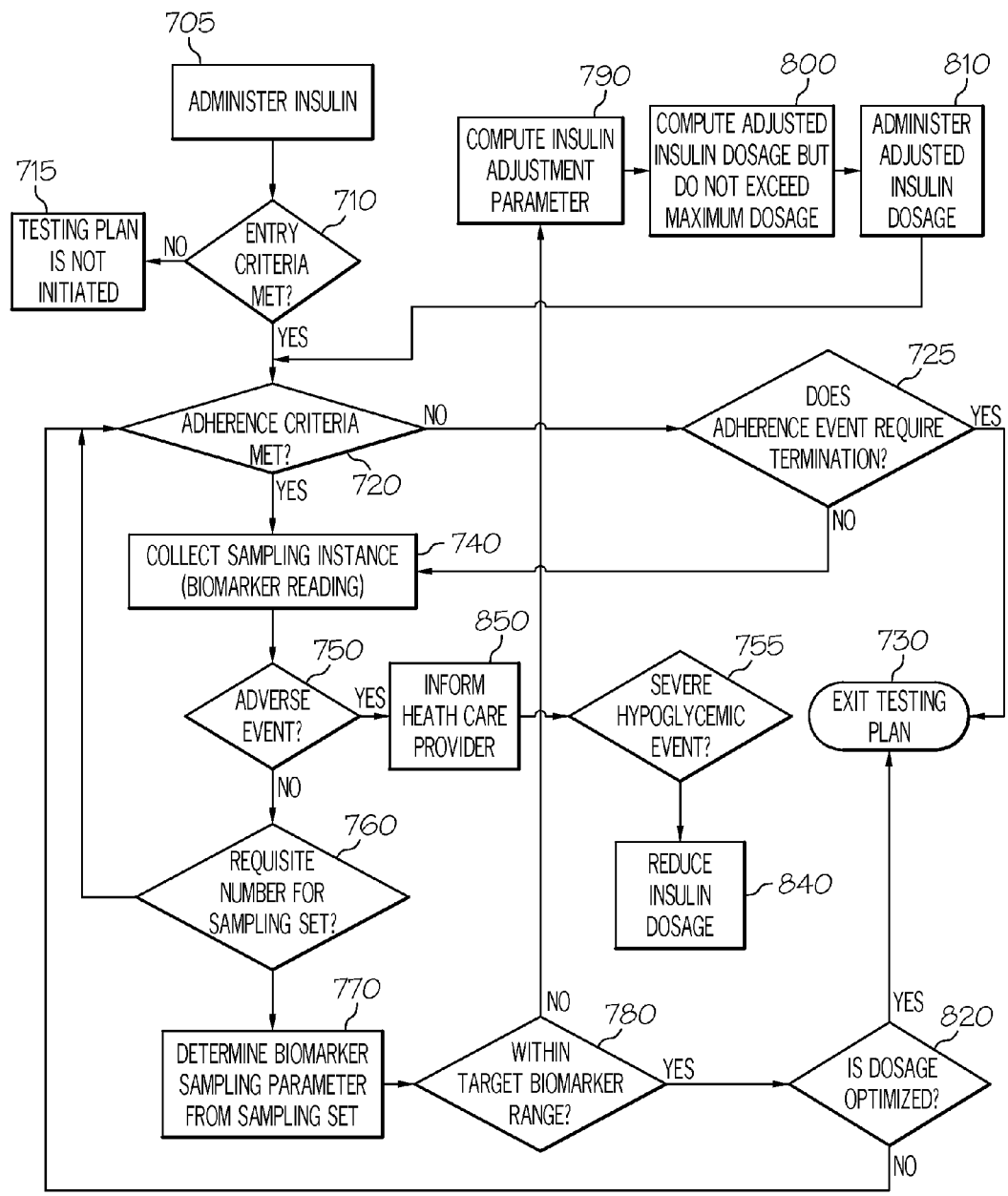
FIGS. 19A-19D shows flow charts depicting structure collection protocols for optimizing the titration of insulin according to embodiments of the present invention.

FIG. 19A provides an exemplary embodiment of structured collection protocols for optimizing the titration of insulin dosage, which thereby yield dosages of insulin which maintain biomarker levels within a desired range. In one embodiment, the titrated insulin may be basal insulin. Upon starting the structured collection, the dosage of insulin is typically the initial prescribed dosage, for example, the initial prescribed dosage listed on the package. However, other dosages are contemplated depending on what stage of the structured collection protocol, as the entry criteria may be considered before every biomarker reading. Consequently, the initial dosage may be an adjusted dosage above the initial prescribed dosage, the maximum allowable dosage, or even the optimized dosage. It is contemplated that the structured collection may be used to obtain the optimized insulin value, or may be used post-optimization to verify that the insulin dosage is still optimal.

Figure 19B:
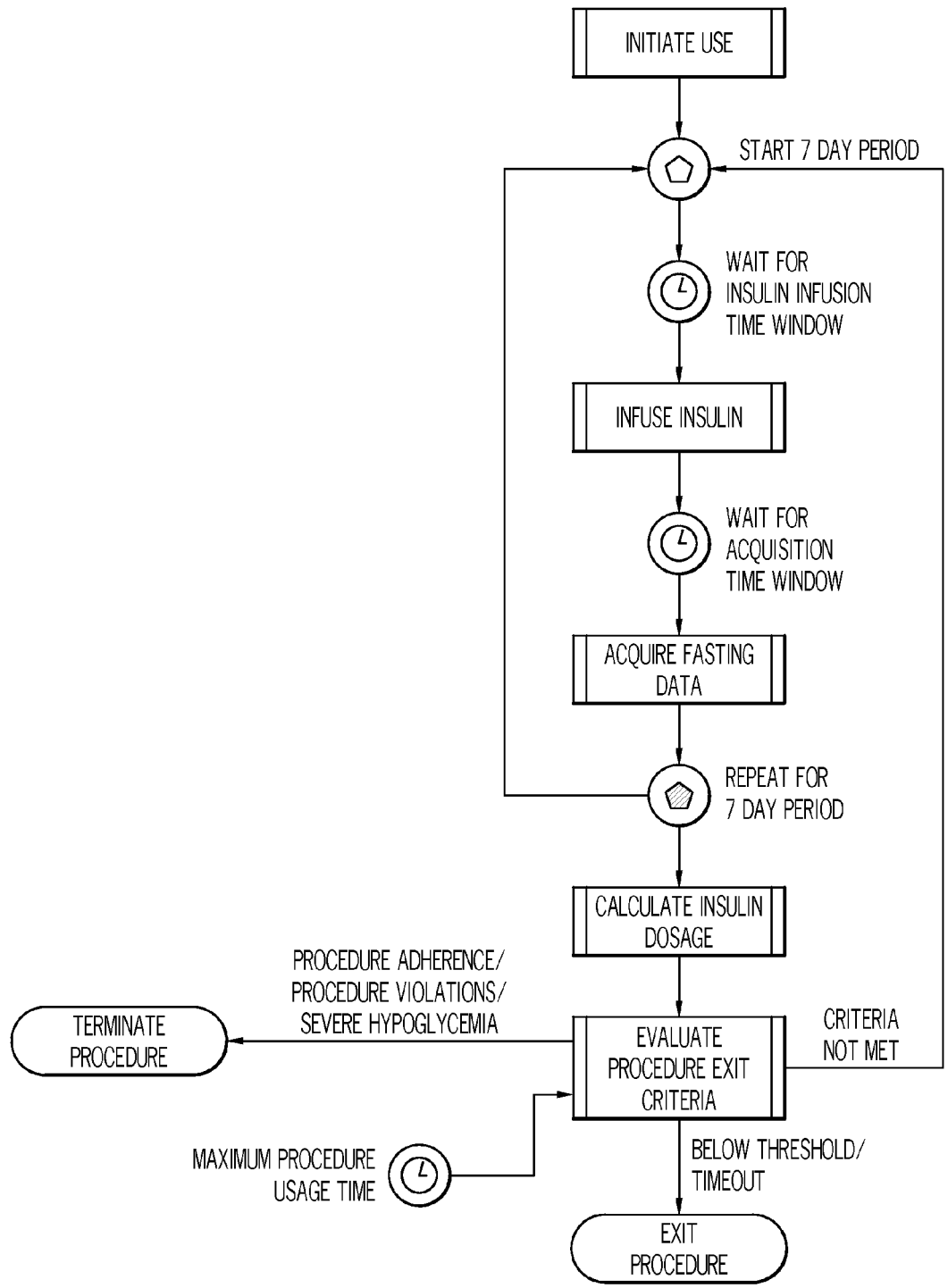
Figure 19C:
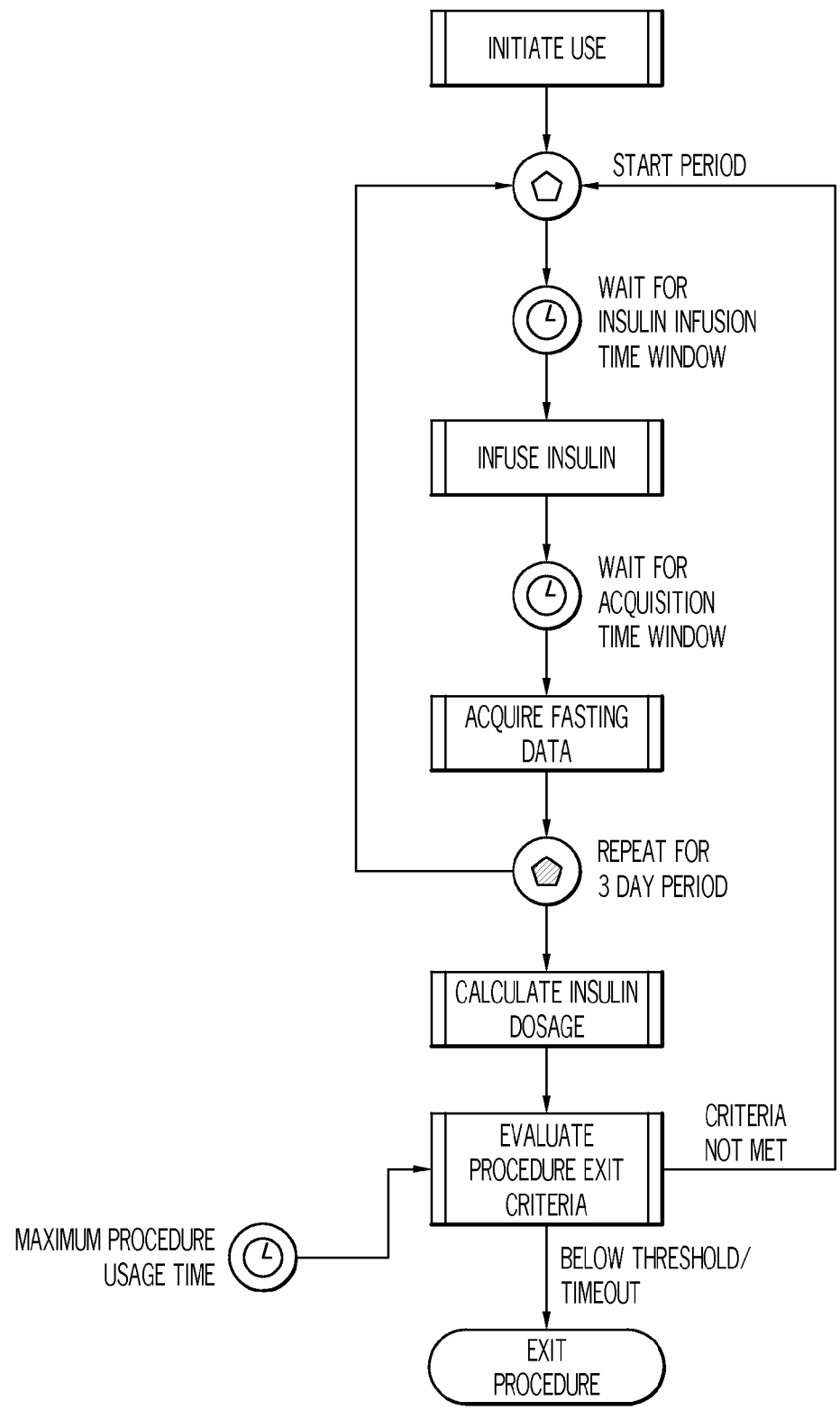
Figure 19D:
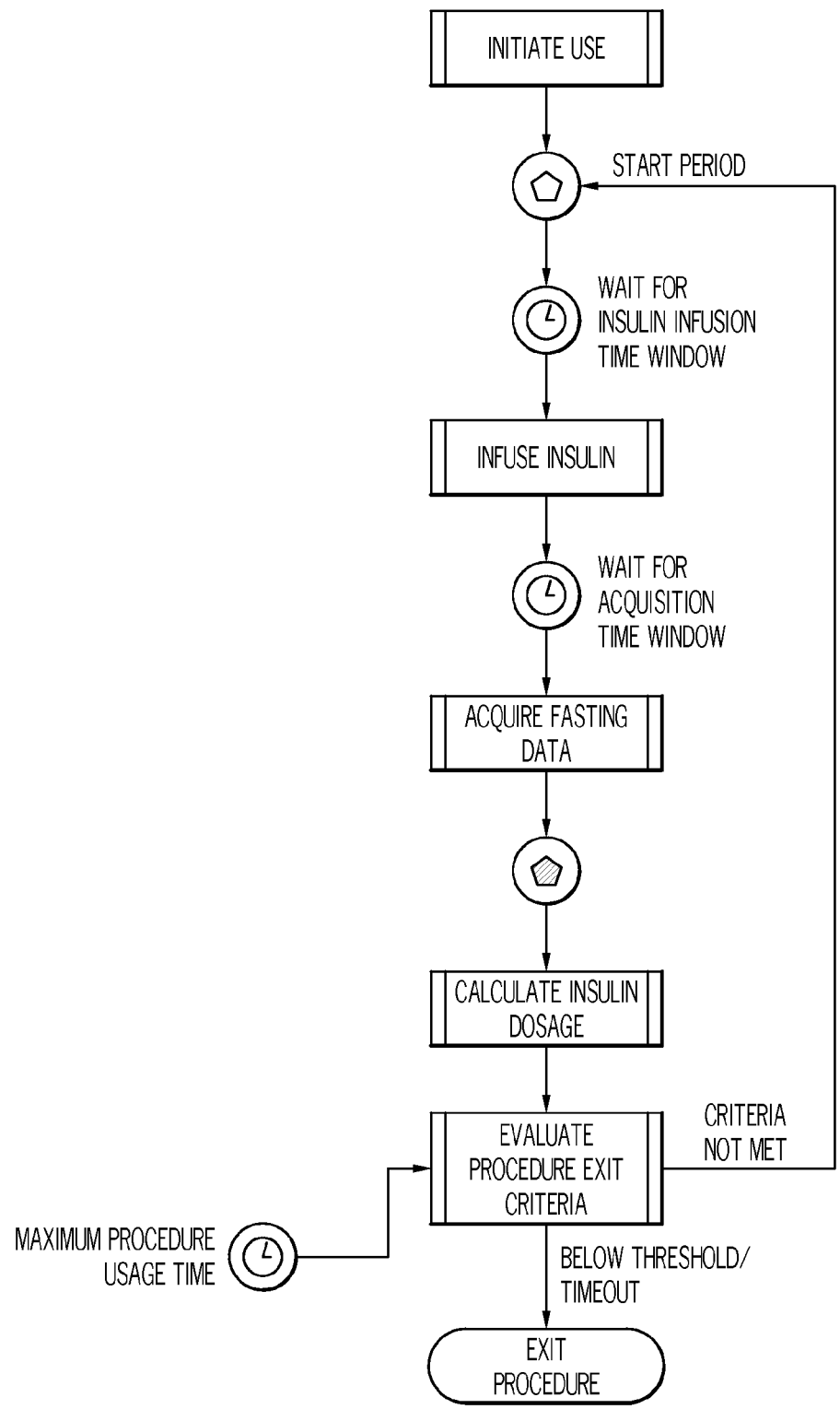

In the embodiments of FIG. 19A, the structured collection protocols may optionally require the consideration of entry criteria 710 before beginning collection of the biomarker data. It is contemplated that the diabetic person, the healthcare provider, or both may determine whether the entry criteria are met. The entry criteria, which in some embodiments may be established by the healthcare provider, may relate to the age, weight, and medical history of the diabetic person. Consequently, the structured collection protocol may require a diabetic person to receive a check-up or physical to ensure the diabetic person satisfies the entry criteria. For instance, the entry criteria may specify the fasting plasma glucose (FPG) level or glycolated hemoglobin level as determined by the HbA1c test. The normal range for the HbA1c test is between 4-6% for people without diabetes, so the entry criteria may require values above about 6%, or in exemplary embodiment, between about 7.5% to about 10%. As an additional example of entry criteria, a fasting plasma glucose level of at least about 140 mg/dl is required. The entry criteria may also set requirements on weight or Body Mass Index (BMI). For example, the required BMI may be greater than about 25 kg/m2, or between about 26 kg/m2 to about 40 kg/m2. Additionally, the entry criteria may specify a desired age range (e.g., 30-70) or the number of years afflicted with diabetes (e.g., at least 2 years). Moreover, while it is contemplated that the structured collection protocol is applicable to persons afflicted all types of diabetes, the entry criteria may limit the structured collection protocol to type 2 diabetics. Furthermore, the entry criteria may center on the current diabetes treatment regimen of the diabetic person. For example, the entry criteria may require that the treatment regimen for the diabetic person be limited to oral anti-diabetes medication i.e., no injected insulin. Additionally, the entry criteria may require that the diabetic person not be ill or under stress. As stated above, while the embodiments of FIG. 19A are directed to the consideration of entry criteria, the present structured collection protocols do not require the consideration of entry criteria before collection of biomarker data. For example, referring to the additional embodiments of FIGS. 19B-D, the embodiment of FIG. 19B requires the consideration of entry criteria; however, the embodiments of FIGS. 19C and 19D do not include such constraints.

Referring again to FIG. 19A, if the entry criteria are not met, the structured collection protocol will not be initiated 715. The diabetic person or healthcare provider may determine whether the entry criteria have been met, or the data processor may determine whether criteria have been met. If the entry criteria are met 710, then the diabetic person may commence with the structured collection protocol. However, in some embodiments, it may be required for the diabetic person satisfy adherence criteria before the collection of biomarkers or the administration of insulin.

The adherence criteria are the procedural requirements that the diabetic person must follow when conducting the structured collection protocol. To get a proper baseline for the biomarker readings, it may be beneficial to ensure all readings are taken uniformly, i.e., at approximately the same time of day for each sampling instance. Consequently, the adherence criteria may specify that biomarker collection or insulin administration be conducted at the same time each day. To aid the diabetic person in satisfying the adherence criteria, the data processor display prompt the diabetic patient with audio and/or visual reminders to collect their biomarker sample, and enable the diabetic patient to set future reminders. In specific embodiments, the adherence criteria may also require that the diabetic person fast for a set period of time prior to collecting the biomarker reading. The adherence criteria may also be directed to determining whether the diabetic person is taking the correct dosage of insulin. In additional embodiments, the adherence criteria may also require no recent hypoglycemic events or severe hypoglycemic events (low blood glucose events) a set period (e.g. one week) before the collection of biomarker data. Furthermore, the adherence criteria may specify an exercise regimen or eating regimen for the diabetic person. As used herein, "eating regimen" means the typical eating regimen of the diabetic person in terms of calories, carbohydrate intake and protein intake.

If the diabetic person fails to meet any or all of the adherence criteria, the diabetic person may be informed, for example, by the display of the blood glucose meter that they failed to meet the adherence criterion. If the diabetic person fails to meet the adherence criteria, the data processor device may tag the adherence event or the diabetic person may record the occurrence of the adherence event. After the adherence event is recorded, the structured collection protocol is typically continued. However, if too many adherence events are recorded (e.g., more than 4 within a sample period, more than 20 adherence events within the entirety of execution), then the structured collection protocol may be terminated. Furthermore, the structured collection protocol may also evaluate adherence events differently. For example, there may be a tiered adherence event assessment, wherein adherence events are weighted. In one or more embodiments, if the adherence event does not impact the biomarker data, then it is not weighted as heavily as an adherence event that affects the biomarker data. For example, when a diabetic person fasts the requisite time period before taking a fasting blood glucose reading, but fails to record that the reading is a fasting blood glucose reading, this would be categorized diabetic as a less significant and thereby lower weighted adherence event, because the recording error does not affect the fasting blood glucose reading. In contrast, fasting less than the requisite period will impact the fasting blood glucose reading, and thus constitutes a more significant and thereby higher weighted adherence event.

If there is a violation event (e.g., a missed insulin administration), the structured collection protocol is more likely to be terminated than for an adherence event (e.g., fasting less than the required fasting period), because a violation event impacts the structured collection protocol more significantly. Since the present structured collection protocol is directed to optimizing insulin administration, it stands to reason that missing an insulin dose would be a significant violation event.

Like other instructions provided to the diabetic person throughout the structured collection protocol, the entry criteria or the adherence criteria may be provided to the diabetic person via a paper instruction form, or a display unit on a data processing device or processor 102 as shown in FIG. 3. The data processing devices may be any electronic device described above. In one or more embodiments, the data processing device may be a computer or a blood glucose meter with a data processor and memory units therein. In addition to listing the entry criteria, adherence criteria, or both, the data processing device may prompt the diabetic person to answer medical questions, wherein the answers to the medical questions are used by the device to determine compliance with the entry criteria, or adherence criteria. The data processing device may inform the diabetic person of the failure to comply with the entry criteria or adherence criteria. For example, the data processing device may inform a diabetic person if subsequent sampling instances are not taken around the same time as the first sampling instance. The patient can record sampling instances or answer medical questions by entering the data event directly into a device or computer, wherein the processor 102 can store the information and provide additional analysis depending on the parameters of the structured collection protocol.

Referring again to FIG. 19A, the diabetic person may begin collection of one or more sampling sets of biomarker data. Each sampling set comprises a sufficient plurality of non-adverse sampling instances recorded over a collection period, which means at least two sampling instances which are not indicative of an adverse event e.g., a hypoglycemic or hyperglycemic event. Each sampling instance 740 comprises a biomarker reading at a single point in time. The collection period for the sampling set may be defined as multiple sampling instances within a day, multiple sampling instances within a week, multiple sampling instances within consecutive weeks, or multiple sampling instances on consecutive days within a week. The biomarker may relate to the levels of glucose, triglycerides, low density lipids, and high density lipids. In one exemplary embodiment, the biomarker reading is a blood glucose reading. In addition to the biomarker reading, each sampling instance may comprise the biomarker reading and other contextual data associated with the biomarker reading, wherein the contextual data is selected from the group consisting of the time of collection, the date of collection, the time when the last meal was consumed, affirmation that fasting has occurred for the requisite period, and combinations thereof. In the exemplary embodiment of FIG. 19B, the structured collection protocol occurs over a 7 day method which requires the diabetic patient to administer insulin in the evening followed by the collection of fasting blood glucose reading the following morning. In addition to the morning biomarker collection, the diabetic patient may also be instructed to take an additional biomarker reading when the diabetic person is encountering the symptoms of hypoglycemia.

Referring again to FIG. 19A, upon collecting the biomarker reading, there is a determination as to whether the biomarker reading indicates an adverse event 750. While the present discussion of adverse events centers on hypoglycemic events and severe hypoglycemic events, which may necessitate medical assistance, it is contemplated that the adverse events may refer to undesirable levels of other biomarkers or medical indicators, e.g., lipids levels, blood pressure levels, etc. In one embodiment, this determination of adverse events may be performed by comparing the biomarker reading to a low threshold, for example, the hypoglycemic event or severe hypoglycemic event thresholds shown in Table 1 below. If the biomarker reading is below one or both of these thresholds, then an adverse event may have occurred, and should be recorded as an adverse event, or specifically recorded as a hypoglycemic event or severe hypoglycemic event. As described above, this determination may be performed by a data processor unit, or may be entered manually by the diabetic person.

TABLE 1

| Blood Glucose Range (mg/dl) | Insulin Adjustment Parameter (units) |
|---|---|
| below 56 (severe hypoglycemic event) | −2 to −4 |
| 56-72 (hypoglycemic event) | 0 |
| 73 to 100 (target biomarker range) | 0 |
| 100-119 | +2 |

TABLE 1-continued

| Blood Glucose Range (mg/dl) | Insulin Adjustment Parameter (units) |
|---|---|
| 120-139 | +4 |
| 140-179 | +6 |
| 180 and above | +8 |

If there is an adverse event (e.g., a severe hypoglycemic event), in one embodiment, the instructions or data processing device may recommend that the diabetic person contacts their health care provider. In another embodiment, the system may automatically contact the health care provider (HCP). In addition, an adverse event may optionally lead to a dosage reduction. Referring to Table 1 above, if it is a hypoglycemic event (between 56-72 mg/dl), the HCP may be contacted 850, but the dosage is not adjusted (See FIG. 19A). However, if it is a severe hypoglycemic event (below 56 mg/dl), the dosage may be reduced by some amount (640), for example, 2 units, 4 units, or another amount as dictated by the low biomarker reading. In specific embodiments, if the recorded adverse event is a second measured severe hypoglycemic event within the same day, the dosage is not reduced. In further embodiments, a data processing device may utilize an algorithm to automatically reduce the insulin dosage and instruct the diabetic person of the reduced insulin dosage. Moreover, the data processing device which collects the biomarker reading may automatically notify a healthcare provider of the adverse event, for example, by an automated email or text message.

If the biomarker reading is not adverse, the next step depends on whether or not the sampling set 760 has a sufficient number of non-adverse sampling instances. If only one sampling instance is required for the sampling set, then the biomarker sampling parameter may be calculated at that point; however, as stated above, the sampling set typically requires a plurality or at least two sampling instances for each sampling set. In exemplary embodiments, two or more sampling instances taken on consecutive days are required for each sampling set. If multiple sampling instances are required, then the diabetic person must continue to collect sampling instances.

Once the requisite number of sampling instances for the sampling set is obtained, the biomarker sampling parameter may be obtained 770. The biomarker sampling parameter may be determined by various algorithms or methodologies. For example, it may be determined by averaging sampling instances, summing the sampling instances, performing a graphical analysis on the sampling instances, performing a mathematical algorithm on the sampling set, or combinations thereof. In an exemplary embodiment, sampling instances (i.e., biomarker readings) are collected on at least three consecutive days, and the average of the three consecutive days is the biomarker sampling parameter.

After the biomarker sampling parameter is obtained, the value is compared to a target biomarker range. As used herein, the target biomarker range means an acceptable range of biomarker in the diabetic person, which thereby demonstrates that the insulin is producing the desired physiological response. If the biomarker sampling parameter falls outside of the target biomarker range, then an insulin adjustment parameter may be calculated 790. The insulin adjustment parameter is associated with and computed from the biomarker sampling parameter. Various methodologies and algorithms are contemplated for calculating the insulin adjustment parameter. For example, the insulin adjustment parameter may be computed by locating the insulin adjustment parameter associated with the biomarker parameter in an insulin adjustment parameter lookup table (See Table 1 above). As shown above in the exemplary insulin adjustment parameter lookup table of Table 1, there may be multiple tiers which dictate how much the insulin dosage should be adjusted. For example, a fasting glucose level below 100 mg/dl but above 56 mg/dl will necessitate no adjustment to the insulin dosage. The greater the deviation from the target range, the higher the adjustment of insulin in units.

After determining the insulin adjustment parameter, the insulin dosage may be adjusted by the amount of the insulin adjustment parameter, as long as the insulin adjustment does not raise the insulin dosage above the maximum allowable dosage. The adjusted insulin dosage cannot exceed a maximum level set by the healthcare provider. Upon determining the adjusted insulin dosage value, the diabetic person may then be instructed to collect at least one additional sampling set at the adjusted insulin dosage per the above described collection procedures. The biomarker sampling parameter, the insulin adjustment parameter, and the adjusted insulin dosage may be computed manually by the diabetic person or via a data processing device.

If the biomarker sampling parameter is within a target biomarker range, there is no adjustment of the insulin dosage. Moreover, the insulin dosage may be considered optimized depending on other applicable criteria. Specifically, an insulin dosage may be considered optimized if one biomarker sampling parameter is within a target biomarker range, or it may be considered optimized if at least two consecutive biomarker sampling parameters are within a target biomarker range 820. If the optimization definition requires at least two consecutive biomarker sampling parameters within a target biomarker range, the diabetic person is then instructed to collect at least one additional sampling set at the adjusted insulin dosage per the above described collection procedures. After the insulin dosage is considered optimized, the diabetic person is instructed to exit the structured collection protocol. After exiting the structured collection protocol 730, the diabetic person may conduct further structured collection protocols to determine the future efficacy of the optimized dosage.

In alternative embodiments, the diabetic patient may be instructed to exit the structured collection protocol 730 if the diabetic person has been undergoing the testing procedure for a long period, for example, 6 months or longer. Additionally, as described above, if there are multiple adherence or violation events, then the test may be automatically terminated by the data processing device or the diabetic patient may be instructed to exit the structured collection protocol.

Classification Based on Adherence Criteria

In further embodiments, the structured collection procedures or protocol may utilize classifications of sampling instances in a sampling set in order to optimize the structured collection protocol. As described above, the structured collection protocol may comprise various calculations directed to assessment of a disease or therapy, the optimization of a therapy, or combinations thereof. In one embodiment, the structured collection protocol may be the insulin titration and optimization processes described above. The structured collection protocol may be performed on a collection device as described above, wherein the collection device may comprise a meter configured to measure one or more selected biomarkers, a processor disposed inside the meter and coupled to memory, wherein the memory comprises collection procedures, and software for the processor to execute.

Figure 20:
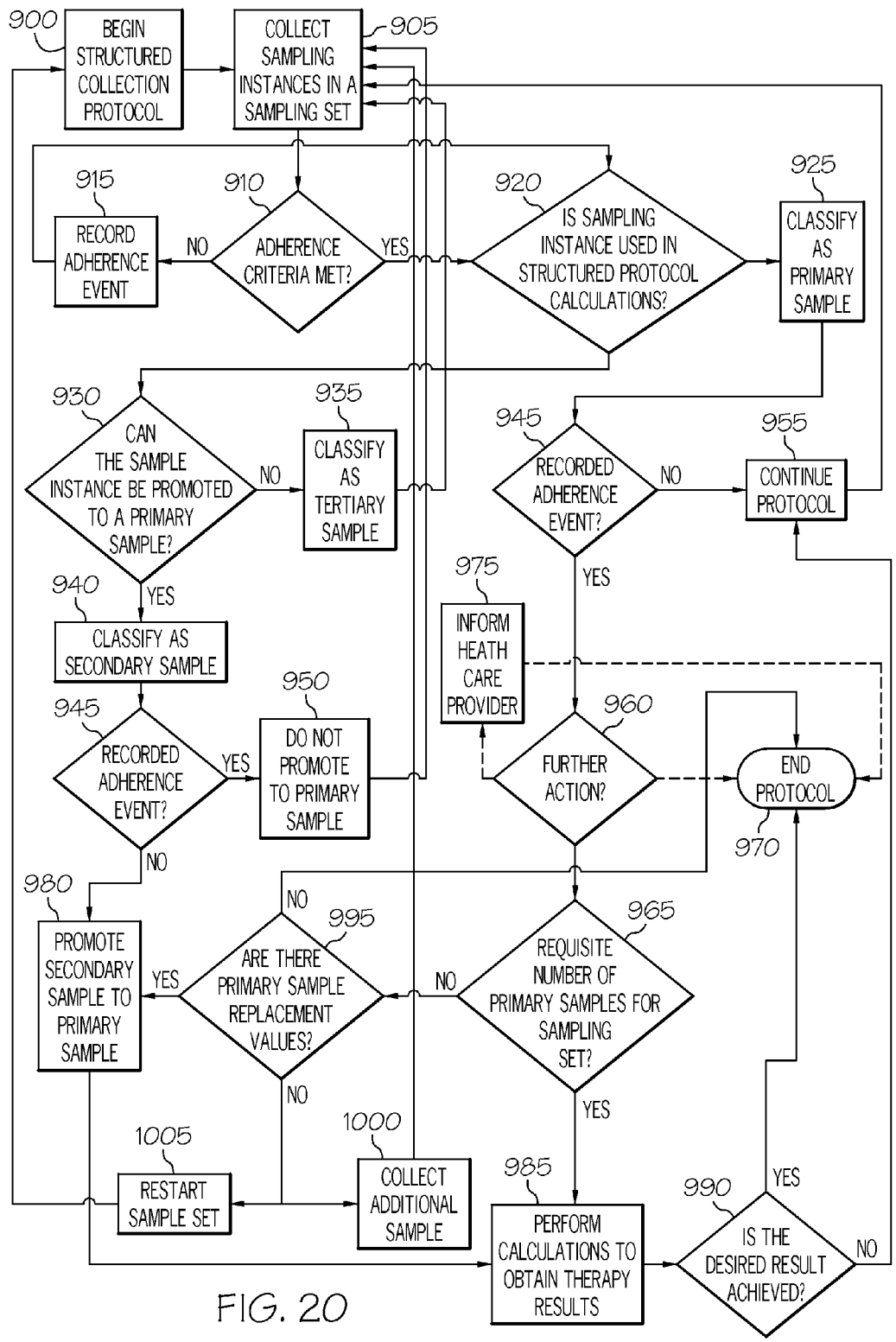
FIG. 20 is a flow chart depicting testing methods for optimizing the titration of insulin according to embodiments of the present invention.

Referring to FIG. 20, the user or diabetic patient begins the structured collection protocol 900 by collecting one or more sampling sets of biomarker data using the collection device

905, wherein each sampling set comprises a sufficient plurality of sampling instances recorded over a collection period. Each sampling instance includes a biomarker reading. In one embodiment, the processor may require the sampling instances to be non-adverse i.e., there are no biomarker readings indicative of hypoglycemia or hyperglycemia. For each sample, the processor may determine whether there is compliance with adherence criteria 915. Noncompliance with adherence criteria is recorded as an adherence event.

Referring to FIG. 20, either before or after collection, each sampling instance may be classified using the processor 920, 930. The samples may be classified as primary or secondary samples. Primary samples 925 are sampling instances intended to be utilized preferably in calculations performed by the processor that yield therapy results (e.g., adjusted insulin dosage amounts) for a diabetic person. As used herein, "therapy results" are metrics, data, contextual information yielded from the calculations performed in the structured collection protocol, wherein the structured collection protocol is directed to disease status assessment, therapy assessment, therapy optimization (e.g., insulin titration), or combinations thereof. As described above, primary samples may be construed as critical events, which should not be missed when conducting the structured testing protocol; however, they can be replaced with other samples. Secondary samples preferably are non-critical sampling instances not intended to be utilized in calculations performed by the processor that yield therapy results for a diabetic person 930, 940 unless the secondary samples are promoted to primary samples as described below. Regardless of whether samples are classified as primary or secondary, all sampling instances may be utilized in identifying adverse events, or measurement issues associated with the biomarker readings.

In further embodiments, it is contemplated to have additional classifications. For example, sampling instances may be classified as tertiary samples. Tertiary samples 935 are samples which cannot be promoted to primary samples as a replacement for another primary sample. While adherence is considered for tertiary samples, these values have no impact on the structured collection protocol. For example, but not by way of limitation, tertiary samples are sampling instances used for safety checks, as spacers to maintain a consistent sampling interval, or as input to visual presentations of reported data. It is contemplated to have further classifications in addition to primary, secondary, and tertiary. Like the primary and secondary samples, the tertiary samples may still be utilized to identify adverse events.

Referring to FIG. 20, for primary samples without corresponding recorded adherence events, the user may simply continue the protocol 955, or optionally determine if there are a sufficient number of primary samples in the sampling set, which have complied with adherence criterion.

For primary samples with corresponding recorded adherence events 945, the processor may determine which further action 960 or additional task is appropriate. While it is contemplated to terminate the protocol in light of adherence events, the embodiments of the present invention focus on compensating for these adherence events while continuing the performance of the structured collection protocol. The processor includes algorithms that calculate which additional task should be performed based on numerous factors. The algorithm may consider the contextual information for the sampling instances, the number of sampling instances, the classification of the sampling instances, the adherence of the sampling instances, and various other contemplated factors. Based on these factors, the algorithm selects the additional task most suitable for continuing the structured collection protocol In one embodiment, the processor may consider whether the sampling set has the requisite number of primary samples 965, without corresponding recorded adherence events. If so, the processor may perform the additional task of ignoring these primary samples with corresponding recorded adherence events and performing the calculations using primary samples, which do not include corresponding recorded adherence events, in order to obtain therapy results 985. Referring to FIG. 20, if the desired results of the protocol are achieved 990 (e.g., the insulin dosage is optimized), the user may be instructed to end the protocol 970.

Alternatively, if there are not a sufficient number of primary samples without recorded adherence events in the sampling set, the collection device may consider whether there are secondary samples which are suitable replacements for the primary sample 995. In this case, if there are secondary samples, which do not have corresponding recorded adherence events, these secondary samples may be promoted to primary samples and may replace the primary samples with associated adherence events 980. In another exemplary embodiment, the replacement of the primary samples may be performed automatically via the processor. When replacing a primary sample with a secondary sample, the processor may require that the primary sample and the secondary sample be part of the same sampling set. Moreover, when replacing a primary sample with a secondary sample, the processor may also require that the secondary sample comprise the same, substantially identical, partially identical or similar contextual information or metric as the primary sample to be replaced. For example, the processor may replace a primary fasting blood glucose level with a secondary fasting blood glucose level since the primary and secondary samples would have the same metric. In contrast, the processor would not replace a primary fasting blood glucose level with a secondary insulin to carbohydrate reading because the metrics i.e. contextual information is not the same. Unlike primary samples, adherence events for secondary samples may not require any further action or additional tasks to be performed (e.g. replacement); however, recorded adherence events may render a secondary sample unsuitable for a replacement for a primary sample 950. If there are no suitable replacement samples, for example, due to adherence events, the collection device may instruct the user to collect at least one additional sampling instance 1000 to be used as a primary sample in the structured collection protocol. In another embodiment, the processor may instruct the diabetic person to restart the sampling set 1005, without first terminating the protocol.

While the embodiments of the present invention are primarily focused on extending the structured collection protocol to compensate for primary samples with adherence events, the processor may, in some embodiments, instruct the user to end the protocol 970, because of the adherence event. Alternatively, the user may be instructed to contact a healthcare provider 975. It is contemplated that the user may be instructed to both end the protocol and contact the healthcare provider.

To reiterate, the at least one additional task is calculated by the processor if one or more sampling instances is recorded with a corresponding recorded adherence event and the sampling instance is classified as a primary sample. For example, if an adherence event is recorded for a primary sample, the system may calculate a resulting task, for example, replacing the primary sample by a secondary sample which fulfills the adherence criteria. As a consequence, the secondary sample is promoted as a primary sample.

However, if an adherence event for a secondary sample is recorded, which might be the same adherence event as recorded for the primary sample as exemplarily mentioned above, the resulting consequence that is calculated by the system may be different. For example, the resulting task may be to block that secondary sampling instance from further calculation, and thereby preclude this secondary sample from being used as a primary sample.

By dynamically calculating a task resulting from an adherence event, the system facilitates the flexible handling of the structured collection protocol. In particular, in case of an incorrect handling of the protocol by the user or a detection of undesired value, the system allows continuing the protocol so that the stored data is not wasted and can be evaluated within the structured collection protocol. Based on one or more embodiments, a differentiation between different classifications of sampling instances is possible so that an adherence event can be flexibly handled by the system. For example, adherence events for primary samples should not be used in the calculations of the structured collection protocol. However, adherence events for secondary samples are primarily utilized in determining whether a secondary sample is suitable as a primary sample, and do not require replacement of the secondary sample in the sampling set. Moreover, adherence events for tertiary samples are recorded; however, the tertiary samples are not utilized in the calculations of the structured collection protocol.

The above described embodiments of the classification centered on adherence generally; however, the embodiments of the present invention may also encompass acceptance criteria, which are defined above as a subset of adherence criteria. In one embodiment, the acceptance criteria may require a biomarker reading to be within an expected range. In some instances, a biomarker reading outside of the expected range may be indicative of an adverse event. It is contemplated that the structured collection protocol may compensate for this adverse event by utilizing the procedures illustrated in FIG. 20.

Structured Collection Data Redundancy and Compression

Referring again to FIG. 2, various patient data may be collected by a collection device 24 following structured collection procedures 70. Upon being collected, the patient data may be written to at least one memory communicably coupled to the collection device 24. It is noted that the term "communicably coupled," as used herein, means an exchange of data via a communication medium such as for example, electrical transmission over a conductive medium, electromagnetic transmissions over the air, optical transmissions over a waveguide, and the like. Thus, as depicted in FIG. 3, patient data may be written to the main memory 110 of the collection device 24, a secondary memory 112, a computer readable medium, a network database and/or any other storage medium communicably coupled to the collection device 24.

The patient data written to the at least one memory may be accessed by a physician to administer and/or evaluate therapy, as is described in greater detail herein. Since certain patient data may alter the therapy administered to a patient, it may be desirable to have at least one memory where certain data is duplicated for system redundancy in order to increase the reliability of data retrieval. For example, a fully redundant system wherein all patient data is duplicated complies with medical device standard EN-IEC 60601. It is noted that duplicating data has specific utility and may be useful to increase the probability of retrieving patient data after a memory error. Duplicate data may also increase the probability of data anomalies and corruption which may ultimately cause the loss of patient data. Furthermore, any duplication of patient data also results in an increased consumption of memory. Thus, any memory that duplicates data may waste memory space and may be non-optimal.

Data segregation is a logical concept that may be implemented through various logical and physical constructs to facilitate full or partial data redundancy. Logical segregation controls the quantity of addressable segments of data that are accessible (e.g., for writing, reading, overwriting or deleting) by processes executed by a processor communicably coupled to the at least one memory such as, for example, the processor 102 of the collection device 24. Thus, patient data may be divided into distinct data stores where access to and from the data store is controlled by logical segregation. The patient data may be segregated such that the patient data is written to distinct physical modules of the at least one memory corresponding to each of the data stores (i.e., written to separate hardware devices). Patient data may be segregated such that the patient data is written to data stores within a single hardware device of the at least one memory. Moreover, patient data may be segregated by a combined scheme where patient data is written to distinct data stores such that at least one of the data stores is maintained on a single hardware device and a multiplicity of the distinct data stores is maintained on a single hardware device.

By employing multiple distinct data stores, the storage requirements for data redundancy may be decreased through a data approach, an information approach and/or compression. A data approach may be implemented, wherein all data associated with a result is duplicated and/or retained while unassociated data is omitted from duplication and/or storage. An information approach may also be implemented, wherein only the data necessary to reconstruct a result and/or the data necessary to generate the result is duplicated and/or retained. Specifically, a data abstraction may be generated to operate as a link to a result and/or the data necessary to generate the result. The data abstraction may be a transformation of the result and/or the data necessary to generate the result that is an indirect representation of the data such as, for example, a unique identifier, a pointer or a combination thereof.

The data abstraction may also be the result of a transformation of the result and/or the data necessary to generate the result into a compressed data, i.e., transforming a data instance by a data compression algorithm such as, for example, a lossless data compression algorithm or a lossy data compression algorithm. The memory required to store data residing in the multiple distinct data stores can also be reduced utilizing a data compression algorithm. Therefore, storage requirements may be reduced via omission, reference, compression, and combinations thereof. It is noted that, as used herein, the terms "transform" and "transformation" refer to a change in form or structure of an input value, wherein the input persists or does not persist.

Furthermore, data abstractions may be utilized to link partial data sets to complete data sets in order to achieve full redundancy through partial duplication. Specifically, patient data may be collected in a casual manner (e.g., bG data, carbohydrates associated with meals, and the like) and in a structured manner (e.g., via a structured collection procedure). The casual patient data may be written substantially comprehensively in a primary data store. Structured patient data may be written to a secondary data store that is segregated from the primary data store. When the structured patient data is a subset of the casual patient data, a functional equivalent to a fully redundant system may be created by associating the casual patient data and the structured patient data to a data abstraction. The data abstraction may be, for example, written to the primary data store and/or the secondary data store and associated with the casual patient data and the structured patient data in order to link the casual patient data with the structured patient data.

Structured patient data may be transformed into an evaluated data object in order to facilitate the generation of a data abstraction. Specifically, structured patient data may be evaluated in order to determine if the structured patient data is to be reduced via omission, reference, compression, or combinations thereof. For example, the evaluated data object may be a classification (e.g., primary sample, secondary sample, or a tertiary sample) of the structured patient data, as is described hereinabove. Thus, the structured patient data classified as primary samples may be written to a data store differently than secondary samples and tertiary samples. Moreover, the evaluated data object, based at least in part upon the structured patient data, may be utilized as a portion of the data abstraction. For example, the evaluated data object may be a result (e.g., an adherence event, a violation event, a therapy result, a disease assessment, a therapy assessment, a therapy optimization and/or an adverse event (but not a bG value)) that can be associated with structured patient data and/or casual patient data.

Figure 21:
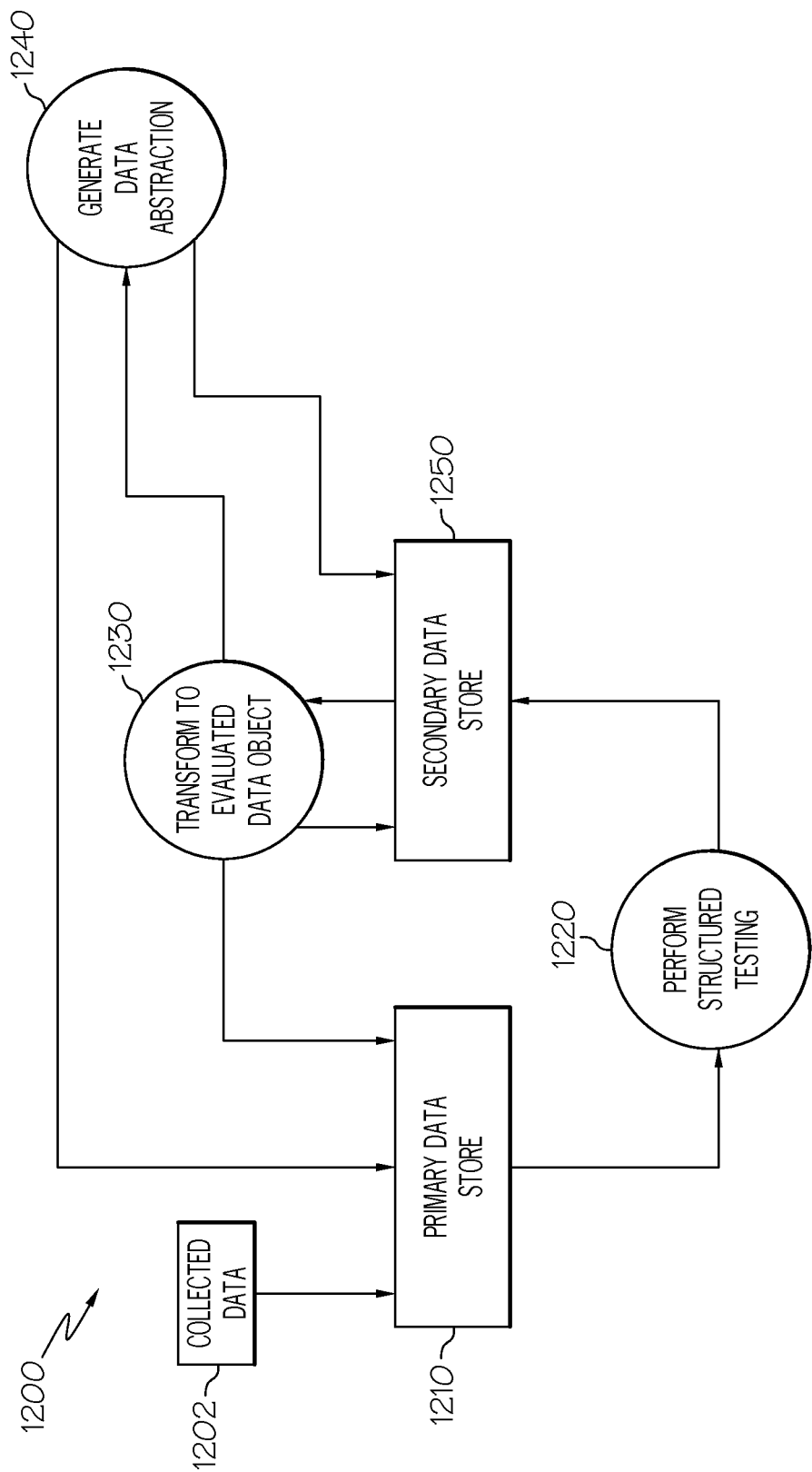
FIG. 21 depicts a data flow diagram depicting the flow of data collected from a structured collection procedure according to embodiments of the present invention.

Referring to FIG. 21, data flow 1200 according embodiments of the present disclosure is depicted. The at least one memory may be segregated into a primary data store 1210 and a secondary data store 1250. The primary data store 1210 may be utilized to store all of the collected data 1202 collected, for example, by the collection device 24. The collected data 1202 may include patient data such as, for example, biomarker data, date-time stamps, completion flags, contextualized data, and the like. While the secondary data store 1250 may be utilized to duplicate and store a portion of the data stored in the primary data store 1210. Such data may be duplicated by copying and/or by generating a data abstraction. In a further embodiment, the data abstraction may be written to a tertiary data store (not depicted) and may be limited to data related to the administration of therapy, i.e., data commonly accessed by a physician to administer and/or alter the therapy of a patient.

In one embodiment, collected data 1202 includes structured patient data collected by performing structured testing 1220, i.e., the structured patient data may be collected in accordance to a schedule of events 222 (FIG. 5B). The structured patient data can be written to the secondary data store 1250. The data flow 1200 may further include the process 1230 of transforming a relevant portion of the structured patient data into an evaluated data object (e.g., a classification, a disease assessment, a therapy assessment, or a therapy optimization), as is described in greater detail above. After the evaluated data object is instantiated, the evaluated data object may be written automatically to the secondary data store 1250 and associated with the primary data store 1210. Specifically, the evaluated data object may be written directly or indirectly to the primary data store 1210 depending on the type of data abstraction utilized. In further embodiments, the evaluated data object may be written automatically to the primary data store 1210 and associated with the secondary data store 1250.

Referring still to FIG. 21, data flow 1200 depicts the process 1240 of generating a data abstraction. The data abstraction is a transformation of data stored in the secondary data store 1250 that is an indirect representation of the data. The unique identifier may be a unique value that is stored with and/or associated with the relevant portion of the data. The unique value (e.g., an incremental count or metadata) may be capable of identifying data instances such the data instance may be retrieved from the primary data store 1210 by, for example, querying for the unique value. The unique value may also be the result of a transformation of the data instance into a compressed data, i.e., transforming the data instance by a data compression algorithm such as, for example, a lossless data compression algorithm or a lossy data compression algorithm.

In one embodiment, the data abstraction may be associated with an associated portion of the structured patient data. Specifically, the data abstraction may be written to the secondary data store 1250, i.e., appended to a data structure of the associated portion of the structured patient data or stored as a separate data structure with linking information. When a data abstraction is generated, data from the secondary data store 1250 may be transformed into a unique identifier, a pointer or a combination thereof, as is described hereinabove. The data abstraction may be a unique identifier indicative of a corresponding portion of the casual patient data written in the primary data store 1210. For example, the corresponding portion of the casual patient data may be duplicate data or sufficient data to reconstruct the relevant portion of the structured patient data. Additionally, the data abstraction may be a relevant portion pointer indicative of a corresponding address of the primary data store. The corresponding address of the primary data store may be a data pointer that is associated with an address of the primary data store. Duplicate data and/or data the can be used to reconstruct the relevant portion of the structured patient data may be written at the address of the primary data store. Furthermore, the data abstraction may include reconstruction information that enables the program instructions cause the processor to reconstruct a reconstructed structured patient data corresponding to structured patient data written to the secondary data store 1250. Thus, the structured patient data may be generated even if the structured patient data is lost, corrupted, deleted and/or overwritten.

In some embodiments, only a subset of the structured patient is associated with a data abstraction. The remainder of the structured patient may be classified as a non-relevant portion of the structured patient data which is not the associated portion of the structured patient data. When new structured patient data is written to the secondary data store 1250, the non-relevant portion of the structured patient data may automatically be overwritten to reduce the amount of physical memory required for storage. In another embodiment, the non-relevant portion of the structured patient data may be compressed with a data compression algorithm. In a further embodiment, the data stores may be reset such that all of the structured patient data becomes unassociated (i.e., converted to the non-relevant portion). Thus, if, for example, a health care professional were to retrieve data from the at least one memory, the data stores could be reset such that all of the retrieved data may be overwritten and/or deleted.

As is noted above, a data abstraction may be associated with at least one instance of the casual patient data (e.g., bG value) written in the primary data store 1210. The data abstraction may be written directly or indirectly to the primary data store, i.e., appended to a data structure of the casual patient data or stored as a separate data structure. For example, a data structure may be created that appends the data abstraction to the casual patient data or through the use of an indexing system that correlates the data abstraction to the casual patient data. In one embodiment, the data abstraction may be an evaluated data object pointer indicative of an address of the secondary data store. The address may correspond to the memory location of the evaluated data object stored in the secondary data store. Moreover, data abstraction may be associated dynamically (e.g., the data abstraction may be associated with a primary sample after it has been promoted from being a secondary sample).

Data redundancy may be supported by dynamic and/or static allocation of the at least one memory. Memory allocation relates to the physical quantity of memory allocated to each of the logical segregated data stores of the at least one memory. Thus, the physical quantity of the at least one memory (e.g., bytes of RAM) may remain fixed or may be varied as the logical allocation of the at least one memory is altered, i.e., increased or decreased. In one embodiment, the quantity of logically accessible segments available to the primary data store 1210 and/or the quantity of logically accessible segments available to the secondary data store 1250 may be allocated prior to initiating the schedule of events. In another embodiment, the quantity of logically accessible segments available to the primary data store 1210 and/or the quantity of logically accessible segments available to the secondary data store 1250 may be allocated after an event of the schedule of events ends.

An error checking algorithm may be executed to check for errors on each data store of the at least one memory prior to and/or after writing data to the data store. In one embodiment, an error checking algorithm is applied the primary data store after writing to the primary data store and a different error checking algorithm is applied to the secondary data store after writing to the secondary data store. Error checking algorithms are configured to transform data to a substantially unique result. For example, all of the data written in a data store may be combined (e.g., summed) with the combined value transformed into a hash value (i.e., checksum). The hash value may then be stored at a known location and later accessed by a processor. After writing data to the data store, the error checking algorithm may be executed to generate a new hash value. If the new hash value matches the stored hash value, the data store may be free of errors (e.g., data corruption, transmission errors and the like). Non-limiting examples of error checking algorithms include cyclic redundancy checks, checksums, hash functions, and the like.

Figure 22:
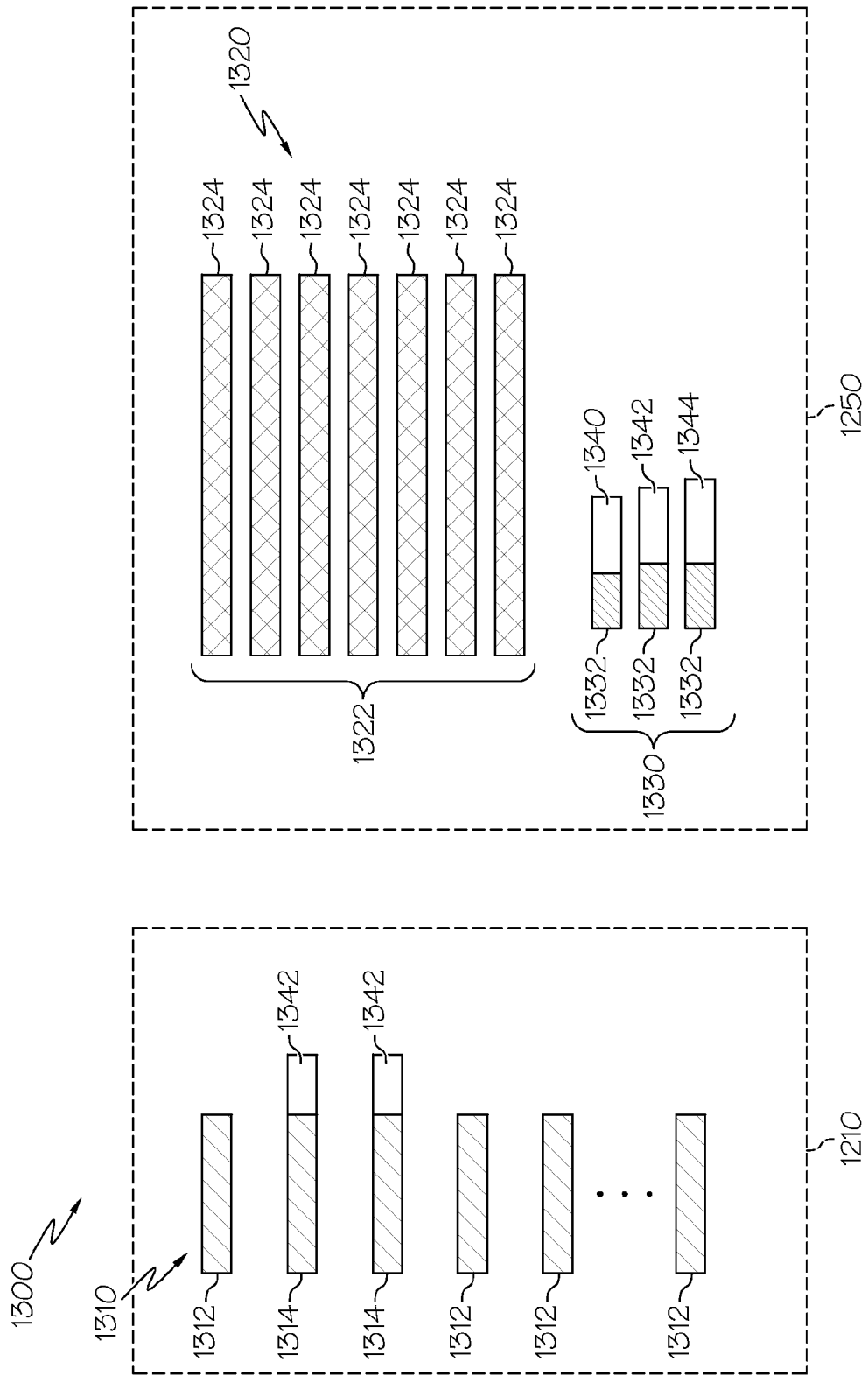
FIG. 22 schematically depicts the flow of data collected from a structured collection procedure according to embodiments of the present invention.

Referring now to FIG. 22, an embodiment of logical segregation 1300 is schematically depicted. As is described in greater detail herein, data abstractions such as unique identifiers may be utilized to link data across a plurality of data stores. In one embodiment, the logical segregation system comprises a primary data store 1210 and a secondary data store 1250 on at least one memory. The primary data store 1310 comprises casual patient data 1312 and associated casual patient data 1314. The secondary data store 1250 comprises at least one structured testing instance 1320. Each structured testing instance 1320 comprises at least one sample group which can be identified sequentially (e.g., date, time and/or memory location).

A structured testing instance 1320 may include a running sample group data vector 1322, which may include at least one running sample instance data vector 1324. Such running data is maintained as required for the generation of an evaluated data object 1332 (e.g., until all of the running data can be classified as a primary sample or a secondary sample). Therefore, each running sample instance data vector 1324 may include sufficient data (e.g., recommended insulin administration amount, the confirmed insulin administration amount, whether the user administered their insulin, whether the user affirmed they were fasting in the morning, and/or the associated bG value) for the generation of an evaluated data object 1332 (e.g., a disease status assessment, a therapy assessment, a therapy optimization, or combinations thereof). Once the evaluated data object has been instantiated, the running data may be transformed into historical data 1330.

The historical data 1330 may include data from prior sample groups within the structured testing instance 1320. The amount of physical memory required to store historical data 1330 may be reduced by storing the evaluated data object 1332 rather than the full sample instance data vector. Additional reductions to the amount of physical memory required to store historical data 1330 can be achieved by omitting data based upon the evaluated data object 1332, e.g., by omitting secondary samples and tertiary samples. Moreover, historical data 1330 may be compressed via compression algorithms to reduce the amount of physical memory required for storage.

In order to link the primary data store 1210 and the secondary data store 1250, each of the evaluated data objects 1332 may be concatenated with a data abstraction. For example, the data abstraction may include a unique identifier, a sample group number, an indication whether the sample is primary, secondary, or tertiary, and an indication whether the sample group was accepted. In the embodiment depicted in FIG. 22, a first data abstraction 1340, a second data abstraction 1342, and a third data abstraction 1344 are concatenated to an evaluated data object 1332. When each of the first data abstraction 1340, the second data abstraction 1342, and the third data abstraction 1344 is distinct, one of the data abstractions may be concatenated to the associated casual patient data 1314 to link the associated casual patient data 1314 of the primary data store 1210 and the evaluated data object 1332 of the secondary data store 1250. Specifically, in the depicted embodiment, the second data abstraction 1342 links historical data 1330 to the associated casual patient data 1314.

It should now be understood that by providing linked data stores, the embodiments described herein offer redundant data segregation and efficient use of memory. Comprehensive bG sample information may be stored in a first data store, while a reduced amount of data including therapy change information such as dosage recommendation, average bG value, and new recommended insulin dosage may be stored in a second data store. Thus, a user may scroll through all acquired bG information, in order of acquisition, on a device while a reduced amount of data is duplicated in a second data store. Moreover, the full data set may be re-created the data set for a health care professional reviewing the therapy change information. As a result, patient data that alters therapy administered to a patient may have increased reliability in storage and retrieval.

Thus, by the above disclosure embodiments concerning a system and method managing the execution, data collection, and data analysis of collection procedures running simultaneously on a meter are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A collection device for performing a structured collection procedure, the collection device comprising:
a processor communicably coupled to at least one memory; and
program instructions which when executed by the processor cause the processor to:
initiate a schedule of events of the structured collection procedure upon one or more entry criterions being met;
segregate the at least one memory into a primary data store and a secondary data store;

write structured patient data collected in accordance to the schedule of events to the secondary data store of the at least one memory;

transform a relevant portion of the structured patient data into an evaluated data object;

generate a data abstraction based at least in part upon the evaluated data object; and link the primary data store and the secondary data store with the data abstraction;

wherein the at least one memory comprises dynamic and static allocation such that the quantity of the at least one memory can remain fixed, can be increased, and can be decreased; and the program instructions when executed by the processor cause the processor to:

mark the collection procedure as complete if there are no exceptions;

signify that appropriate data has not been collected if there are the exceptions;

resolve any of the exceptions that have arisen at the time of execution of the collection procedure; and change the structured collection procedure by switching to a secondary schedule of events that is easier for a patient to perform.

2. The collection device of claim 1, wherein the relevant portion of the structured patient data comprises a primary sample, wherein the primary sample is promoted from a secondary sample.

3. The collection device of claim 1, wherein the program instructions cause the processor to write casual patient data collected by the collection device to the primary data store of the at least one memory.

4. The collection device of claim 3, wherein the structured patient data is a subset of the casual patient data, and the program instructions cause the processor to:

write the data abstraction to the primary data store and/or the secondary data store;

associate the data abstraction with an associated portion of the structured patient data, wherein a non-relevant portion of the structured patient data is not the associated portion of the structured patient data; and omit the non-relevant portion of the structured patient data from the secondary data store of the at least one memory.

5. The collection device of claim 4, wherein the program instructions cause the processor to compress the associated portion of the structured patient data with a data compression algorithm.

6. The collection device of claim 3, wherein the program instructions cause the processor to write automatically the evaluated data object to the secondary data store.

7. The collection device of claim 3, wherein the program instructions cause the processor to:

associate the data abstraction with an associated portion of the structured patient data; and write the data abstraction to the secondary data store.

8. The collection device of claim 7, wherein the data abstraction is a unique identifier indicative of a corresponding portion of the casual patient data written in the primary data store, wherein the corresponding portion of the casual patient data corresponds to the relevant portion of the structured patient data.

9. The collection device of claim 7, wherein the data abstraction is a relevant portion pointer indicative of a corresponding address of the primary data store, wherein the corresponding address of the primary data store corresponds to the relevant portion of the structured patient data.

10. The collection device of claim 7, wherein the data abstraction comprises reconstruction information indicative of an address of the primary data store corresponding to the casual patient data and the program instructions cause the processor to reconstruct a reconstructed structured patient data corresponding to the structured patient data written to the secondary data store.

11. The collection device of claim 7, wherein a non-relevant portion of the structured patient data is not the associated portion of the structured patient data, and the program instructions cause the processor to compress the non-relevant portion of the structured patient data with a data compression algorithm.

12. The collection device of claim 6, wherein the program instructions cause the processor to:

associate the data abstraction with at least one instance of the casual patient data; and write the data abstraction to the primary data store.

13. The collection device of claim 12, wherein the data abstraction is an evaluated data object pointer indicative of an address of the secondary data store corresponding to the evaluated data object stored in the secondary data store.

14. The collection device of claim 1 wherein:

the primary data store comprises a first quantity of logically accessible segments;

the secondary data store comprises a second quantity of logically accessible segments; and the first quantity of logically accessible segments and/or the second quantity of logically accessible segments are allocated prior to initiating the schedule of events.

15. The collection device of claim 1 wherein:

the primary data store comprises a first quantity of logically accessible segments;

the secondary data store comprises a second quantity of logically accessible segments;

the program instructions cause the processor to increase the first quantity of logically accessible segments and/or the second quantity of logically accessible segments after an event of the schedule of events ends.

16. The collection device of claim 1, wherein the evaluated data object is a therapy result, a disease assessment, a therapy assessment, a therapy optimization and/or an adverse event.

17. The collection device of claim 3, wherein the casual patient data comprises biomarker data, a date-time stamp, a completion flag, or contextualized data.

18. The collection device of claim 1, wherein the at least one memory comprises a main memory disposed within the collection device.

19. The collection device of claim 1, wherein the at least one memory comprises a computer readable medium and/or a network database.

20. The collection device of claim 1, wherein the program instructions cause the processor to:

apply an error checking algorithm to the primary data store after writing to the primary data store; and apply a different error checking algorithm to the secondary data store after writing to the secondary data store.

21. The collection device of claim 20, wherein each of the error checking algorithm and the different error checking algorithm is a cyclic redundancy check.

22. A collection device for performing a structured collection procedure, the collection device comprising:

a processor communicably coupled to at least one memory wherein the at least one memory comprises dynamic and static allocation such that the quantity of the at least one memory can remain fixed, can be increased, and can be decreased; and program instructions which when executed by the processor cause the processor to:
  initiate a schedule of events of the structured collection procedure upon one or more entry criterions being met;
  segregate the at least one memory into a primary data store and a secondary data store;
  write casual patient data collected by the collection device to the primary data store of the at least one memory;
  write structured patient data collected in accordance to the schedule of events to the secondary data store of the at least one memory;
  transform a relevant portion of the structured patient data into an evaluated data object, the evaluated data object is a therapy result, a disease assessment, a therapy assessment, a therapy optimization and/or an adverse event;
  write automatically the evaluated data object to the secondary data store;
  apply an error checking algorithm to the primary data store after writing to the primary data store;
  apply a different error checking algorithm to the secondary data store after writing to the secondary data store;
  link the primary data store and the secondary data store with the evaluated data object; and
  mark the collection procedure as complete if there are no exceptions;
  signify that appropriate data has not been collected if there are the exceptions;
  resolve any of the exceptions that have arisen at the time of execution of the collection procedure; and
  change the structured collection procedure by switching to a secondary schedule of events that is easier for a patient to perform.

23. A method for managing data collected from a structured collection procedure comprising:
  providing at least one memory comprising dynamic and static allocation such that the quantity of the at least one memory can remain fixed, can be increased, and can be decreased;
  initiating a schedule of events of the structured collection procedure upon one or more entry criterions being met;
  segregating the at least one memory into a primary data store and a secondary data store;
  writing casual patient data collected by a collection device to the primary data store of the at least one memory;
  writing structured patient data collected in accordance to the schedule of events to the secondary data store of the at least one memory;
  transforming a relevant portion of the structured patient data into an evaluated data object;
  generating a data abstraction based at least in part upon the evaluated data object;
  linking the primary data store and the secondary data store with the data abstraction; and
  if there are no exceptions, marking the collection procedure as complete;
  if there are the exceptions, signifying that appropriate data has not been collected;
  resolving any of the exceptions that have arisen at the time of execution of the collection procedure; and
  changing the structured collection procedure by switching to a secondary schedule of events that is easier for a patient to perform.

24. The method of claim 23, further comprising writing automatically the evaluated data object to the secondary data store.

25. The method of claim 24, further comprising:
  associating the data abstraction with an associated portion of the structured patient data; and
  writing the data abstraction to the secondary data store.

26. The method of claim 25, further comprising resetting automatically the secondary data store wherein the associated portion of the structured patient data is unassociated.

27. The method of claim 24, further comprising:
  associating the data abstraction with at least one instance of the casual patient data; and
  writing the data abstraction to the primary data store.

* * * * *